US008071635B2

(12) United States Patent
Chow et al.

(10) Patent No.: US 8,071,635 B2
(45) Date of Patent: *Dec. 6, 2011

(54) 4-(SUBSTITUTED CYCLOALKYLMETHYL) IMIDAZOLE-2-THIONES, 4-(SUBSTITUTED CYCLOALKENYLMETHYL) IMIDAZOLE-2-THIONES, 4-(SUBSTITUTED CYCLOALKYLMETHYL) IMIDAZOL-2-ONES AND 4-(SUBSTITUTED CYCLOALKENYLMETHYL) IMIDAZOLE-2-ONES AND RELATED COMPOUNDS

(75) Inventors: Ken Chow, Newport Coast, CA (US); Todd Heidelbaugh, Fountain Valley, CA (US); Daniel Gil, Corona Del Mar, CA (US); Michael Garst, Newport Beach, CA (US); Larry A. Wheeler, Irvine, CA (US); Phong X. Nguyen, Placentia, CA (US); Dario G. Gomez, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/070,297

(22) Filed: Feb. 16, 2008

(65) Prior Publication Data

US 2008/0221186 A1    Sep. 11, 2008

Related U.S. Application Data

(60) Division of application No. 11/143,334, filed on Jun. 2, 2005, now Pat. No. 7,345,077, which is a division of application No. 10/437,807, filed on May 14, 2003, now Pat. No. 7,091,232, which is a continuation-in-part of application No. 10/153,328, filed on May 21, 2002, now abandoned.

(51) Int. Cl.
*A61K 31/4164* (2006.01)
*C07D 233/30* (2006.01)

(52) U.S. Cl. ............ 514/392; 548/316.4; 548/325.1; 514/385; 514/386; 546/112; 546/152

(58) Field of Classification Search ............ 548/300.1, 548/316.4, 325.1; 514/385, 386, 392; 546/112, 546/152
See application file for complete search history.

(56) References Cited

U.S. PATENT DOCUMENTS

| | | | | |
|---|---|---|---|---|
| 3,996,366 A | 12/1976 | Baker et al. | | 424/273 |
| 4,798,834 A | 1/1989 | Merritt et al. | | 514/288 |
| 4,977,174 A | 12/1990 | Stein et al. | | 514/382 |
| 5,441,970 A | 8/1995 | Reitz et al. | | 514/340 |
| 5,648,373 A | 7/1997 | Winkler et al. | | 514/398 |
| 5,861,420 A | 1/1999 | Reitz et al. | | 514/338 |
| 5,929,103 A | 7/1999 | Yoon et al. | | 514/392 |
| 5,932,742 A | 8/1999 | Yoon et al. | | 548/312 |
| 6,043,373 A | 3/2000 | Yoo et al. | | 548/148 |
| 6,313,172 B1 | 11/2001 | Chow et al. | | 514/587 |
| 6,465,486 B1 | 10/2002 | Baxter et al. | | 514/311 |
| 6,534,542 B2 | 3/2003 | Chow et al. | | 514/546 |
| 6,545,182 B2 | 4/2003 | Chow et al. | | 564/587 |
| 7,091,232 B2 | 8/2006 | Chow et al. | | 514/386 |
| 7,141,597 B2 | 11/2006 | Chow et al. | | 514/392 |
| 7,183,305 B2 | 2/2007 | Dolby et al. | | 514/396 |
| 7,345,077 B2 * | 3/2008 | Chow et al. | | 514/399 |
| 7,419,994 B2 * | 9/2008 | Chow et al. | | 514/392 |
| 7,569,584 B2 * | 8/2009 | Heidelbaugh et al. | | 514/314 |
| 2002/0094998 A1 | 7/2002 | Burke et al. | | |

FOREIGN PATENT DOCUMENTS

| | | |
|---|---|---|
| WO | 1 499 485 | 2/1978 |
| WO | WO 92/00073 | 1/1992 |
| WO | WO 99/28300 | 6/1999 |
| WO | WO 01/00586 | 1/2001 |
| WO | WO 02/36162 A2 | 5/2002 |
| WO | WO 03/099795 | 12/2003 |

OTHER PUBLICATIONS

Burke et al (2002): STN International HCAPLUS database, Columbus (OH), accession No. 2002: 353314.*

Berque et al., Allyltitanates in Stereospecific Additions of Chiral o-Lactol: Efficient Enantioselective Route to a Potential Precursor of the C1-C9 Portion of Tylonolide, J. Org. Chem., 1999, 373-381.

(Continued)

*Primary Examiner* — Golam M M Shameem
(74) *Attorney, Agent, or Firm* — Doina G. Ene; Allergan, Inc.

(57) ABSTRACT

Compounds of Formula 1

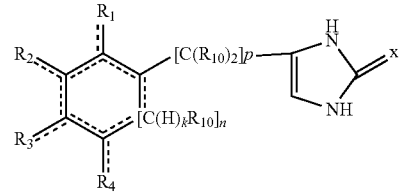

Formula 1 where X is S and the variables have the meaning defined in the specification are specific or selective to alpha$_{2B}$ and/or alpha$_{2C}$ adrenergic receptors in preference over alpha$_{2A}$ adrenergic receptors, and as such have no or only minimal cardiovascular and/or sedatory activity. These compounds of Formula 1 are useful as medicaments in mammals, including humans, for treatment of diseases and or alleviations of conditions which are responsive to treatment by agonists of alpha$_{2B}$ adrenergic receptors. Compounds of Formula 1 where X is O also have the advantageous property that they have no or only minimal cardiovascular and/or sedatory activity and are useful for treating pain and other conditions with no or only minimal cardiovascular and/or sedatory activity.

9 Claims, No Drawings

OTHER PUBLICATIONS

Ciufolini et al., The Total Synthesis of Cystodytins, J. Amer. Chem. Soc., 1991, 113, 8016-8024.

Conklin et al., Substitution of three amino acids switches receptor specificity of $G_p a$ to that of $G_f a$ Nature, 1993, p. 274-276, 363.

Cooke et al., Silicon in Synthesis, 8.[1] Vinyltrimethylsilane, a convenient ethylene equivalent for the Synthesis of Vinyl Aryl Sulfides, Vinyl Aryl Sulfoxides, Thiosilketene Acetals, and Fused Cyclopentenones, J. Org. Chem., 1980, 45, 1046-1053.

Corey et al., A new chiral catalyst for the enantioselective synthesis of secondary alcohols and deuterated primary alcohols by carbonyl reduction, Tetrahedron Letters, 1989, 30, 6275-6278.

Dirig, et al., Characterization of variables defining hindpaw withdrawal latency evoked by radiant thermal stimuli, J. Neurosci. Methods, 1997, 76, p. 183-191.

Dixon et al., Efficient Analysis of Experimental Observations, Ann. Rev. Pharmacol. Toxicol., 1980, 20, p. 441-462.

Hargreaves, et al., A new and sensitive method for measuring thermal nociception in cutaneous hyperalgesia, Pain, 1988, 32, p. 77-88.

Horne et al., A two-step synthesis of imidazoles from aldehydes via 4-tosyloxazolines, Heterocycles, 1994, 39, 139.

Hua et al., A one-pot condensation of pyrones and enals. Synthesis of 1H, 7H-5a, 6, 8, 9-Tetrahydro-1-oxopyrano[4,3-b][1]benzopyrans J. Org. Chem. 1997, 62, 6888-6896.

Huang et al., The Improved Preparation of 7,8-dihydro-quinoline-5(gH)-One and 6,7-dihydro-6H-1-pyrindin-5-one, Synthetic Communications, 1998, 28, 1197-1200.

Jackman, et al. (1949): STN International CAPLUS data base, Columbus, Ohio, Accession No. 1949:2664.

Jenneskens, et al., Flash vacuum thermolysis of 5,6,8,9-tetrahydro-4'-methylenesprio[7H-benzocycloheptene-7,1'-cyclohexa-2'5'-diene]. The intermediate formation of [3,2]orthoparacyclophane, J. Org. Chem. 1986, 51, 2162-2168.

Kim et al., an experimental model for peripheral neuropathy produced by segmental spinal nerve litigation in the rat, Pain, 1992, 150, p. 355-363.

Kim et al., A facile synthesis of a-chloro enones by oxidative chlorination, Synthesis, 1993, 283.

Kowalski et al., a-Keto dianion precursors via conjugate additions to cyclic a bromo enones, J. Org. Chem., 1982, 47, 5088-5093.

Lemke et al., Synthesis of 5,6-dihydro-8(7H)-quinolinone thiosemicarbazones as potential antitumor agents, J. Med. Chem., 1977,20,10,1351.

Mancuso, Activated dimethyl sulfoxide: useful reagents for synthesis, Synthesis, 1981, p. 165.

Messier et al., High throughput Assays of cloned adrenegeric, muscarinic, neurokinin, and neurotrophin receptors in living mammalian cells, Pharmacol. Toxicol., 1995,75,308-311.

Molina et al., Vinyliminophosphorane-mediated preparation of 2-aryiquinoline and 4-aryl-1-azaanthraquinone derivatives, x-ray crystal structure of 1,2-dihydro-3H-indazolo[2,3-a]quinolin-4-one, Tetrahedron, 1995,51, 1265-1276.

Organ et al., Ni-catalyzed cross coupling of alkoxide-containing vinyl halides with Grignard reagents. A "one-pot" synthesis of 2-[trimethylsily]-2-propen-1-yl acetate, J. Org. Chem., 1997, 62, 1523-1526.

Sosa et al., Synthesis of axinohydantoins, J. Org. Chem., 2002, 67, 4498-4500.

Woods et al., Synthesis with Dihydrorescorcinol mono ethyl ether: 3-alkykl-a2-cyclohexenones, J. Amer. Chem. Soc., 1949,71, 2028-2031.

Xavier et al., (s)-tetahydro-1-methyl-3,3-diphenyl-1H, 3H-pyrrolo-[1,2-c][1,3,2]oxazaborolen[7])-,[1-4-(3aS-cls)]-), Organic Synthesis, 1996, 50, 74.

Yoon, et al. (1998):STN International CAPLUS data base, Columbus, Ohio, Accession No. 1998: 147327.

\* cited by examiner

4-(SUBSTITUTED CYCLOALKYLMETHYL) IMIDAZOLE-2-THIONES, 4-(SUBSTITUTED CYCLOALKENYLMETHYL) IMIDAZOLE-2-THIONES, 4-(SUBSTITUTED CYCLOALKYLMETHYL) IMIDAZOL-2-ONES AND 4-(SUBSTITUTED CYCLOALKENYLMETHYL) IMIDAZOLE-2-ONES AND RELATED COMPOUNDS

CROSS-REFERENCE TO RELATED APPLICATION

The present application is a divisional of application Ser. No. 11/143,334, filed on Jun. 2, 2005 now U.S. Pat. No. 7,345,077 which is a divisional of application Ser. No. 10/437,807 filed on May 14, 2003, now U.S. Pat. No. 7,091,232 which is a continuation-in-part of application Ser. No. 10/153,328 filed on May 21, 2002 now abandoned.

BACKGROUND OF THE INVENTION

1. Field of the Invention

The present invention relates to 4-(substituted cycloalkylmethyl) imidazole-2-thiones, 4-(substituted cycloalkenylmethyl) imidazole-2-thiones and related compounds and to their use as specific or selective agonists of alpha$_{2B}$ and/or alpha$_{2C}$ adrenergic receptors. More specifically the present invention relates to the above-noted compounds, pharmaceutical compositions containing these compounds as active ingredient for modulating the alpha2B and/or alpha2C adrenergic receptors, and even more specifically for utilizing these compounds and pharmaceutical compositions to alleviate chronic pain, allodynia, muscle spasticity, diarrhea, neuropathic pain and other diseases and conditions.

The present invention also relates to, 4-(substituted cycloalkylmethyl) imidazol-2-ones and 4-(substituted cycloalkenylmethyl) imidazol-2-ones and to pharmaceutical compositions containing these compounds alleviate chronic pain, allodynia, muscle spasticity, diarrhea, neuropathic pain and other diseases and conditions.

2. Background Art

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha$_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the $\alpha$-adrenergic receptors, the reader's attention is directed to Robert R. Ruffolo, Jr., $\alpha$-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting $\alpha$-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha-2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

British Patent 1 499 485, published Feb. 1, 1978 describes certain thiocarbamide derivatives; some of these are said to be useful in the treatment of conditions such as hypertension, depression or pain.

PCT Publications WO01/00586 published on Jan. 4, 2002 and WO99/28300 published on Jun. 10, 1999 describe certain imidazole derivatives acting as agonists of alpha$_{2B}$ and/or alpha$_{2C}$ adrenergic receptors. U.S. Pat. No. 6,313,172 discloses phenylmethyl-thiourea derivatives used for treatment of pain.

U.S. Pat. No. 4,798,843 describes (phenyl)-imidazole-2-thiones and substituted (phenyl)-imidazole-2-thiones.

U.S. Pat. Nos. 6,545,182 and 6,313,172 describe phenylmethyl-(2hydroxy)ethylthioureas which have no significant cardiovascular or sedative effects and are useful for alleviating chronic pain and allodynia. U.S. Pat. No. 6,534,542 describes cycloalkyl, cycloalkenyl, cycloalkylmethyl and cycloalkenylmethyl (2-hydroxy)ethylthioureas and their use as specific or selective agonists of alpha$_{2B}$ adrenergic receptors. In a different biological or pharmaceutical context United States Published Application 20020094998, published on Jul. 18, 2002 and claiming priority of U.S. Provisional Application No. 60/244,850 discloses a compound without assigning the proper stereochemistry to it, which corresponds to two compounds described in the present application with the proper stereochemistry.

SUMMARY OF THE INVENTION

The present invention is directed to compounds of Formula 1

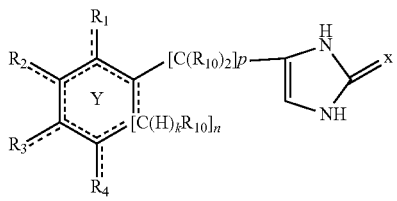

Formula 1 where the variable Y in the ring is optional and represents a heteroatom selected from N, O and S with the proviso that the N atom is trivalent, and the O or S atoms are divalent;

k is an integer having the values of 0 or 1;

n is an integer having the values 0, 1 or 2;

p is an integer having the values 0, 1 or 2;

X is O or S;

the dashed lines represent a bond, or absence of bond with the proviso that only one double bond is present in the ring and that two adjoining dashed lines do not both represent a bond;

$R_1$, $R_2$, $R_3$, and $R_4$ are independently H, phenyl, said phenyl group being optionally substituted independently with one, two or three $C_{1-6}$alkyl, $SO_3H$, $N_3$, halogen, CN, $NO_2$, $NH_2$, $C_{1-6}$alkoxy, $C_{1-6}$thioalkoxy, $C_{1-6}$alkylamino, $C_{1-6}$dialkylamino, $C_{2-6}$alkynyl, $C_{2-6}$alkenyl groups, 5 or 6 membered heteroaryl having 1 to 3 heteroatoms selected from O, S, and N, said heteroaryl groups being optionally substituted independently with one, two or three $C_{1-6}$alkyl, $SO_3H$, $N_3$, halogen, CN, $NO_2$, $NH_2$, $C_{1-6}$alkoxy, $C_{1-6}$thioalkoxy, $C_{1-6}$alkylamino, $C_{1-6}$dialkylamino, $C_{2-6}$alkynyl, $C_{2-6}$alkenyl groups, or said $R_1$, $R_2$, $R_3$, and $R_4$ groups being independently alkyl of 1 to 4 carbons, cycloalkyl of 3 to 5 carbons, $CH_2CN$, $CH_2SR_5$, $CH_2NR_6R_6$, $COR_5$, $CH_2OR_5$, $OR_6$, $SR_6$. $NR_6R_6$, alkenyl having 1 to 4 carbons, alkynyl having 1 to 4 carbons, cycloalkyl having 3 to 6 carbons, F, Cl, Br, I, $CF_3$, or CN, an oxygen double bonded to the ring carbon with the proviso that the adjacent dashed line within the ring represents absence of a bond;

$R_5$ is H, $OR_7$, alkyl of 1 to 4 carbons, $CF_3$, cycloalkyl of 3 to 6 carbons, phenyl, phenyl substituted with one or two alkyl groups of 1 to 4 carbons, with F, Cl, Br, I, or with $CF_3$, or $R_5$ is a 5 or 6 membered heteroaryl having 1 to 3 heteroatoms selected from O, S, and N, and 5 or 6 membered heteroaryl having 1 to 3 heteroatoms selected from O, S, and N substituted with one or two alkyl groups of 1 to 4 carbons, with F, Cl, Br, I, or with $CF_3$;

$R_6$ is H, alkyl of 1 to 4 carbons, allyl, cycloalkyl of 3 to 6 carbons, phenyl, phenyl substituted with one or two alkyl groups of 1 to 4 carbons, with F, Cl, Br, I, or with $CF_3$, or $R_6$ is 5 or 6 membered heteroaryl having 1 to 3 heteroatoms selected from O, S, and N, or 5 or 6 membered heteroaryl having 1 to 3 heteroatoms selected from O, S, and N substituted with one or two alkyl groups of 1 to 4 carbons, with F, Cl, Br, I, or with $CF_3$;

$R_7$ is H, alkyl of 1 to 4 carbons, allyl, cycloalkyl of 3 to 6 carbons, phenyl, phenyl substituted with one or two alkyl groups of 1 to 4 carbons, with F, Cl, Br, I, or with $CF_3$;

$R_1$ and $R_2$ or $R_2$ and $R_3$ or $R_3$ and $R_4$ together can form a ring together with the respective carbons to which each of these is attached, the portion contributed by $R_1$ and $R_2$ or by $R_2$ and $R_3$ or by $R_3$ and $R_4$ having the formulas (i), (ii), (iii), (iv) or (v)

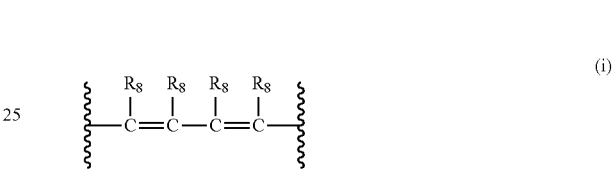

(i)

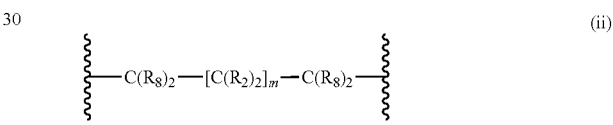

(ii)

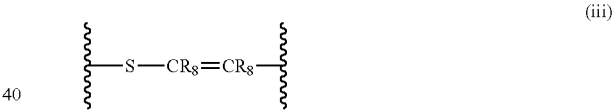

(iii)

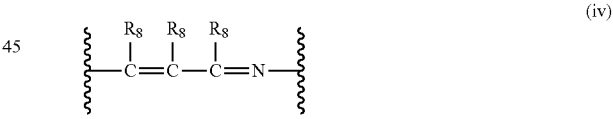

(iv)

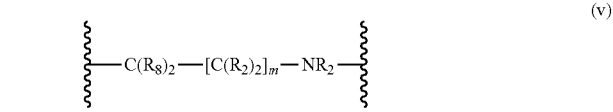

(v)

m is an integer having the values 0 to 3;

$R_8$ is independently H, alkyl of 1 to 6 carbons, alkenyl of 2 to 6 carbons, alkynyl of 2 to 6 carbons, $SO_3H$, $N_3$, CN, $NO_2$, F, Cl, Br, I, $CF_3$, $COR_9$, $CH_2OR_9$, $OR_{10}$; $SR_{10}$, $C_{1-6}$alkylamino, or $C_{1-6}$dialkylamino, $R_9$ is H, alkyl of 1 to 6 carbons, or $OR_{10}$, and $R_{10}$ independently is H or alkyl of 1 to 6 carbons.

In a second aspect the present invention is directed to pharmaceutical compositions containing as the active ingredient one or more compounds of Formula 1, the compositions being utilized as medicaments in mammals, including humans, for treatment of diseases and or alleviations of conditions which are responsive to treatment by agonists of alpha$_{2B}$ adrenergic receptors. The compositions containing the compounds of the invention are primarily, but not exclusively, used for alleviation of chronic pain and/or allodynia. The compounds where the X group is S (thiones) have the demonstrable advantageous property that they are specific or selective to alpha$_{2B}$ and/or alpha$_{2C}$ adrenergic receptors in preference over alpha$_{2A}$ adrenergic receptors, and as such have no or only minimal cardiovascular and/or sedatory activity. Compounds where the X group is O (oxo compounds) also have the advantageous property that they have no or only minimal cardiovascular and/or sedatory activity.

DETAILED DESCRIPTION OF THE INVENTION

A general description of the compounds of the invention is provided in the Summary section of the present application for patent with reference to Formula 1. It will be readily apparent to those skilled in the art that some of the compounds depicted in these formulas may exist in trans (E) and cis (Z) isomeric forms. Moreover, some of the compounds of the invention may contain one or more asymmetric centers, such that the compounds may exist in enantiomeric as well as in diastereomeric forms. Unless it is specifically noted otherwise, the scope of the present invention includes all trans (E) and cis (Z) isomers, enantiomers, diastereomers and racemic mixtures. Some of the compounds of the invention may form salts with pharmaceutically acceptable acid or base, and such pharmaceutically acceptable salts of the compounds of Formula 1 are also within the scope of the invention.

Both the imidazole-2-thione and the imidazol-2-one derivative compounds of the present invention can undergo tautomeric transformations and can be depicted by the tautomeric formulas shown below. All tautomers of Formula 1 are within the scope of the invention.

Generally speaking and referring to Formula 1 in the preferred compounds of the invention the variable p represent the integer zero (0) or one (1) and the R$_{10}$ groups of the moiety [C(R$_{10}$)$_2$]$_p$ are hydrogen. Thus, in the preferred compounds of the invention a methylene (CH$_2$) group connects the imidazole-2-thione or imidazol-2-one nucleus with the cycloalkyl or cycloalkenyl ring shown in Formula 1, or there is no such connecting group.

In the preferred compounds of the invention the variable n represents an integer having the values zero (0) or one (1) so that the cycloalkyl or cycloalkenyl ring shown in Formula 1 is preferably 5 or 6 membered.

The variables R$_1$, R$_2$, R$_3$, and R$_4$ of the preferred compounds of the invention represent hydrogen, alkyl of 1 to 4 carbons, an oxo group, and ethynyl. Alternatively in many preferred compounds of the invention two adjacent ones of the R$_1$, R$_2$, R$_3$, and R$_4$ groups form a 5 or 6 membered ring which can be aromatic, or fully or partly saturated but more preferably at least partly unsaturated. When the ring formed by two adjacent ones of the R$_1$, R$_2$, R$_3$, and R$_4$ groups is heteroaromatic then pyridyl, thienyl, furyl, pyrollyl and imidazole rings are preferred with the thienyl, pyridyl and piperidinyl being most preferred.

The variable R$_8$ represents the substituent on the ring formed by two adjacent ones of the R$_1$, R$_2$, R$_3$, and R$_4$ groups and is preferably H, alkyl of 1 to 4 carbons, OR$_9$, Cl, Br, F, or CH$_2$OH.

The presently most preferred 4-(substituted cycloalkylmethyl) imidazole-2-thione and 4-(substituted cycloalkenylmethyl) imidazole-2-thione compounds of the invention are disclosed by their structural formula in Table 1 together with their activity in assays measuring their ability to act as agonists of alpha$_{2A}$, alpha$_{2B}$ and alpha$_{2C}$ adrenergic receptors. The presently most preferred 4-(substituted cycloalkylmethyl) imidazol-2-one and 4-(substituted cycloalkenylmethyl) imidazol-2-one compounds of the invention are disclosed by their structural formula in Table 2.

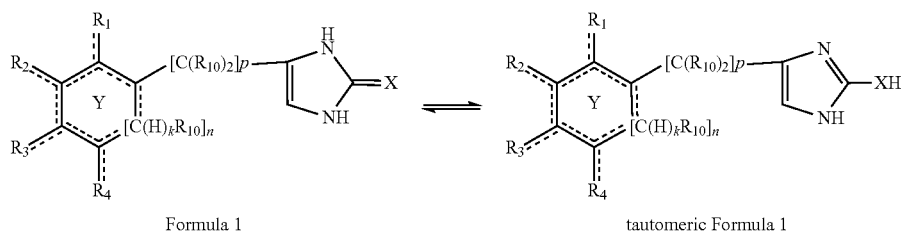

Formula 1                tautomeric Formula 1

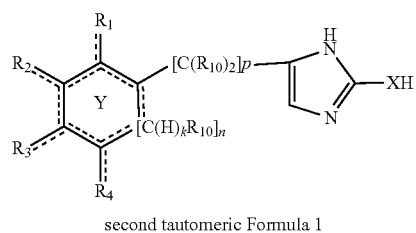

second tautomeric Formula 1

TABLE 1

| | (imidazole-2-thione compounds) | | |
|---|---|---|---|
| | | EC$_{50}$ (nM) (intrinsic activity) | |
| Compound # | Alpha 2A | Alpha 2B | Alpha 2C |
| Compound 2 | NA | 81 (0.81) | NA |
| Compound 3 | NA | 750 (0.49) | >2000 (0.32) |
| Compound 1 | NA | 5 (0.87) | 110 (0.43) |
| Compound 7 | NA | 10 (0.91) | 182 (0.57) |

TABLE 1-continued
(imidazole-2-thione compounds)
| Compound # | EC$_{50}$ (nM) (intrinsic activity) | | |
|---|---|---|---|
| | Alpha 2A | Alpha 2B | Alpha 2C |
| Compound 4 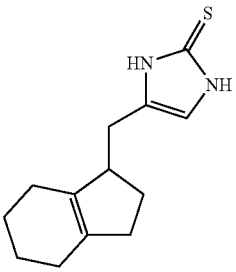 | NA | 30 (1.06) | 602 (0.55) |
| Compound 32 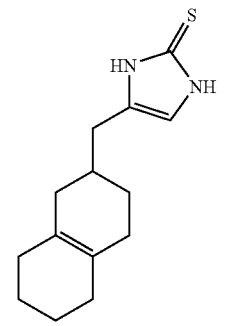 | NA | 86 (0.78) | NA |
| Compound 25 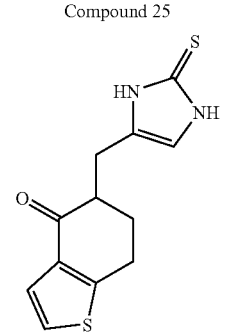 | NA | 106 (0.97) | NA |
| Compound 10 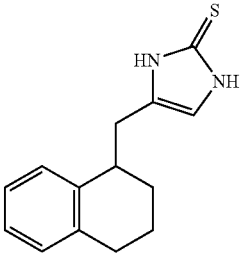 | NA | 24 (0.93) | 137 (0.42) |

TABLE 1-continued
(imidazole-2-thione compounds)
| Compound # | EC$_{50}$ (nM) (intrinsic activity) | | |
|---|---|---|---|
| | Alpha 2A | Alpha 2B | Alpha 2C |
| Compound 31 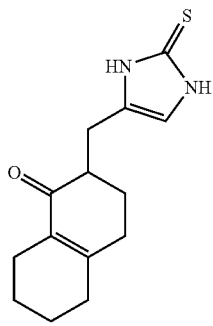 | NA | 815 (0.83) | NA |
| Compound 29 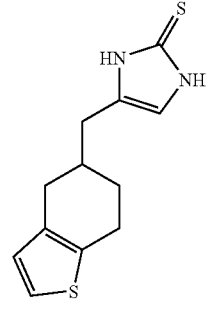 | NA | 14 (0.74) | NA |
| Compounds 23 and 24 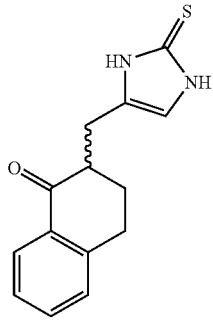 | NA | 18 (1.0) | NA |
| Compound 18 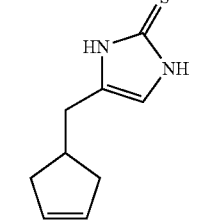 | NA | 24 (0.85) | 180 |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 5 | NA | 85 (1.07) | 677 (1.13) |
| Compound 6 | NA | 161 (1.0) | 331 (1.0) |
| Compound 8 | NA | 578 (1.1) | >2000 (0.57) |
| Compound 9 | NA | 33 (1.01) | 1022 (1.39) |
| Compound 19 | NA | 665 (1.12) | >2000 (0.70) |

TABLE 1-continued
| (imidazole-2-thione compounds) | | | |
|---|---|---|---|
| | EC$_{50}$ (nM) (intrinsic activity) | | |
| Compound # | Alpha 2A | Alpha 2B | Alpha 2C |
| Compound 11 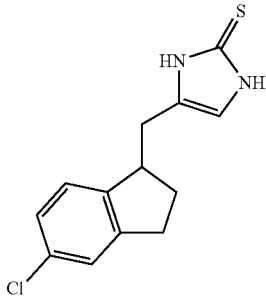 | NA | 1151 (0.37) | NA |
| Compound 12 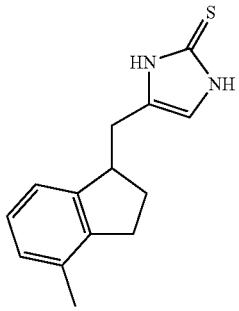 | NA | 58 (0.93) | 939 (0.34) |
| Compound 13 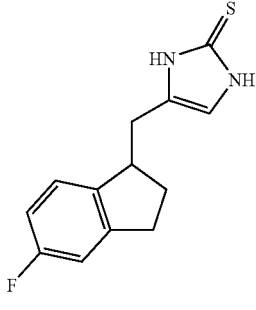 | NA | 41 (0.97) | 1113 (0.52) |
| Compound 36 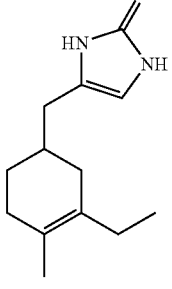 | NA | 6 (1.08) | NA |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 14 | NA | 1592 (0.68) | >2000 (0.46) |
| Compound 15 | NA | 158 (0.85) | 2000 (0.62) |
| Compound 16 | NA | 19 (0.92) | 349 (0.69) |
| Compound 17 | NA | 30 (0.94) | 139 (1.0) |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 20 | NA | 260 (1.0) | 662 (0.75) |
| Compound 21 | NA | 422 (1.11) | >2000 (0.57) |
| Compound 30 | NA | 17 (0.65) | NA |
| Compound 22 | NA | 1618 (0.88) | 2473 (0.72) |

TABLE 1-continued
(imidazole-2-thione compounds)
| Compound # | EC$_{50}$ (nM) (intrinsic activity) | | |
|---|---|---|---|
| | Alpha 2A | Alpha 2B | Alpha 2C |
| Compound 26 | NA | 523 (0.96) | >2000 (0.61) |
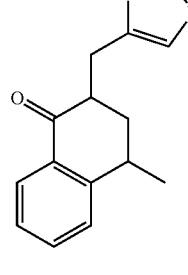
| Compound 27 | NA | 850 (0.71) | NA |
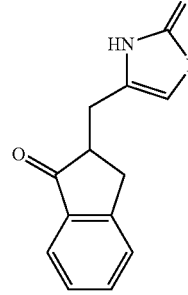
| Compound 37 | NA | 25 (0.61) | NA |
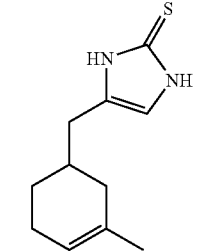
| Compound 28 | NA | 1008 (0.48) | NA |
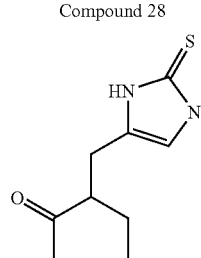

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 39 | NA | 451 (0.68) | NA |
| Compound 40 | NA | 265 (0.60) | NA |
| Compound 38 | NA | 61 (0.72) | NA |
| Compound 34 | NA | 29 (0.96) | 66 (0.47) |

TABLE 1-continued
(imidazole-2-thione compounds)
| Compound # | EC₅₀ (nM) (intrinsic activity) | | |
|---|---|---|---|
| | Alpha 2A | Alpha 2B | Alpha 2C |
| Compound 33 | NA | 162 (0.95) | 306 (0.34) |
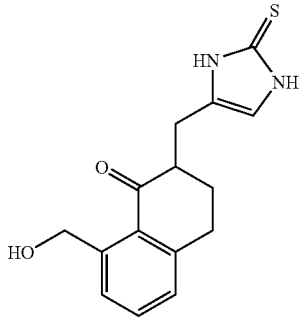
| | | | |
|---|---|---|---|
| Compound 35 | NA | 172 (0.76) | 107 (0.35) |
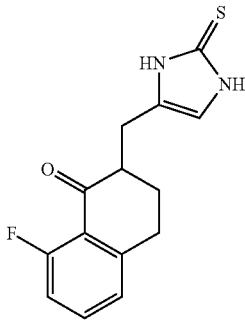
| | | | |
|---|---|---|---|
| Compound 23 | NA | 41 (0.83) | NA |
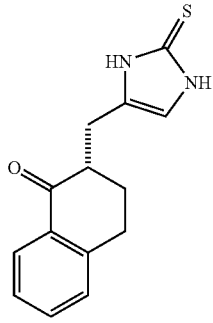
(-) enantiomer
| | | | |
|---|---|---|---|
| Compound 24 | NA | 92 (0.79) | NA |
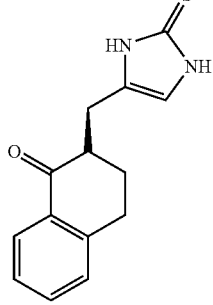
(+) enantiomer TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 100 (+) enantiomer | NA | 7.5 (0.95) | 64 (0.56) |
| Compound 101 (−) enantiomer | NA | 24.5 (0.97) | 629.5 (0.61) |
| Compound 102 | NA | 17 (0.82) | NA |
| Compound 103 | NA | 286 (1.16) | — |
| Compound 104 | NA | 28 (0.9) | 115.5 (0.55) |
| Compound 105 | NA | 27 (0.95) | 139 (0.48) |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 106 | NA | 755 (0.98) | 2258 (0.88) |
| Compound 107 | NA | 720 (0.6) | NA |
| Compound 108 (−) enantiomer | NA | 395 (0.41) | NA |
| Compound 109 (+) enantiomer | NA | 13.7 (0.93) | NA |
| Compound 110 (+) enantiomer | NA | 60 (0.73) | NA |
| Compound 111 | NA | 300 (0.76) | NA |
| Compound 141 | NA | 115 (0.99) | NA |

TABLE 1-continued
(imidazole-2-thione compounds)
| Compound # | EC$_{50}$ (nM) (intrinsic activity) | | |
|---|---|---|---|
| | Alpha 2A | Alpha 2B | Alpha 2C |
| Compound 142 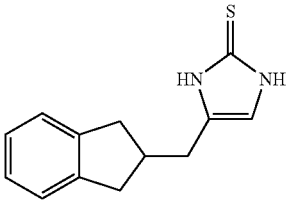 | NA | 110 (0.65) | NA |
| Compound 143 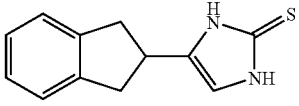 | NA | 6 (0.98) | NA |
| Compound 144 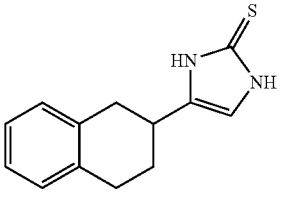 | NA | 34 (1.03) | 423.5 (0.52) |
| Compound 145 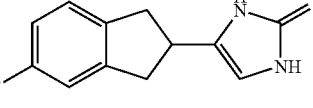 | NA | 30 (0.75) | NA |
| Compound 146 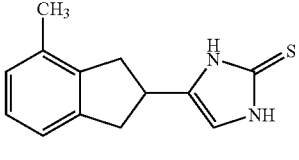 | NA | 3 (0.99) | 13 (0.99) |
| Compound 147 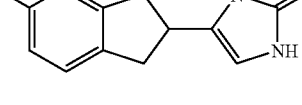 | NA | 27 (1.12) | 374 (0.45) |
| Compound 148 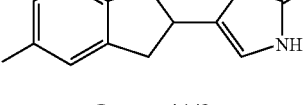 | NA | 28 (0.87) | 321 (0.38) |
| Compound 149 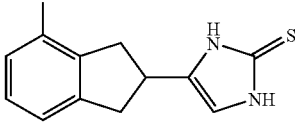 | NA | 5 (1.07) | 106 (0.87) |

TABLE 1-continued
(imidazole-2-thione compounds)
| Compound # | EC₅₀ (nM) (intrinsic activity) | | |
|---|---|---|---|
| | Alpha 2A | Alpha 2B | Alpha 2C |
| Compound 150 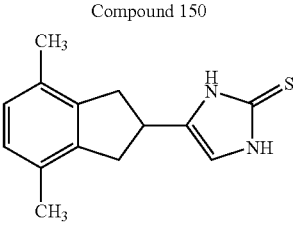 | NA | 7 (1.27) | 92 (0.86) |
| Compound 151 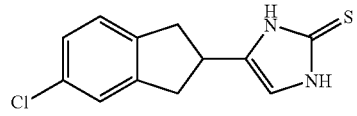 | NA | 57.5 (0.85) | NA |
| Compound 152 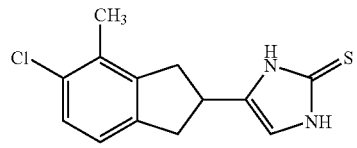 | NA | 14 (0.91) | 561 (0.45) |
| Compound 153 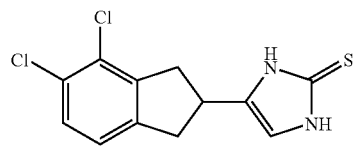 | NA | 7 (1) | 190 (0.53) |
| Compound 154 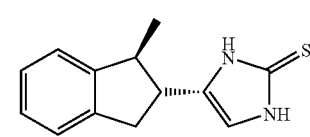 | NA | 5 (1.03) | NA |
| Compound 153 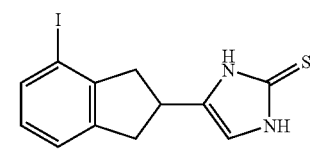 | NA | 7 (0.96) | 101 (0.49) |
| Compound 157 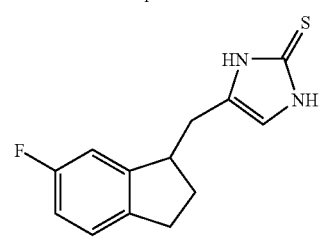 | NA | 34 (1.01) | 42 (0.63) |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 158 | NA | 354 (0.363) | 662 (0.38) |
| Compound 159 | NA | 34.5 (0.93) | NA |
| Compound 156 | NA | 834 (0.54) | NA |
| Compound 160 | NA | 105 (0.64) | NA |

TABLE 1-continued
(imidazole-2-thione compounds)
| Compound # | EC₅₀ (nM) (intrinsic activity) | | |
|---|---|---|---|
| | Alpha 2A | Alpha 2B | Alpha 2C |
| Compound 161 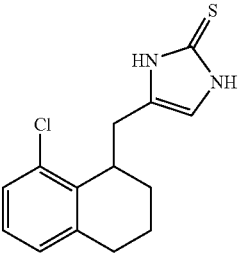 | NA | 74 (0.78) | NA |
| Compound 162 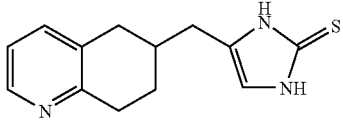 | NA | 1592 (0.74) | NA |
| Compound 163 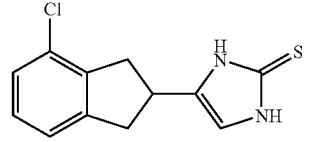 | NA | <2 (1.15) | 45 (0.74) |
| Compound 164 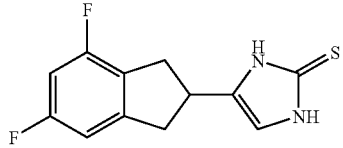 | NA | 6.5 (0.81) | NA |
| Compound 165 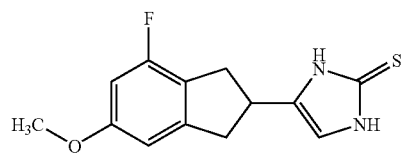 | NA | 22 (1.02) | NA |
| Compound 166 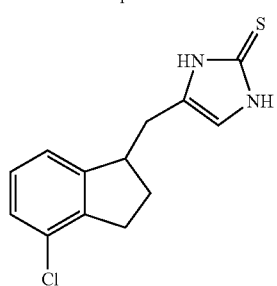 | NA | 31.3 (0.91) | NA |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 167 | NA | 87 (0.73) | 168 (0.59) |
| Compound 168 | NA | 236 (1.07) | 2821 (0.46) |
| Compound 169 | NA | 160 (0.94) | NA |
| Compound 170 | NA | 990 (0.5) | NA |
| Compound 171 | NA | 469 (0.87) | NA |
| Compound 112 | NA | NA | 214 (0.68) |

TABLE 1-continued
(imidazole-2-thione compounds)
| Compound # | EC$_{50}$ (nM) (intrinsic activity) | | |
|---|---|---|---|
| | Alpha 2A | Alpha 2B | Alpha 2C |
| Compound 113 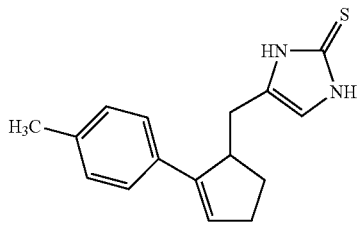 | NA | 2178 (0.47) | >3000 (0.46) |
| Compound 114 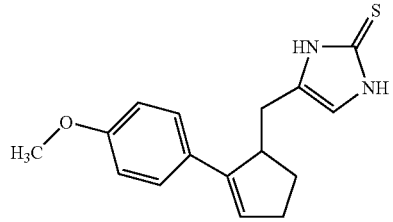 | NA | >3000 (0.56) | 568 (0.47) |
| Compound 115 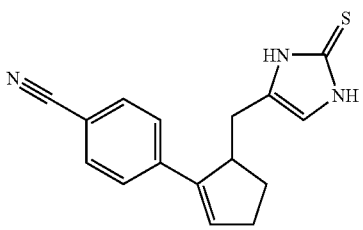 | NA | 498 (0.91) | 155 (1.01) |
| Compound 116 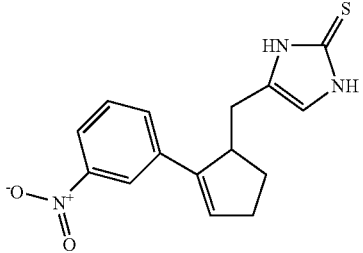 | NA | >10000 (0.63) | 2508 (0.61) |
| Compound 129 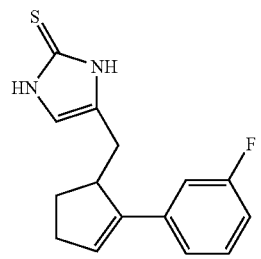 | NA | NA | 190.5 (0.45) |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 117 (+) enantiomer | NA | 190.5 (0.53) | 916 (0.37) |
| Compound 118 (+) enantiomer | NA | NA | 715.3 (0.61) |
| Compound 119 (+) enantiomer | NA | 471.7 (0.83) | 790.5 (0.58) |
| Compound 120 (-) enantiomer | NA | 1471 (0.66) | NA |
| Compound 121 (-) enantiomer | NA | 269 (0.97) | 131 (0.72) |

TABLE 1-continued
| (imidazole-2-thione compounds) | | | |
|---|---|---|---|
| | | $EC_{50}$ (nM) (intrinsic activity) | |
| Compound # | Alpha 2A | Alpha 2B | Alpha 2C |
| Compound 122 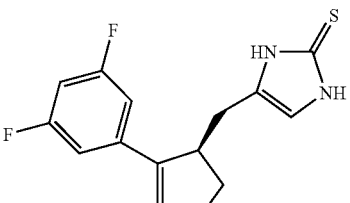 (−) enantiomer | NA | 1599 (0.59) | 569 (0.68) |
| Compound 123 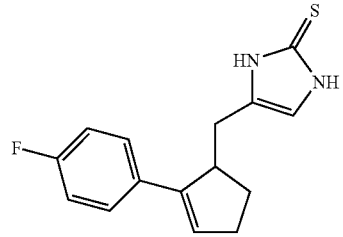 | NA | 458.7 (0.68) | 151.5 (0.77) |
| Compound 124 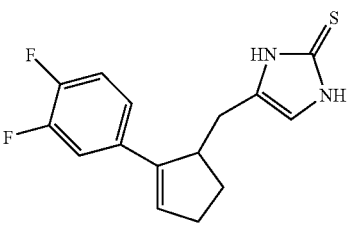 | NA | 225 (0.44) | 205 (0.68) |
| Compound 125 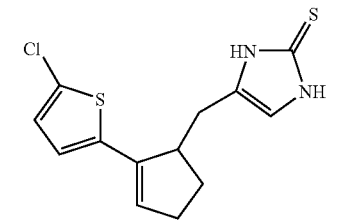 | NA | 1095 (0.69) | 2764 (0.75) |
| Compound 126 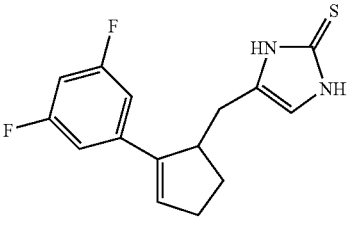 | NA | NA | 240.8 (0.66) |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 127 | NA | NA | 994 (0.53) |
| Compound 128 | NA | 219 (0.42) | 289.5 (0.62) |
| Compound 130 | NA | NA | 429.5 (0.38) |
| Compound 131 | NA | 234 (0.53) | 611 (0.42) |
| Compound 132 | NA | 103 (0.97) | 40 (0.52) |

TABLE 1-continued

(imidazole-2-thione compounds)

| Compound # | EC₅₀ (nM) (intrinsic activity) | | |
|---|---|---|---|
| | Alpha 2A | Alpha 2B | Alpha 2C |
| Compound 133 | NA | 603 (0.98) | 57 (0.5) |
| Compound 134 | NA | 269 (0.79) | NA |
| Compound 135 | NA | 32 (0.9) | 9 (0.45) |
| Compound 136 | NA | 22.5 (0.97) | 34.5 (0.82) |

TABLE 1-continued (imidazole-2-thione compounds)

| Compound # | EC$_{50}$ (nM) (intrinsic activity) | | |
|---|---|---|---|
| | Alpha 2A | Alpha 2B | Alpha 2C |
| Compound 137 | NA | 22 (0.93) | 41 (0.85) |
| Compound 138 | NA | 21 (1.08) | 92 (0.51) |
| Compound 139 | NA | 115 (0.89) | 47 (1.11) |
| Compound 140 | NA | 51 (0.78) | 22 (0.95) |

TABLE 2
(imidazol-2-one compounds)
Compound #
Compound 41
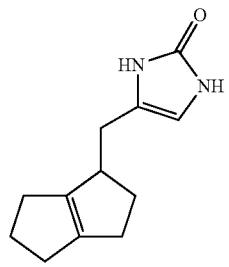
Compound 42
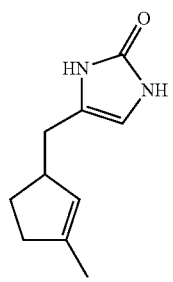
Compound 45
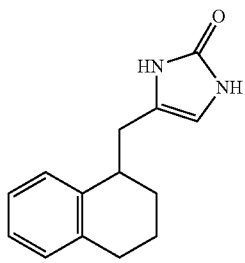
Compound 44
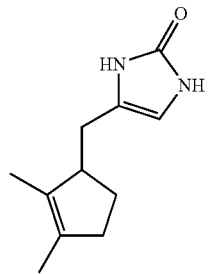
Compound 46
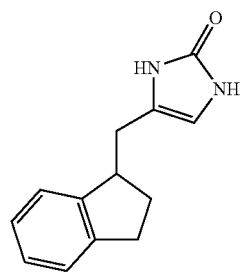
TABLE 2-continued
(imidazol-2-one compounds)
Compound #
Compound 54
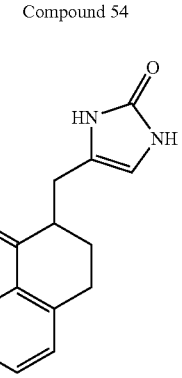
Compound 55
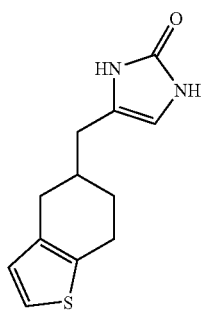
Compound 47
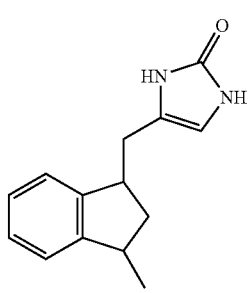
Compound 48
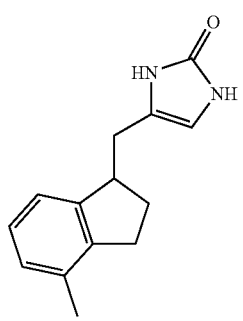

TABLE 2-continued
(imidazol-2-one compounds)
Compound #
Compound 49
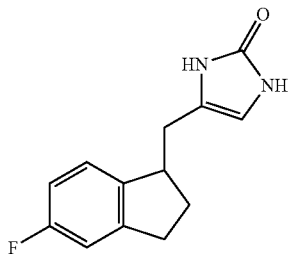
Compound 59
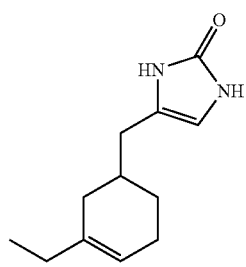
Compound 58
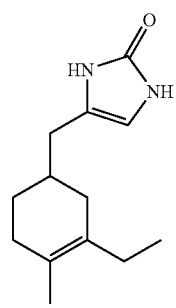
Compound 57
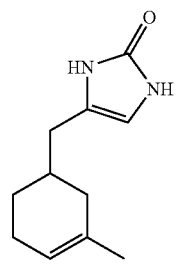
Compound 50
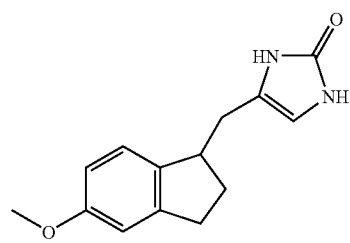
TABLE 2-continued
(imidazol-2-one compounds)
Compound #
Compound 51
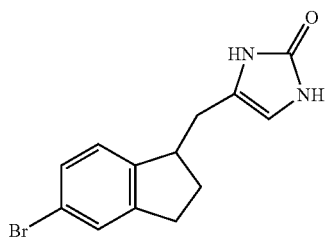
Compound 56
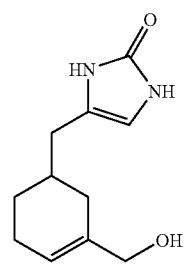
Compound 43
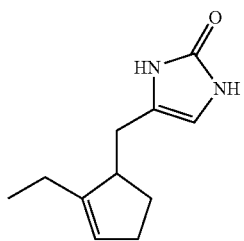
Compound 52
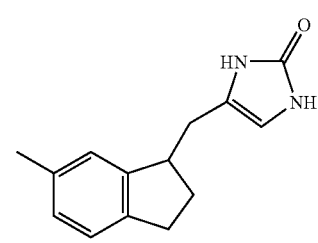
Compound 53
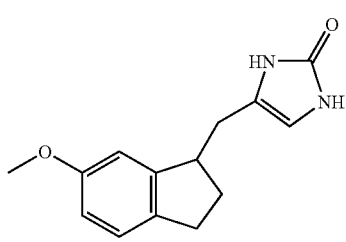

TABLE 2-continued (imidazol-2-one compounds)
Compound #

Compound 64

Compound 60

Compound 63

Compound 61

Compound 62

Reaction Scheme A illustrates a general method for obtaining the 4-(substituted cycloalkylmethyl) imidazole-2-thione and 4-(substituted cycloalkenylmethyl) imidazole-2-thione compounds of the invention. The starting material in this scheme is a primary alcohol of Formula 2 where the variables have the same definitions as in Formula 1. However the scheme is primarily applicable when one of the $R_1$ and $R_2$ substituents is not H. Thus, the compound of Formula 2 has one $C(R_{10})_2$ unit less than the compound of Formula 1 in the corresponding chain. However, for simplicity of illustration the scheme discloses the preparation of the preferred class of 4-(substituted cycloalkylmethyl) imidazole-2-thione and 4-(substituted cycloalkenylmethyl) imidazole-2-thione compounds of the invention where p is one (1) and $R_{10}$ is hydrogen, and the starting material shown in the scheme is designated with Formula 2A. The compounds of Formula 2 and of Formula 2A can be obtained in accordance with known procedures in the chemical scientific and patent literature or by such modifications of known procedures which are readily apparent to the practicing synthetic organic chemist.

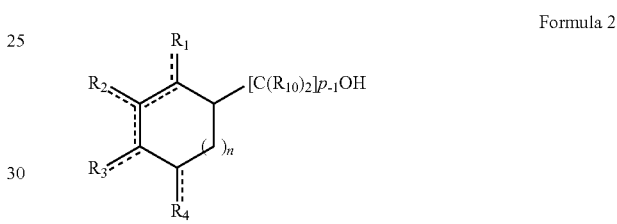

Formula 2

Referring still to Reaction Scheme A the primary cyclic alcohol of Formula 2A is reacted with ethyl vinyl ether (EVE) in the presence of mercuric ions (mercuric acetate $Hg(OAc)_2$) to provide the vinyl ether of Formula 3 which is thereafter oxidized and rearranged by treatment with lithium perchlorate ($LiClO_4$) to provide the 4-(substituted cycloalkyl)-acetaldehydes or 4-(substituted cycloalkenyl)-acetaldehydes of Formula 4. The aldehydes of Formula 4 are then reacted with para-toluenesulfonyl isocyanide (tosylmethylisocyanide, TosMIC), sodium cyanide (NaCN) and thereafter heated with ammonia in an alcohol solvent to provide the 4-(substituted cycloalkylmethyl) imidazole or 4-(substituted cycloalkenylmethyl) imidazole compounds of Formula 5 which are preferably isolated as the fumarate salt. The 4-(substituted cycloalkylmethyl) imidazole or 4-(substituted cycloalkenylmethyl) imidazole compounds of Formula 5 are then reacted with phenylchlorothionoformate (PhOC(S)Cl) to convert them to the corresponding imidazole-2-thione compounds of Formula 6. The compounds of Formula 6 are pharmaceutically active compounds of the invention and are within the scope of Formula 1.

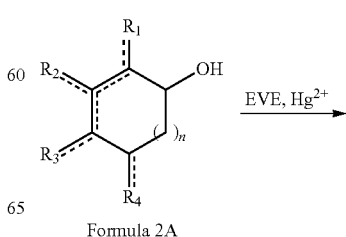

Formula 2A

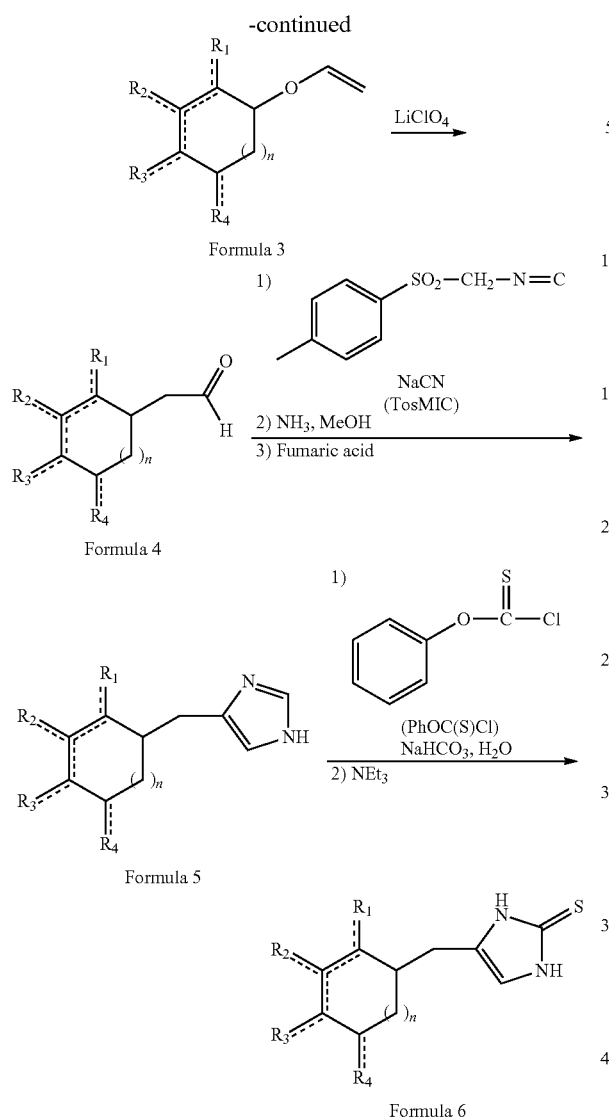

Formula 3

Formula 4

Formula 5

Formula 6

Reaction Scheme A

Reaction Scheme B discloses another general synthetic routes to 4-(substituted cycloalkylmethyl) imidazole-2-thiones and 4-(substituted cycloalkenylmethyl) imidazole-2-thione compounds of the invention. This synthetic route is particularly suitable for preparation of those compounds of the invention where the $R_1$ substituent of Formula 1 represents an oxo group, and where a suitably substituted cycloalkyl or cycloalkenyl group of Formula 7 is readily available commercially or in accordance with the chemical literature. In accordance with this scheme, the keto compound of Formula 7 is heated with 4,5-imidazole carboxaldehyde of Formula 8 in the presence of strong acid to yield (1H-imidazol-4-yl-methylene)-cycloalkyl or (1H-imidazol-4-yl-methylene)-cycloalkenyl derivatives of Formula 9. 4,5-imidazole carboxaldehyde is available from Aldrich. The methylene group of the imidazole compound of Formula 9 is reduced by hydrogenation to provide (1H-imidazol-4-yl-methyl)-cycloalkyl or (1H-imidazol-4-yl-methyl)-cycloalkenyl derivatives of Formula 10. The (1H-imidazol-4-yl-methyl)-cycloalkyl or (1H-imidazol-4-yl-methyl)-cycloalkenyl derivatives of Formula 10 are reacted with phenylchlorothionoformate (PhOC(S)Cl), as described above in connection with Reaction Scheme A, to obtain the thione compounds of Formula 11. The compounds of Formula 11 are pharmaceutically active compounds of the invention and are within the scope of Formula 1.

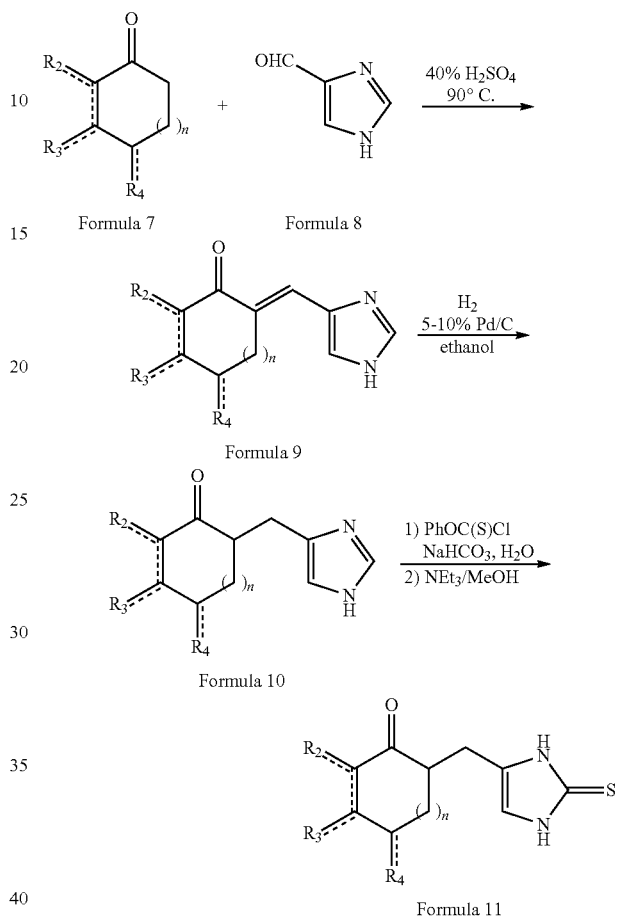

Formula 7

Formula 8

Formula 9

Formula 10

Formula 11

Reaction Scheme B

Reaction Scheme C discloses still another general synthetic route to the preparation of the 4-(substituted cycloalkylmethyl) imidazole-2-thione and 4-(substituted cycloalkenylmethyl) imidazole-2-thione compounds of the invention. This synthetic route is particularly suitable for preparation of those compounds of the invention where a corresponding, suitably substituted cycloalkyl or cycloalkenyl methyl iodo (or chloro or bromo) compound of Formula 12 is available commercially or in accordance with the chemical literature to serve as a starting material. The iodo compound is reacted with 1-N-(dimethylsulfamoyl)-2-tert-butyldimethylsilyl imidazole of Formula 13 in the presence of n-butyl lithium to give 4-(substituted cycloalkylmethyl or 4-(substituted cycloalkenylmethyl 1-N-(dimethylsulfamoyl)-2-tert-butyldimethylsilyl imidazole of Formula 14. The synthesis of 1-N-(dimethylsulfamoyl)-2-tert-butyldimethylsilyl imidazole is described below in the experimental section of the present application for patent. The tertiary butyldimethylsilyl (TBS) group is removed from the compound of Formula 14 by treatment with tetrabutylammonium fluoride (TBAF) to give 4-(substituted cycloalkylmethyl or 4-(substituted cycloalkenylmethyl 1-N-(dimethylsulfamoyl)-imidazole compounds of Formula 15. Treatment of the 4-(substituted cycloalkylmethyl or 4-(substituted cycloalkenylmethyl 1-N-

(dimethylsulfamoyl)-imidazole compounds of Formula 15 with strong base, such as potassium hydroxide removes the N-(dimethylsulfamoyl) group and the resulting 4-(substituted cycloalkylmethyl or 4-(substituted cycloalkenylmethyl-imidazole compounds of Formula 5 are isolated as the fumarate salt. The 4-(substituted cycloalkylmethyl or 4-(substituted cycloalkenylmethyl-imidazole compounds of Formula 5 are then reacted with phenylchlorothionoformate (PhOC(S)Cl) to convert them to the corresponding imidazole-2-thione compounds of Formula 6, as is described in connection with Reaction Scheme A.

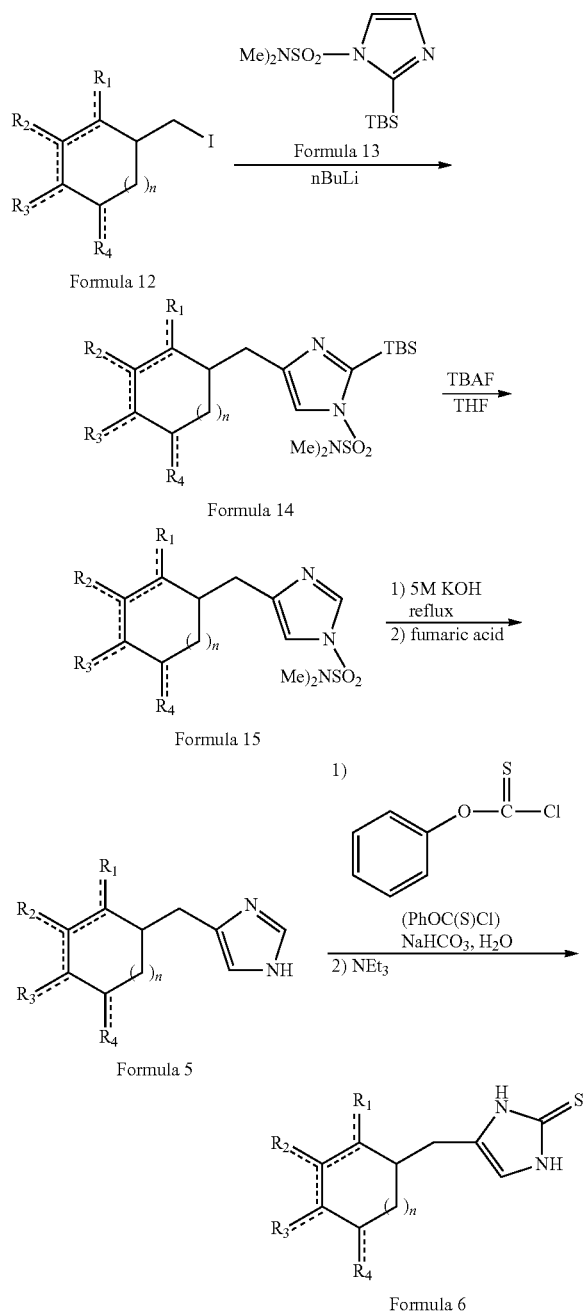

Reaction Scheme C

Reaction Scheme D illustrates a general method for obtaining the 4-(substituted cycloalkylmethyl) imidazol-2-one and 4-(substituted cycloalkenylmethyl) imidazole-2-one compounds of the invention. The actual starting material in this scheme can also be the primary alcohol of Formula 2 which is shown in Reaction Scheme A, where the variables have the same definitions as in Formula 1. Thus, the compound of Formula 2 has one $C(R_{10})_2$ unit less than the compound of Formula 1 in the corresponding chain. However, for simplicity of illustration the scheme discloses the preparation of the preferred class of 4-(substituted cycloalkylmethyl) imidazol-2-one and 4-(substituted cycloalkenylmethyl) imidazol-2-one compounds of the invention where p is one (1) and $R_{10}$ is hydrogen. Because certain initial reaction steps followed in this scheme are the same as in Reaction Scheme A, this Scheme D illustrates the synthesis only from the compound of Formula 5, which is obtained as described in Scheme A. Thus the compounds of Formula 5, preferably in the form of the fumarate salt, are reacted with phenylchloroformate (PhOC(O)Cl) in the presence of sodium bicarbonate, followed by reaction with sodium carbonate to convert them to the corresponding imidazol-2-one compounds of Formula 16. The compounds of Formula 16 are pharmaceutically active compounds of the invention and are within the scope of Formula 1.

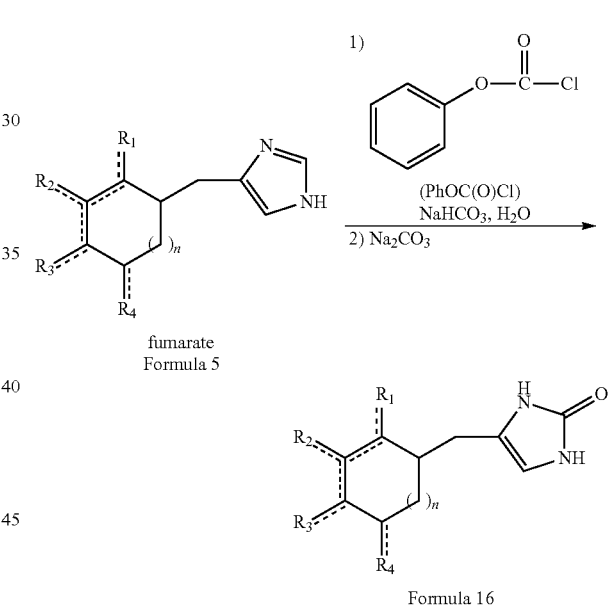

Reaction Scheme D

Reaction Scheme E discloses another general synthetic routes to 4-(substituted cycloalkylmethyl) imidazol-2-ones and 4-(substituted cycloalkenylmethyl) imidazol-2-one compounds of the invention. Similarly to Reaction Scheme B this synthetic route is particularly suitable for preparation of those compounds of the invention where the $R_1$ substituent of Formula 1 represents an oxo group, and where a suitably substituted cycloalkyl or cycloalkenyl group of Formula 7 as shown in Reaction Scheme B is readily available commercially or in accordance with the chemical literature. In the reaction sequence disclosed in this scheme the compounds of Formula 10, obtained as shown in Reaction Scheme B, are reacted with phenylchloroformate (PhOC(O)Cl) in the presence of sodium bicarbonate; followed by reaction with sodium carbonate to convert them to the corresponding imidazol-2-one compounds of Formula 16.

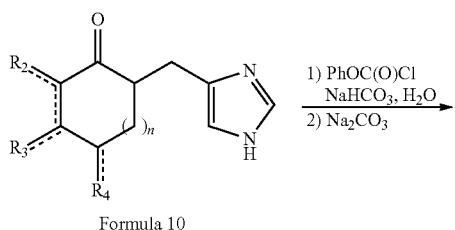

Formula 10

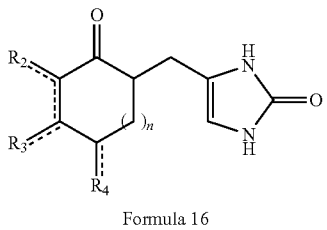

Formula 16

Reaction Scheme E

Another general presently preferred synthetic route shown in Reaction Scheme F for the synthesis of the 4-(substituted cycloalkylmethyl) imidazol-2-one and 4-(substituted cycloalkenylmethyl) imidazol-2-one compounds of the invention is particularly suitable for preparation of those compounds of the invention where a corresponding, suitably substituted cycloalkyl or cycloalkenyl methyl iodo (or chloro or bromo) compound of Formula 12, shown in Reaction Scheme C, is available commercially or in accordance with the chemical literature to serve as a starting material. This synthetic route follows the route shown in Reaction Scheme C to prepare the imidazole compounds of Formula 15, as shown in Scheme C. These are thereafter converted to the corresponding cycloalkylmethyl) imidazol-2-one or 4-(substituted cycloalkenylmethyl) imidazol-2-one compounds by reactions with phenylchloroformate (PhOC(O)Cl) in the presence of sodium bicarbonate, followed by reaction with sodium carbonate to yield the corresponding imidazol-2-one compounds of Formula 16.

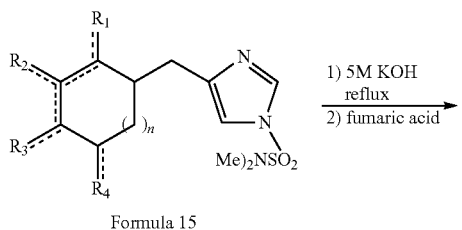

Formula 15

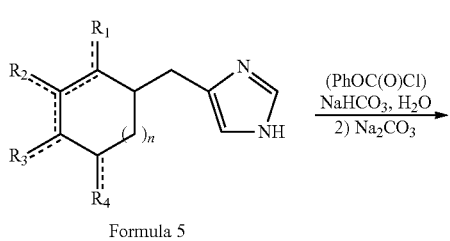

Formula 5

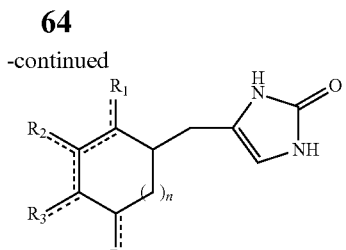

Formula 16

Reaction Scheme F

The reaction schemes incorporated in the experimental section of this application illustrate the synthetic schemes which are employed for the synthesis of preferred embodiments of compounds of the invention.

Biological Activity, Modes of Administration

The imidazole-2-thione compounds of the invention are agonists of alpha$_2$ adrenergic receptors, particularly they tend to be specific or selective agonists of alpha$_{2B}$ and/or to a lesser extent alpha$_{2C}$ adrenergic receptors, in preference over alpha$_{2A}$ adrenergic receptors. The specific or selective alpha$_{2B}$ and/or to a lesser extent alpha$_{2C}$ agonist activity of the compounds of the invention is demonstrated in an assay titled Receptor Selection and Amplification technology (RSAT) assay, which is described in the publication by Messier et. Al., 1995, Pharmacol. Toxicol. 76, pp. 308-311 (incorporated herein by reference) and is also described below. Another reference pertinent to this assay is Conklin et al. (1993) Nature 363:274-6, also incorporated herein by reference.

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to G$_i$, activate the RSAT response when coexpressed with a hybrid Gq protein that has a G$_i$ receptor recognition domain, called Gq/i5.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μL of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The EC$_{50}$ and maximal effect of each drug at each alpha$_2$ receptor is determined. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors.

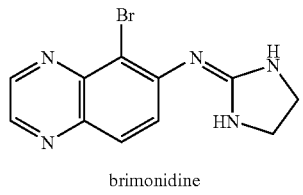

brimonidine

Diseases that may be treated with this invention include, but are not limited to: <
MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration,
UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White. Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy
VASUCLAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal. Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease
TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy
PROLIFERATIVE DISORDERS Proliferative Vitreal Retinopathy and Epiretinal Membranes
INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis
GENETIC DISORDERS Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum
RETINAL TEARS/HOLES Retinal Detachment, Macular Hole, Giant Retinal Tear
TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The results of the RSAT assay with several exemplary compounds of the invention are disclosed in Table 1 above together with the chemical formulas of these exemplary compounds. Each number in the table represents EC$_{50}$ in nanomolar (nM) concentration whereas the number in parenthesis in the table shows the fraction of activity of the appropriate standard which is attained by the tested compound. NA stands for "not active" at concentrations less than 10 micromolar. As is known EC$_{50}$ is the concentration at which half of a given compound's maximal activity is observed.

Generally speaking alpha2 agonists, can alleviate sympathetically-sensitized conditions that are typically associated with periods of stress. These include 1) the increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha2 agonists including alpha2B/2C agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of alpha$_{2B}$ and/or alpha$_{2C}$ adrenergic receptors in preference over alpha$_2$A receptors, if the compound is at least ten (10) times more active towards either alpha$_{2B}$ or towards alpha$_{2C}$ receptors than towards alpha$_{2A}$ receptors. It can be seen from these tables that the compounds of the invention are specific or selective agonists of alpha$_{2B}$ and/or alpha$_{2C}$ adrenergic receptors within the former definition, and in fact have no agonist like activity or only insignificant agonist-like activity on alpha$_{2A}$ receptors.

Thus, the imidazole-2-thione compounds of the invention are useful for treating conditions and diseases which are responsive to treatment by alpha$_{2B}$ and/or alpha$_{2C}$ adrenergic receptor agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds of this invention are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel disease (IBD), functional dyspepsia and ulcerative colitis. Surprisingly, although the selective alpha$_{2B}$ or alpha$_{2C}$ adrenergic receptor agonist activity of the imidazole-2-one compounds cannot be demonstrated in the RSAT assay, these compounds also are useful for treating the same conditions.

The activity of the compounds of the invention is highly advantageous because the administration of these compounds to mammals does not result in sedation or in significant cardiovascular effects (such as changes in blood pressure or heart rate).

The compounds of the invention act and can be used as a highly effective analgesic, particularly in chronic pain models, with minimal undesirable side effects, such as sedation and cardiovascular depression, commonly seen with other agonists of the $\alpha_2$ receptors.

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the invention is drawn to therapeutic compositions comprising the compounds of Formula 1 and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more compounds of Formula 1 or pharmaceutically acceptable salts thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (A$\beta$ and A$\delta$ fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A$\beta$ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

The following in vivo assays can be employed to demonstrate the biological activity of the compounds of the invention.

Sedative Activity

To test sedation, six male Sprague-Dawley rats are given up to 3 mg/kg of the test compound in a saline or DMSO vehicle by intraperitoneal injection (i.p.). Sedation is graded 30 minutes following administration of the drug by monitoring locomotor skills as follows.

The Sprague-Dawley rats are weighed and 1 ml/kg body weight of an appropriate concentration (i.e. 3 mg/ml for a final dose of 3 mg/kg) drug solution is injected intraperitoneally. Typically the test compound is formulated in approximately 10 to 50% DMSO. The results are compared to controls that are injected with 1 ml/kg saline or 10 to 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation.

Representative Compounds 18, 23, 49 and 61 of the invention were tested in this assay intraperitoneally and up to a dose of 1 mg/kg, and were found to have no sedative effect. The results in this test with other compounds of the invention are also expected to show that the compounds of the invention have no significant sedatory activity.

Effects on Cardiovascular System

To test the effect of the compounds on the cardiovascular system, typically six cynomolgus monkeys are given 500 µg/kg of the test compound by intravenous injection (i.v.) Or 3 mg/kg by oral gavage. The effects of the compound on the animals' blood pressure and heart rate is measured at time intervals from 30 minutes to six hours following administration of the drug. The peak change from a baseline measurement taken 30 minutes before drug administration is recorded using a blood pressure cuff modified for use on monkeys.

Specifically and typically the monkeys are weighed (approximately 4 kg) and an appropriate volume (0.1 ml/kg) of a 5 mg/ml solution of the test compound formulated in 10 to 50% DMSO is injected into the cephalic vein in the animals' arm. Cardiovascular measurements are made with a BP 100S automated sphygmomanometer (Nippon Colin, Japan) at 0.5, 1, 2, 4 and 6 hours.

The results of this test show that the compounds of the invention have no or only minimal detectable effect on the cardiovascular system.

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183-191 (1997) and Hargreaves, K. et al., *Pain* 32:77-88 (1988), hereby incorporated by reference herein.

In a variation of this latter model, male Sprague-Dawley rats are tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after, 20 seconds to prevent tissue damage.

Typically four test animals per group are weighed (approximately 0.3 kg) and injected intraperitonealy (i.p.) with 1 ml/kg of the test compound formulated in approximately 10 to 50% dimethylsulfoxide (DMSO) vehicle. Animals typically receive a 0.1 mg/kg and a 1 mg/kg dose of the three compounds. Rats are acclimated to the test chamber for about 15 minutes prior to testing. The paw withdrawal latency is measured at 30, 60 and 120 minutes after drug administration. The right and left paws are tested 1 minute apart, and the response latencies for each paw are averaged. Stimulus intensity is sufficient to provide a temperature of 45-50 degrees centigrade to each rat hindpaw.

The results in this test are expected to show that the compounds of the invention do not provide analgesic effects in this bioassay of acute pain.

Alleviation of Chronic Pain

A model in accordance with Kim and Chung 1992, Pain 150, pp 355-363 (Chung model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in approximately 10 to 50% DMSO and given in a volume of 1 ml/kg body weight.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol; Toxicol.* 20:441-462 (1980). The post-drug threshold is compared to the pre-drug threshold and the percent reversal of tactile sensitivity is calculated based on a normal threshold of 15.1 grams. The results are expressed in percent (%) MPE, where the MPE value reflects the percentage reversal of pain threshold to that of a normal animal (100%). Table 3 below indicates results of this test with Compounds 1, 7 and 29 of the invention, administered i.p. and in oral doses. The doses and the observed MPE values (±SEM) are shown in the table.

The results shown in Table 3 illustrate that these compounds of the invention significantly alleviate allodynic pain, and based on these test and/or on the compounds ability to activate $alpha_{2B}$ and/or $alpha_{2C}$ adrenergic receptors in preference over $alpha_{2A}$ adrenergic receptors, the compounds of the invention are expected to be useful as analgesics to alleviate allodynia and chronic pain.

SPECIFIC EMBODIMENTS, EXPERIMENTAL

Example A

Method A: Procedure for the preparation 4-(1,2,3,4,5,6-hexahydro-pentallen-1-ylmethyl)-1,3-dihydro imidazole-2-thione (Compound 1)

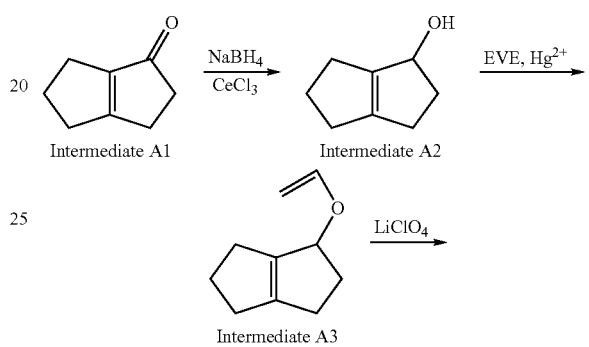

TABLE 3

Activity of Compounds in Chung Model of Neuropathic Pain (% Pain Reversal ± SEM)

| | Dose and Route of Administration | | | | | | |
|---|---|---|---|---|---|---|---|
| Compd. | 1 μg/kg i.p. | 3 μg/kg i.p. | 10 μg/kg i.p. | 30 μg/kg i.p. | 100 μg/kg i.p. | 300 μg/kg i.p. | 1000 μg/kg i.p. |
| 7 | 1 ± 1 | 23 ± 4 | 58 ± 8* | 85 ± 6* | 89 ± 7* | | |
| 29 | | | 17 ± 3 | 61 ± 11* | 14 ± 2 | | |
| 1 | | | | 9 ± 2 | 13 ± 2 | | 44 ± 7* |
| 41 | | | 3 ± 1.6 | 71 ± 2.8* | 13 ± 1* | | |
| 44 | 0.5 ± 2.9 | 24 ± 4.6* | 46 ± 9.1* | 62 ± 9.6* | 82 ± 5.8* | | |
| 49 | 2.3 ± 1.3 | 23 ± 3.8* | 39 ± 7.7* | 72 ± 8.2* | 80 ± 6.5* | | |
| 18 | | | 5 ± 2.5 | 35 ± 5.2* | 72 ± 6.6* | 71 ± 6.4* | |
| 23 & 24 | 0.8 ± 1.9 | 44 ± 6.3* | 69 ± 15* | 65 ± 11* | 80 ± 9.4* | 81 ± 10* | |
| 23 | 0.7 ± 0.8* | 59 ± 5.8* | 74 ± 6.1* | 69 ± 10* | | | |

| | Dose and Route of Administration | | | | |
|---|---|---|---|---|---|
| Compd. | 10 μg/kg p.o. | 30 μg/kg p.o. | 100 μg/kg p.o. | 300 μg/kg p.o. | 1000 μg/kg p.o. |
| 7 | 1 ± 1 | 56 ± 10* | 58 ± 8* | 61 ± 6* | |
| 1 | | 29 ± 5* | | | |
| 18 | | 1 ± 2 | 68 ± 4.4* | 82 ± 5.9* | 82 ± 8.1* |
| 23 & 24 | 2 ± 0.6 | 81 ± 8.2* | 87 ± 6.1* | 96 ± 4.5* | |
| 49 | | 43 ± 7.1* | 68 ± 4.8* | 74 ± 6.8* | |

All measurements 30 min following drug administration.
*p value < 0.001 compared to pretreatment values.

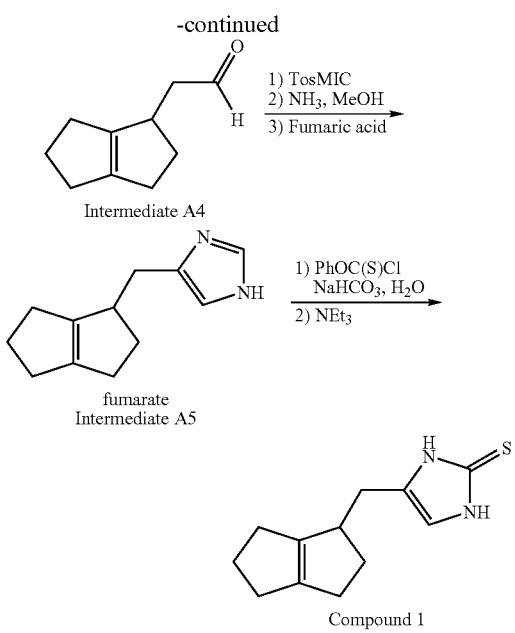

A solution of 3,4,5,6-tetrahydro-2H-pentalen-1-one (Intermediate A1) (prepared in accordance with Cooke et al. *J. Org. Chem.* 1980, 45, 1046, incorporated herein by reference) (1.5 g, 12.3 mmol) in MeOH (30 mL) and $CeCl_3 \cdot 7H_2O$ (3.6 g, 14.6 mmol) at 0° C. was treated with $NaBH_4$ (494 mg, 14.6 mmol). The solution was allowed to warm to rt and stirring was continued for 30 min. Water (100 mL) and diethyl ether (150 mL) were added. The organic layer was dried over $MgSO_4$, filtered and evaporated to dryness. The alcohol (Intermediate A2) was used in the next step without further purification.

A solution of the alcohol (Intermediate A2) (0.85 g, 6.9 mmol) in ethyl vinyl ether (50 mL) at rt was treated with $Hg(OAc)_2$ (1.75 g, 5.5 mmol) at rt for 18 h. The mixture was quenched with 5-10% KOH solution (80 mL) and the product was extracted with 50% ether:hexane (3×80 mL) and dried over $MgSO_4$. The organic layer was filtered and evaporated under vacuum. The crude vinyl ether (Intermediate A3) was used directly in the next step.

A solution of 4M $LiClO_4$ in ether (15 mL) was treated with the crude vinyl ether (Intermediate A3) (~0.90 g). The mixture was allowed to stir for 20-30 min. at rt. The reaction mixture was poured into water and extracted with ether (3×75 mL). The organic layers were combined, dried over $MgSO_4$ and evaporated to give the crude aldehyde (Intermediate A4).

The following preparation followed the procedure by Horne et al. Heterocycles, 1994, 39, 139, incorporated herein by reference. A solution of the aldehyde (Intermediate A24) (0.85 g, 5.6 mmol) in EtOH (15 mL) was treated with tosylmethyl isocyanide (TosMIC available from Aldrich, 1.1 g, 5.6 mmol) and NaCN (~15 mg, cat). This mixture was allowed to stir at rt for 20 min. The solvent was removed in vacuo and the residue was dissolved in ~7M $NH_3$ in MeOH and transferred to a resealable tube. This mixture was heated to at 100° C. for 15 h. The mixture was concentrated and purified by chromatography on $SiO_2$ with 5% MeOH (sat. w/$NH_3$):$CH_2Cl_2$. The imidazole was purified further as the fumarate salt (Intermediate A25).

A solution of 4-(1,2,3,4,5,6-hexahydro-pentalen-1-ylmethyl)-1H-imidazole; fumarate salt (Intermediate A25) (160 mg, 0.5 mmol) in THF (3 mL) and water (3 mL) was treated with $NaHCO_3$ (420 mg, 5 mmol) at rt for 20 min. Phenylchloro thionoformate (available from Aldrich, 180 μL, 1.3 mmol) was added and stirring was continued for 4 h. The mixture was diluted with water (15 mL) and extracted with ether (3×25 mL). The organic portions were combined, dried over $MgSO_4$, filtered and freed of solvent. The residue was dissolved in MeOH (4 mL) and treated with $NEt_3$ (0.35 mL) for 18 h. The solvent was removed under vacuum and the product was washed on a glass frit with 50% $CH_2Cl_2$:hexanes to give a white solid (~50%) 4-(1,2,3,4,5,6-hexahydro-pentalen-1-ylmethyl)-1,3-dihydro-imidazole-2-thione (Compound 1)

$^1$H NMR (500 MHz, $CDCl_3$ w/TMS): δ 10.6 (s, 1H), 6.41 (s, 1H), 2.80 (brs, 1H), 2.67-2.63 (m, 2H), 2.43-2.36 (m, 2H), 2.21-2.10 (m, 6H), 1.86-1.83 (m, 1H).

Example A-1

Compound 2

Use of 3-methyl-cyclopent-2-enone (commercially available from Aldrich) in Method A produced 4-(3-methyl-cyclopent-2-enylmethyl)-1,3-dihydro-imidazole-2-thione (Compound 2).

$^1$H NMR (500 MHz, $CDCl_3$ w/TMS): δ 11.5 (brs, 1H), 11.3 (brs, 1H), 6.43 (s, 1H), 5.23 (s, 1H), 2.95 (s, 1H), 2.55-2.45 (m, 2H), 2.20 (brs, 2H), 2.08-2.06 (m, 1H), 1.69 (s, 3H), 1.49-1.47 (m, 1H).

Example A-2

Compound 3

Use of 3-ethyl-cyclopent-2-enone (available in accordance with the publication of Woods et. al., J. Amer. Chem. Soc. 1949, 71, 2020, incorporated herein by reference) in Method A produced 4-(3-ethyl-cyclopent-2-enylmethyl)-1,3-dihydro-imidazole-2-thione. $^1$H NMR (500 MHz, $CD_3OD$-$d^4$): δ 6.53 (s, 1H), 5.26 (s, 1H), 2.91 (brs, 1H), 2.51-2.37 (m, 2H), 2.26-2.22 (m, 2H), 2.08-2.02 (m, 3H) 1.52-1.48 (m, 1H), 1.03 (t, J=8.0 Hx, 3H).

Example A-3

Compound 4

Use of 2,3,4,5,6,7-hexahydro-indenone (available in accordance with the publication of Cooke et. al., J. Org. Chem., supra incorporated herein by reference) in Method A produced 4-(2,3,4,5,6,7-hexahydro-1H-inden-1-ylmethyl)-1,3-dihydro-imidazole-2-thione (Compound 4).

$^1$H NMR (500 MHz, DMSO-$d^6$ w/TMS): δ 11.82 (s, 1H), 11.61 (s, 1H), 6.51 (s, 1H), 2.71 (brs, 1H), 2.62-2.51 (m, 1H), 2.12-2.03 (m, 3H), 1.90-1.82 (m, 1H), 1.56-1.36 (m, 5H).

Example A-4

Compound 5

Use of 2-methyl-cyclohex-2-enone (available in accordance with the publication of Hua et. al. J. Org. Chem. 1997, 62, 6888, incorporated herein by reference) in Method A produced 4-(2-methyl-cyclohex-2-enylmethyl)-1,3-dihydro-imidazole-2-thione (Compound 5).

$^1$H NMR (300 MHz, DMSO-$d^6$): δ 11.89 (s, 1H), 11.65 (s, 1H), 6.55 (s, 1H), 5.39 (s, 1H), 2.66-2.61 (m, 1H), 2.16-2.13 (m, 1H), 1.90 (brs, 2H), 1.65 (s, 3H), 1.47-1.36 (m, 4H).

Example A-5

Compound 6

Use of 2-ethyl-cyclohex-2-enone (available in accordance with the publication of Hua et. al. J. Org. Chem. supra) in the method of A produced 4-(2-ethyl-cyclohex-2-enylmethyl)-1,3-dihydro-imidazole-2-thione (Compound 6).

$^1$H NMR (300 MHz, DMSO-d$^6$): δ 11.90 (s, 1H), 11.60 (s, 1H), 6.56 (s, 1H), 5.40 (s, 1H), 2.65-2.50 (m, 1H), 2.30-2.10 (m, 2H), 2.00-1.92 (m, 4H), 1.60-1.36 (m, 4H), 0.98 (t, J=7.5 Hz, 3H).

Example A-6

Compound 7

Use of indanone (commercially available from Aldrich) in Method A produced 4-indan-1-ylmethyl-1,3-dihydro-imidazole-2-thione (Compound 7).

$^1$H NMR (500 MHz, DMSO-d$^6$ w/TMS): δ 11.92 (brs, 1H), 11.68 (brs, 1H), 7.19 (s, 1H), 7.12 (s, 3H), 6.52 (s, 1H), 3.37-3.33 (m, 1H), 2.87-2.71 (m, 3H), 2.40 (dd, J=9.3, 5.4 Hz, 1H), 2.13-2.05 (m, 1H), 1.66-1.59 (m, 1H).

Example A-7

Compound 8

Use of 2-methyl-indanone (commercially available from Aldrich) in the method of A produced 4-(2-methyl-indan-1-ylmethyl)-1,3-dihydro-imidazole-2-thione (Compound 8).

$^1$H NMR (500 MHz, DMSO-d$^6$ w/TMS): δ 11.97 (s, 1H), 11.67 (s, 1H), 7.18-6.91 (series of m, 4H), 6.52 and 6.47 (s, 1H), 3.39-3.23 (m, 2H), 3.0-2.87 (m, 2H), 2.48 (s, 3H), 2.61-2.45 (m, 2H).

Example A-8

Compound 9

Use of 3-methyl-indanone (commercially available from Aldrich) in Method A produced 4-(3-methyl-indan-1-ylmethyl)-1,3-dihydro-imidazole-2-thione as a mixture of diastereomers (Compound 9)

$^1$H NMR (500 MHz, DMSO-d$^6$ w/TMS): δ 11.96 (s, 1H), 11.67 (s, 1H), 7.19-7.08 (m, 4H), 6.58 (6.51) (s, 1H), 3.43-3.00 (series of m, 2H), 2.69-2.31 (series of m, 2H), 1.99-1.94 (m, 1H), 1.71-1.67 (m, 1H), 1.20 (1.18) (s, 3H).

Example A-9

Compound 10

Use of 3,4-dihydro-2H-naphthalen-1-one (commercially available from Aldrich) in Method A produced 4-(1,2,3,4-tetrahydro-naphthalen-1-ylmethyl)-1,3-dihydro-imidazole-2-thione (Compound 10).

$^1$H NMR (500 MHz, DMSO-d$^6$ w/TMS): δ 12.01 (s, 1H), 11.67 (s, 1H), 7.24-7.04 (m, 4H), 6.54 (s, 1H), 3.20-3.01 (m, 2H), 2.69 (brs, 3H), 1.80-1.40 (m, 4H).

Example A-10

Compound 11

Use of 5-chloro-indanone (commercially available from Aldrich) in Method A produced 4-(5-chloro-indan-1-ylmethyl)-1,3-dihydro-imidazole-2-thione (Compound 11).

$^1$H NMR (500 MHz, DMSO-d$^6$ w/TMS): δ 11.95 (s, 1H), 11.68 (s, 1H), 7.27-7.12 (m, 3H), 6.53 (s, 1H), 3.35-3.30 (m, 1H), 2.87-2.76 (m, 3H), 2.45-2.40 (m, 1H), 2.16-2.12 (m, 1H), 1.70-1.67 (m, 1H).

Example A-11

Compound 12

Use of 4-methyl-indanone (commercially available from Aldrich) in Method A produced 4-(4-methyl-indan-1-ylmethyl)-1,3-dihydro-imidazole-2-thione (Compound 12).

$^1$H NMR (500 MHz, DMSO-d$^6$ w/TMS): δ 11.95 (s, 1H), 11.67 (s, 1H), 7.06-6.95 (m, 3H), 6.52 (s, 1H), 3.38 (brs, 1H), 2.81-2.76 (m, 2H), 2.68 (m, 1H), 2.42-2.37 (m, 1H), 2.20 (s, 3H), 2.14-2.10 (m, 1H), 1.67-1.64 (m, 1H).

Example A-12

Compound 13

Use of 5-fluoro-indanone (commercially available from Aldrich) in Method A produced 4-(5-fluoro-indan-1-ylmethyl)-1,3-dihydro-imidazole-2-thione (Compound 13). $^1$H NMR (500 MHz, DMSO-d$^6$ w/TMS): δ 11.96 (s, 1H), 11.68 (s, 1H), 7.14-6.93 (m, 3H), 6.53 (s, 1H), 3.36 (brs, 1H), 2.88-2.77 (series of m, 3H), 2.44-2.39 (m, 1H), 2.16-2.14 (m, 1H), 1.71-1.69 (m, 1H).

Example A-13

Compound 14

Use of 5-methoxy-indan-1-one (commercially available from Aldrich) in Method A produced 4-(5-methoxy-indan-1-ylmethyl)-1,3-dihydro-imidazole-2-thione (Compound 14).

$^1$H NMR (300 MHz, DMSO-d$^6$ w/TMS): δ 11.93 (s, 1H), 11.65 (s, 1H), 7.01 (d, J=8.1 Hz, 1H), 6.78 (s, 1H) 6.71-6.68 (m, 1H), 6.51 (s, 1H), 3.70 (s, 3H), 2.83-2.72 (m, 4H), 2.42-2.34 (m, 1H), 2.13-2.09 (m, 1H), 1.68-1.64 (m, 1H).

Example A-14

Compound 15

Use of 5-bromo-indanone (commercially available from Aldrich) in Method A produced 4-(5-bromo-indan-1-ylmethyl)-1,3-dihydro-imidazole-2-thione (Compound 15).

$^1$H NMR (500 MHz, DMSO-d$^6$ w/TMS): δ (11.95 (s, 1H), 11.68 (s, 1H), 7.41 (s, 1H), 7.32 (d, J=8.1 Hz, 1H), 7.08 (d, J=8.1 Hz, 1H), 6.53 (s, 1H), 2.89-2.74 (m, 3H), 2.46-2.39 (m, 2H), 2.15-2.10 (m, 1H), 1.72-1.64 (m, 1H).

Example A-15

Compound 16

Use of 6-methyl-indanone (commercially available from Aldrich) in Method A produced 4-(6-methyl-indan-1-ylmethyl)-1,3-dihydro-imidazole-2-thione (Compound 16).

¹H NMR (300 MHz, DMSO-d⁶ w/TMS): δ 11.93 (s, 1H), 11.65 (s, 1H), 7.10-6.94 (m, 3H), 6.53 (s, 1H), 2.85-2.65 (m, 3H), 2.37 (dd, J=9.6, 5.1 Hz, 1H), 2.16-2.04 (m, 1H), 1.69-1.57 (m, 1H).

Example A-16

Compound 17

Use of 6-methoxy-indan-1-one (commercially available from Aldrich) in Method A produced 4-(6-methoxy-indan-1-ylmethyl)-1,3-dihydro-imidazole-2-thione (Compound 17).

¹H NMR (300 MHz, DMSO-d⁶ w/TMS): δ 11.93 (s, 1H), 11.66 (s, 1H), 7.11-7.07 (m, 1H), 6.72-6.69 (m, 2H), 6.53 (s, 1H), 3.70 (s, 3H), 3.36-3.33 (m, 1H), 2.83-2.50 (m, 3H), 4.10 (dd, J=9.5, 5.4 Hz, 1H), 2.18-2.06 (m, 1H), 1.69-1.64 (m, 1H).

Example A-17

Compound 100

Chiral HPLC of Compound 7 under the following conditions: ChiralCel OJ® column, 10% IPA:hexane, rt, uv 220 nm, 1 mL/m, produced the following enantiomer: first eluting (+)-(R)-4-indan-1-ylmethyl-1,3-dihydro-imidazole-2-thione (Compound 100), 99% ee.

opt. rotation $[\alpha]_D^{20}$ +33° (c 1.02 in MeOH)
¹H NMR same as Example A-6, Compound 7

Example A-18

Compound 101

Chiral HPLC of Compound 7 under the following conditions: ChiralCel OJ® column, 10% IPA:hexane, rt, uv 220 nm, 1 mL/m, produced the following enantiomer: second eluting (−)-(S)-4-indan-1-ylmethyl-1,3-dihydro-imidazole-2-thione (Compound 101), 98% ee.

opt. rotation $[\alpha]_D^{20}$-38° (c 1.84 in MeOH)
¹H NMR same as Example A-6, Compound 7.

Example A-19

Compound 102

Use of 6,7,8,9-tetrahydro-5H-benzocycloheptene-7-carbaldehyde (obtained as described in Jennesken, et. al. J. Org. Chem. 1986, 51, 2162, incorporated herein by reference) in Method A produced 4-(6,7,8,9-tetrahydro-5H-benzocyclohepten-7-yl)-1,3-dihydro-imidazole-2-thione (Compound 102).

¹H NMR (300 MHz, DMSO-d⁶) δ 11.8 (s, 1H), 11.6 (s, 1H), 7.14-7.07 (m, 4H), 6.48 (s, 1H), 2.89-2.74 (m, 5H), 2.14-2.04 (m, 2H), 1.42-1.31 (m, 2H).

Example A-20

Compound 103

Use of thiochroman-4-one (commercially available from Aldrich) used in Method A produced 4-thiochroman-4-ylmethyl-1,3-dihydro-imidazole-2-thione (Compound 103).

¹H NMR (300 MHz, CDCl₃) δ 12.0 (s, 1H), 11.7 (s, 1H), 7.13-6.97 (m, 4H), 6.60 (s, 1H), 3.16-3.12 (m, 2H), 2.87-2.84 (m, 1H), 2.59-2.56 (m, 2H), 1.93-1.90 (m, 1H), 1.75 (t, J=9.0 Hz, 1H).

Example A-21

Compound 104

Use of 2-chloro-cyclopent-2-enone (obtained as described in Kim, et. al. Synthesis 1993, 283, incorporated herein by reference) in Method A produced (4-(2-chloro-cyclopent-2-enylmethyl)-1,3-dihydro-imidazole-2-thione (Compound 104).

¹H NMR (300 MHz, MeOH-d⁴) δ 6.58 (s, 1H), 5.75 (s, 1H), 3.00-2.80 (m, 2H), 2.40 (dd, J=9.0, 6.0 Hz, 1H), 2.32-2.21 (m, 3H), 1.75-1.65 (m, 1H).

Example A-22

Compound 105

Use of (2-bromo-3-methyl-cyclopent-2-enyl)-acetaldehyde (Intermediate TWELVE-2) in Method A produced 4-(2-bromo-3-methyl-cyclopent-2-enylmethyl)-1,3-dihydro-imidazole-2-thione (Compound 105).

¹H NMR (300 MHz, MeOH-d⁴) δ 6.55 (s, 1H), 3.00 (brs, 1H), 2.90 (dd, J=11.1, 3.9 Hz, 1H), 2.41-2.32 (dd, J=−9.6, 5.4 Hz, 1H), 2.27-2.23 (m, 2H), 2.13-2.01 (m, 1H), 1.73 (s, 3H), 1.72-1.60 (m, 1H).

Example B

Method B: Procedure for preparation of 4-cyclopent-3-enylmethyl-1,3-dihydro-imidazole-2-thione (Compound 18)

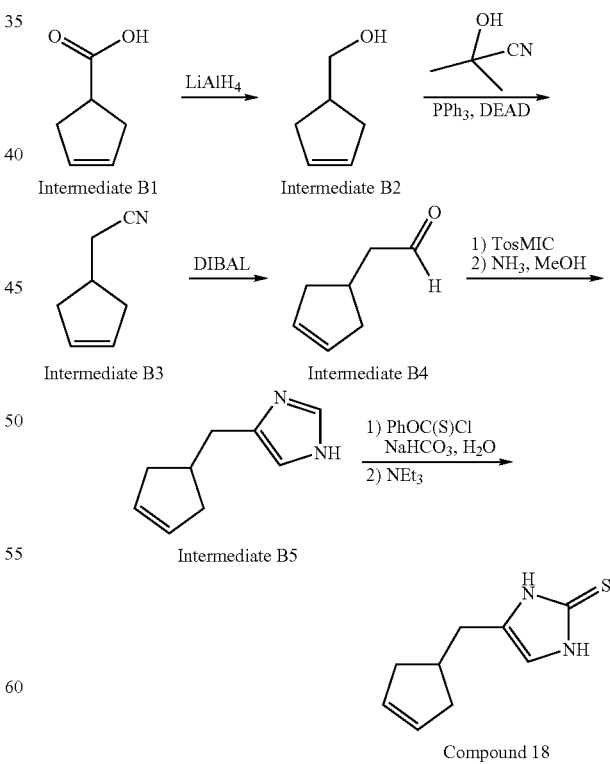

Compound 18

A solution of 3-cyclopentene-1-carboxylic acid (Intermediate B1, available from Aldrich, 2 g, 17.8 mmol) in ether (100 mL) was treated with LiAlH₄ (19 mL, 1M in ether) at 0°

C. for 30 min. The reaction mixture was quenched by addition of Rochelle's salt solution. The mixture was extracted with 50% Et$_2$O:hexanes (3×50 mL). The extracts were dried over MgSO$_4$, filtered and evaporated to dryness. The material (Intermediate B2) was used directly in the next step.

A solution of triphenylphosphine (10.3 g, 39 mmol) in THF (50 mL) at 0° C. was treated with diethyl azodicarboxylate (DEAD) (6 mL) and the mixture was allowed to stir for about 5 min. A solution of cyclopent-3-enyl-methanol (Intermediate B2, 1.8 g, 18.3 mmol) and acetone cynaohydrin (3.4 mL, 38 mmol) in THF (50 mL) was added via syringe over 5 min. The mixture was allowed to stir at 0° C. for 40 min. The ice bath was removed and stirring was continued for 17 h. The mixture was quenched with water and extracted with ether. The ether layer was dried over MgSO$_4$ and the mixture was carefully freed of solvent. The residue was purified by chromatography with 10% ether:pentane to give cyclopent-3-enyl-acetonitrile (Intermediate B3) 1.16 g (60%) over two steps.

A solution of (diisobutyl aluminum hydride (DIBAL) (7 mL, 1M in cyclohexane) was added to cyclopent-3-enyl-acetonitrile (Intermediate B3, 520 mg, 4.9 mmol) at −70° C. After 30 min, the mixture was quenched with Rochelle's salt solution. The aqueous phase was extracted with ether (3×20 mL) and the combined organic layers were dried over MgSO$_4$, filtered and evaporated to dryness. The crude aldehyde (Intermediate B4) (~0.5 g) was employed in the next step.

Formation of 4-cyclopent-3-enylmethyl-1,3-dihydro-imidazole-2-thione (Compound 18) was completed by employing the same procedure, without formation of the fumarate, as described in Example A, and indicated above in the reaction scheme.

$^1$H NMR (500 MHz, DMSO-d$^6$ w/TMS) δ 11.8 (s, 1H) 11.6 (s, 1H) 6.56 (s, 1H) 5.65 (s, 2H) 2.50-2.35 (m, 5H), 1.98-1.94 (m, 2H).

Example C

Method C: Procedure for the preparation of 4-cyclohex-2-enylmethyl-1,3-dihydro-imidazole-2-thione (Compound 19)

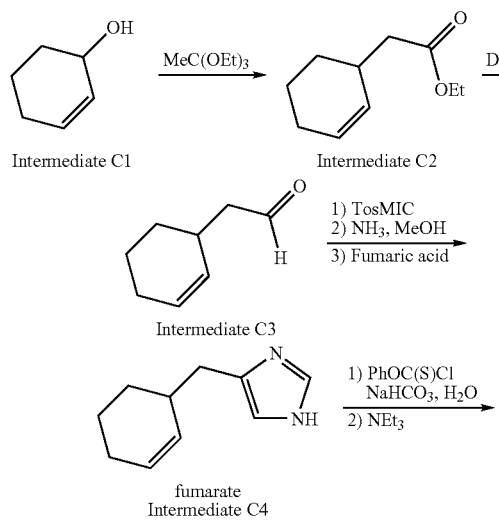

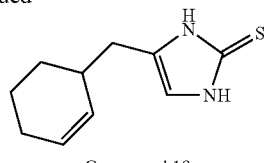

Compound 19

A solution of cyclohexenol (Intermediate C1, available from Aldrich, 2.0 g, 20.4 mmol) in triethyl orthoacetate (30 mL) and propionic acid (~0.025 mL, cat) was heated to remove ethanol. After the ethanol was removed heating was continued at 145° C. for 1 h. The triethyl orthoacetate was removed by simple distillation. After the residue cooled to rt the product was purified by chromatography on SiO$_2$ with 5% ether:hexane to give the ester (Intermediate C2) as a clear colorless oil 1.08 g (~31%).

A solution of the above ethyl ester (Intermediate C2, 1.0 g, 5.9 mmol) was dissolved in hexanes (50 mL) and cooled to −78° C. A solution of DIBAL (5.8 mL 1.0 M in cyclohexane) was added dropwise. After 15 min, diethyl ether (50 mL) was added and the mixture was stirred with Rochelle's salt solution (25 mL) for 10 m. The organic layer was separated, dried and filtered. Chromatography on SiO$_2$ with 7% Et$_2$O:hexane delivered the aldehyde (Intermediate C3), as a clear colorless oil, 0.52 g (74%). The aldehyde (Intermediate C3) was subjected to the Büchi protocol (Horne et al.), as described above in Method A. The fumarate salt of the imidazole (Intermediate C4) was obtained (25% overall). Formation of 4-cyclohex-2-enylmethyl-1,3-dihydro-imidazole-2-thione (Compound 19) was completed by employing the same procedure as described in Example A.

$^1$H NMR (500 MHz, DMSO-d$^6$ w/TMS) δ 11.9 (s, 1H), 11.7 (s, 1H), 6.56 (s, 1H), 5.7-5.4 (m, 2H) 2.37-2.20 (m, 3H), 1.93-1.16 (series of m, 6H).

Example D

Method D: Procedure for preparation of 4-(2-isobutyl-cyclopent-2-enylmethyl)-1,3-dihydro-imidazole-2-thione (Compound 20)

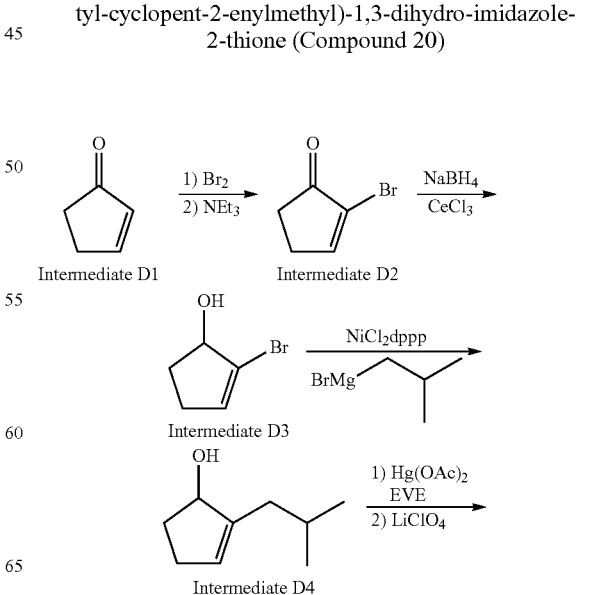

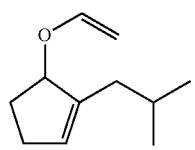 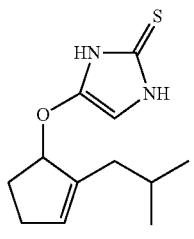

Intermediate D5 → Compound 20

Reagents: 1) TosMIC; 2) NH₃, MeOH; 3) PhOC(S)Cl, NaHCO₃, H₂O; 4) NEt₃

A solution of 2-cyclopentene-1-one (Intermediate D1, commercially available from Aldrich) (1.5 mL, 17.5 mmol) in CH₂Cl₂ (40 mL) at 0° C. was treated with bromine (0.86 mL, 16.6 mmol) in CH₂Cl₂ (30 mL) over 10 min. (see: J. Org. Chem. 1982 47, 5088 incorporated herein by reference). The mixture was allowed to stir at 0° C. for one hour. Triethylamine (3.8 mL) was added and the mixture was allowed to stir at rt for 1.5 h. The mixture was diluted with CH₂Cl₂, washed with 10% HCl. The combined layers were washed with sat. NaHCO₃, brine and dried over Na₂SO₄. The mixture was filtered and evaporated to give 2-bromo-cyclopent-2-enone (Intermediate D2, 2.85 g).

The bromoenone (Intermediate D2, ~17.5 mmol) was dissolved in 0.4M CeCl₃.7H₂O in MeOH (66 mL) at 0° C. Sodium borohydride was added portion-wise and stirring was continued for 10 min. after addition was complete. The mixture was quenched with saturated NH₄Cl and extracted with ether. The combined organic layers were washed with sat. NH₄Cl, H₂O, brine, and dried over Na₂SO₄, filtered and evaporated to dryness. The material was purified by column chromatography 15% EtOAc:Hx to give 2-bromo-cyclopent-2-enol (Intermediate D3, ~2 g, 70% over 2 steps).

The alcohol (Intermediate D3, 16 mmol) in THF (30 mL) at 0° C. was treated with isobutyl magnesium bromide (40 mmol). The catalyst, 1,3-bis(diphenylphosphino)propane nickel (II) chloride (0.75 mmol) (NiCl₂dppp) was added in one portion and the mixture was heated to reflux for 3 h. (see: Organ et al. J. Org. Chem. 1997, 62, 41523, incorporated herein by reference). The reaction mixture was cooled to rt and quenched with sat. NH₄Cl solution. The mixture was filtered and partitioned between brine and diethyl ether. The organic layer was removed and dried over Na₂SO₄, filtered and concentrated under vacuum. The oil was purified by chromatography on SiO₂ with 20% EtOAc:Hx to yield 2-isobutyl-cyclopent-2-enol (Intermediate D4). Use of 2-isobutyl-cyclopent-2-enol (Intermediate D4) in Method A produced 4-(2-isobutyl-cyclopent-2-enylmethyl)-1,3-dihydro-imidazole-2-thione (Compound 20):

¹H NMR (300 MHz, CD₃OD-d⁴): δ 6.55 (s, 1H), 5.38 (s, 1H), 2.80-2.68 (m, 2H), 2.26-2.18 (m, 3H), 2.03-1.73 (series of m, 4H), 1.58-1.51 (m, 1H), 0.93 (d, J=6.3 Hz, 3H), 0.83 (d, J=6.3 Hz, 3H).

Example D-1

Compound 21

Use of vinyl magnesium bromide (commercially available from Aldrich) in Method D produced 2-vinyl-cyclopent-2-enol. The employment of this alcohol in Method A produced 4-(2-vinyl-cyclopent-2-enylmethyl)-1,3-dihydro-imidazole-2-thione (Compound 21).

¹H NMR (300 MHz, CD₃OD-d⁴): δ 6.55-6.43 (m, 2H), 5.74 (s, 1H), 5.27-5.06 (m, 2H), 3.11 (s, 1H), 2.79 (dd, J=3.3, 11.7 Hz, 1H), 2.34-2.26 (m, 3H), 2.01-1.94 (m, 1H), 1.79-1.75 (m, 1H).

Example D-2

Compound 22

Use of 1-propenylmagnesium bromide (commercially available from Aldrich) in Method D produced 2-propenyl-cyclopent-2-enol. Employment of this alcohol in Method A produced the cis/trans isomers: 4-(2-propenyl-cyclopent-2-enylmethyl)-1,3-dihydro-imidazole-2-thione (Compound 22).

¹H NMR (300 MHz, CD₃OD-d⁴): δ 6.56-6.52 (m, 1H), 6.18 (6.13) (s, 1H), 5.82-5.49 (m, 2H), 5.56 (s, 1H), 3.05 (m, 1H), 2.78-2.66 (m, 1H), 2.33-2.15 (m, 3H), 2.04-1.87 (m, 1H), 1.77 (d, J=6.3 Hz, 3H), 1.73-1.55 (m, 1H).

Example E

Method E: Procedure for preparation 2-(2-thioxo-2, 3-dihydro-1H-imidazol-4-ylmethyl)-3,4-dihydro-2H-naphthalen-1-one (Compound 23 and Compound 24)

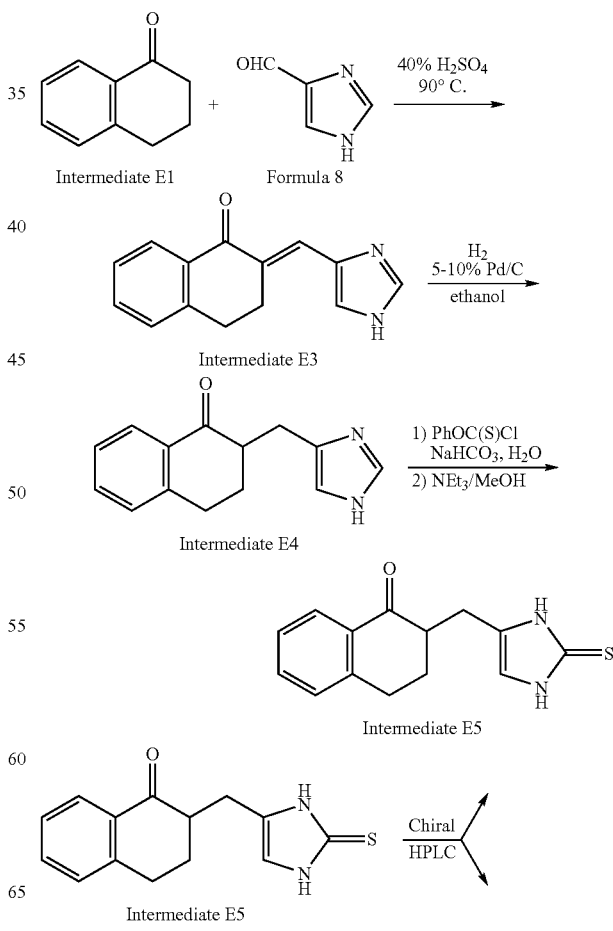

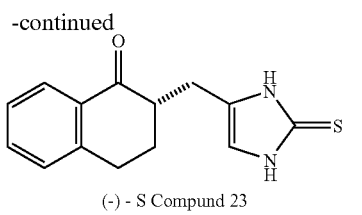

(−) - S Compund 23

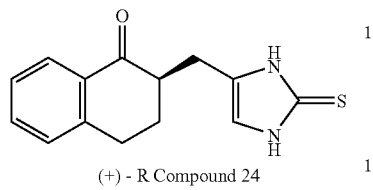

(+) - R Compound 24

1-Tetralone (commercially available from Aldrich) (Intermediate E1, 1.24 g, 8.5 mmol) and 4,5-imidazole carboxaldehyde (Formula 8, (0.82 g, 8.5 mmol) were added to 8.5 mL of a 40% solution of $H_2SO_4$. The solution was heated for 24 h at 90° C. After cooling to rt, the reaction was made basic with excess concentrated $NH_4OH$. The mixture was extracted twice with THF. The organic layers were combined and washed with brine. The organic layer was separated and dried over $Na_2SO_4$. The mixture was filtered and the filtrate concentrated under reduced pressure to afford ~2.2 g of a yellow solid 2-(1H-imidazol-4-ylmethylene)-3,4-dihydro-2H-naphthalen-1-one (Intermediate E3). The crude product (Intermediate E3) was suspended in ethanol (100 mL) and a palladium on carbon catalyst (10%, 0.27 g) added. The mixture was shaken in a Parr hydrogenator apparatus while under 40 psi of hydrogen. After 19 h the reaction mixture was filtered through Celite and the filtrate concentrated under reduced pressure. Column chromatography with 5-7% $MeOH:CHCl_3$ afforded ~0.9 g (45%) of a solid comprising 2-(1H-imidazol-4-ylmethylene)-3,4-dihydro-2H-naphthalen-1-one (Intermediate E4). The synthesis of 2-(2-thioxo-2,3-dihydro-1H-imidazol-4-ylmethyl)-3,4-dihydro-2H-naphthalen-1-one (Intermediate E5) was completed by subjecting the imidazole (Intermediate E4) to the conditions described in Method A for Example A for the conversion to the thione (Intermediate E5).
$^1H$ NMR (500 MHz, DMSO-$d^6$ w/TMS) δ 11.9 (s, 1H), 11.7 (s, 1H), 7.88 (d, J=7.5 Hz, 1H), 7.57-7.54 (m, 1H), 7.37-7.34 (m, 2H), 6.58 (s, 1H), 3.08-2.97 (m, 2H), 2.86-2.85 (m, 1H), 2.43 (dd, J=9.0, 6.0 Hz, 1H), 2.08 (dd, J=4.0, 4.5 Hz, 1H), 1.1 (brs, 1H).

The racemic 2-(2-thioxo-2,3-dihydro-1H-imidazol-4-ylmethyl)-3,4-dihydro-2H-naphthalen-1-one (Intermediate E5) was separated by chiral HPLC using a ChiralPak AD 4.6×220 mm (Daicel Chem. Ind. Ltd.) with isocratic flow 1.2 mL/m, 10% isopropyl alcohol in acetonitrile mobile phase at 20° C. and UV 210 nm. The first peak with 6.5 min. retention time gave Compound 23 (−) S with $[α]_D^{20}$ −66.4 (c=0.57 in 9% DMSO:MeOH). The second fraction at 14.0 min. gave Compound 24 (+) R with $[α]_D^{20}$ +61.9 (c=0.63 in 10% DMSO:MeOH). The absolute stereochemistry of Compounds 23 and 24, as shown in the scheme, was assigned by derivatization followed by X-ray crystallography.
Following the procedure of Example E, fused ring compounds are reacted to yield the thione derivatives listed below.

Example E-1

Compound 25

5-(2-Thioxo-2,3-dihydro-1H-imidazol-4-ylmethyl)-6,7-dihydro-5H-benzo[b]thiophen-4-one is prepared by using 6,7-dihydro-5H-benzo[b]thiophen-4-one as a starting material in Method E.
$^1H$ NMR (500 MHz, DMSO-$d^6$ w/TMS): δ 11.87 (s, 1H), 11.69 (s, 1H), 7.40 (d, J=5.5 Hz, 1H), 7.27 (d, J=5.5 Hz, 1H), 6.57 (s, 1H), 3.13-2.98 (m, 3H), 2.80-2.79 (m, 1H), 2.41 (dd, J=9.5, 6.0 Hz, 1H), 2.15-2.11 (m, 1H), 1.81-1.78 (m, 1H).

Example E-2

Compound 26

4-Methyl-2-(2-thioxo-2,3-dihydro-1H-imidazol-4-ylmethyl)-3,4-dihydro-2H-naphthalen-1-one (Compound 26 is prepared by using 4-methyl-3,4-dihydro-2H-naphthalen-1-one (commercially available from Aldrich) as a starting material in Method E.
$^1H$ NMR (300 MHz, $CD_3OD$-$d^4$): δ diastereomers: 7.99-7.90 (m, 1H), 7.60-7.48 (m, 2H), 7.36-7.31 (t, J=9 Hz, 1H), 6.62 (6.60) (s, 1H), 3.19-3.12 (m, 2H), 2.90-2.82 (m, 1H), 2.63 (dd, J=7.5, 9.0 Hz, 1H), 2.17-1.98 (m, 1H), 1.57-1.44 (m, 1H), 1.40 (t, J=7.0 Hz, 3H).

Example E-3

Compound 27

2-(2-Thioxo-2,3-dihydro-1H-imidazol-4-ylmethyl)-indan-1-one (Compound 27) is prepared by using indanone (commercially available from Aldrich) as starting material in Method E.
$^1H$ NMR (300 MHz, 300 MHz, $CD_3OD$-$d^4$): δ 7.72-7.38 (m, 4H), 6.61 (s, 1H), 3.38-3.33 (m, 1H), 3.08-2.99 (m, 2H), 2.87 (dd, J=13.2, 4.1 Hz, 1H), 2.67-2.60 (m, 1H).

Example E-4

Compound 28

6-Hydroxy-2-(2-thioxo-2,3-dihydro-1H-imidazol-4-ylmethyl)-3,4-dihydro-2H-naphthalen-1-one is prepared by substituting 6-hydroxy-3,4-dihydro-2H-naphthalen-1-one (commercially available from Aldrich) in Method E.
$^1H$ NMR (300 MHz, $CD_3OD$-$d^4$): δ 7.85 (d, J=8.8 Hz, 1H), 6.81 (s, 1H), 6.70 (dd, J=6.1, 2.4 Hz, 1H), 6.61 (d, J=2.3 Hz, 1H), 3.22 (dd, J=3.8, 10.6 Hz, 1H), 2.92-2.88 (m, 2H), 2.78-2.62 (m, 2H), 2.14-2.09 (m, 1H), 1.78-1.70 (m, 1H).

Example E-5

Compound 106

Use of 7,8-dihydro-6H-quinolin-5-one (obtained as described in Huang, et al, Synthetic Communications, 1998, 28, 1197, incorporated herein by reference) in Method E produced 6-(1H-imidazol-4-ylmethyl)-2,3,4,6,7,8-hexahydro-1H-quinolin-5-one as a side product of the reduction step. This reduced material was used in Method E to produce 6-(2-thioxo-2,3-dihydro-1H-imidazol-4-ylmethyl)-2,3,4,6,7,8-hexahydro-1H-quinolin-5-one (Compound 106).
$^1H$ NMR (300 MHz, MeOH-$d^4$) δ 6.58 (s, 1H), 3.25-3.21 (m, 2H), 2.95 (dd, J=6.6, 2.2 Hz, 1H), 2.57 (dd, J=5.4, 3.9 Hz, 1H), 2.47-2.30 (m, 5H), 1.96-1.92 (m, 1H), 1.80-1.76 (m, 2H), 1.63-1.56 (m, 1H).

Example E-6

Compound 107

Use of 7,8-dihydro-6H-quinolin-5-one (obtained as described in Huang, et. al. Synthetic Communications, 1998, 28, 1197, incorporated herein by reference) in Method E produced 6-(2-thioxo-2,3-dihydro-1H-imidazol-4-ylmethyl)-7,8-dihydro-6H-quinolin-5-one (Compound 107).

$^1$H NMR (300 MHz, MeOH-d$^4$) δ 8.46 (dd, J=4.8, 1.8 Hz, 1H), 8.33 (dd, J=7.8, 1.5 Hz, 1H), 7.42 (dd, J=8.1, 4.8 Hz, 1H), 6.63 (s, 1H), 3.22-3.12 (m, 3H), 2.95-2.85 (m, 1H), 2.71-2.63 (dd, J=4.8, 3.3 Hz, 1H), 2.30-2.21 (m, 1H), 1.94-1.81 (m, 1H).

Example F

Compound 29

Method F: Procedure for preparation of 4-(4,5,6,7-Tetrahydro-benzo[b]thiophen-5-ylmethyl)-1,3 dihydro-imidazole-2-thione (Compound 29)

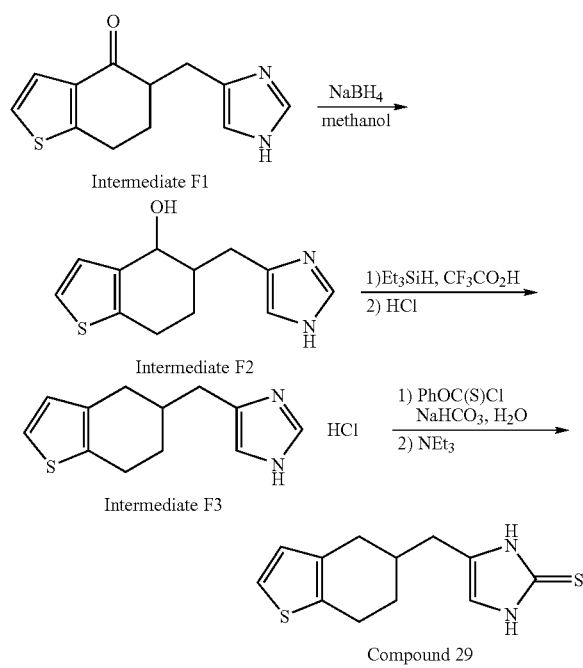

5-(1H-Imidazol-4-ylmethyl)-6,7-dihydro-5H-benzo[b]thiophen-4-one (Intermediate F1, an intermediate already prepared by Method E in the synthesis of Example E-1, Compound 25, 0.44 g, 1.90 mmol) was added to methanol (20 mL). Sodium borohydride (74 mg, 1.95 mmol) was added to the solution. After stirring for 2.5 h at rt the reaction mixture was quenched with water. The mixture was extracted twice with ethyl acetate. The organic layers were combined and washed with brine. The organic layer was separated and dried over Na$_2$SO$_4$. The mixture was filtered and the filtrate concentrated under reduced pressure to afford 0.4 g of a white solid 5-(1H-imidazol-4-ylmethyl)-4,5,6,7-tetrahydrobenzo[b]thiophen-4-ol (Intermediate F2). The crude product (Intermediate F2) was dissolved in CH$_2$Cl$_2$ (25 mL). Triethylsilane (2.5 mL, 15.6 mmol) and trifluoroacetic acid (4.8 mL, 62 mmol) were added and the mixture was stirred at rt for 22 h. The solution was made basic with 2N NaOH and the organic layer separated and washed with brine. The solution was dried over Na$_2$SO$_4$. The mixture was filtered and the filtrate concentrated under reduced pressure. Column chromatography with 7% methanol in chloroform afforded 0.39 g (80%) of Intermediate F3. The product was dissolved in methanol and an excess of hydrogen chloride (HCl) in ether was added. The solution was concentrated under reduced pressure to yield 0.3 g of a solid. Column chromatography with 7% methanol in chloroform afforded 0.21 g (~45%) of the hydrochloride salt of 4-(4,5,6,7-tetrahydro-benzo[b]thiophen-5-ylmethyl)-1,3-dihydro-imidazole-2-thione (Intermediate F3), as white crystals after recrystallization from a mixture of acetone and methanol. The synthesis of 4-(4,5,6,7-tetrahydro-benzo[b]thiophen-5-ylmethyl)-1,3-dihydro-imidazole-2-thione (Compound 29) was completed by subjecting the hydrochloride salt of the imidazole (Intermediate F3) to the conditions described in Method A for the synthesis of Compound 1 (Example A) 4-(4,5,6,7-tetrahydro-benzo[b]thiophen-5-ylmethyl)-1,3-dihydro-imidazole-2-thione (Compound 29):

$^1$H NMR (500 MHz, DMSO-d$^6$ w/TMS) δ 11.9 (s, 1H), 11.7 (s, 1H), 7.22 (d, J=5 Hz, 1H), 6.75 (d, J=5 Hz, 1H), 6.60 (s, 1H), 2.80-2.59 (series of m, 4H), 2.42-1.87 (series of m, 4H), 1.43-1.35 (m, 1H).

Example F-1

Compound 30

4-(1,2,3,4-Tetrahydro-naphthalen-2-ylmethyl)-1,3-dihydro-imidazole-2-thione (Compound 30) is prepared by using 2-(1H-imidazol-4-ylmethylene)-3,4-dihydro-2H-naphthalen-1-one as a starting material (see: method E above in Method F.

$^1$H NMR (300 MHz, CD$_3$OD-d$^4$): δ 7.03-7.01 (m, 4H), 6.60 (s, 1H), 2.82-2.76 (m, 3H), 2.52 (d, J=6.7 Hz, 1H), 2.45 (dd, J=10.3, 6.4 Hz, 1H), 2.01-1.92 (m, 3H), 1.43-1.39 (m, 1H).

Example F-2

Compound 108

4-(1,2,3,4-Tetrahydro-naphthalen-2-ylmethyl)-1H-imidazole (prepared by the process in Method F) was separated by chiral HPLC under the following conditions: ChiralPakAD® column, with 10% EtOH:hexane. The first fraction eluted was 4-(1,2,3,4-tetrahydro-naphthalen-2-ylmethyl)-1H-imidazole and it was converted to (−)-(s)-4-(1,2,3,4-tetrahydro-naphthalen-2-ylmethyl)-1,3-dihydro-imidazole-2-thione (Compound 108) by the applicable process steps described in Method A.

opt. rotation [α]$_D^{20}$ −85° (c 0.75 in MeOH:DMSO 1:1)

$^1$H NMR same as Compound 30.

Example F-3

Compound 109

(+)-(R)-4-(1,2,3,4-Tetrahydro-naphthalen-2-ylmethyl)-1,3-dihydro-imidazole-2-thione was isolated as the second fraction in accordance with the method reported for Example F-2 (Compound 109).

opt. rotation [α]$_D^{20}$ +78° (c 1.25 in DMSO)

$^1$H NMR same as Compound 30.

Examples G and G-1

Compound 31 and Compound 32

Procedure for preparation of 2-(2-thioxo-2,3-dihydro-1H-imidazol-4-ylmethyl)-3,4,5,6,78-hexahydro-2H-naphthalen-1-one and 4-(1,2,3,4,5,6,7,8-octahydro-naphthalen-2-ylmethyl)-1,3-dihydro-imidazole-2-thione (Compound 31 and Compound 32)

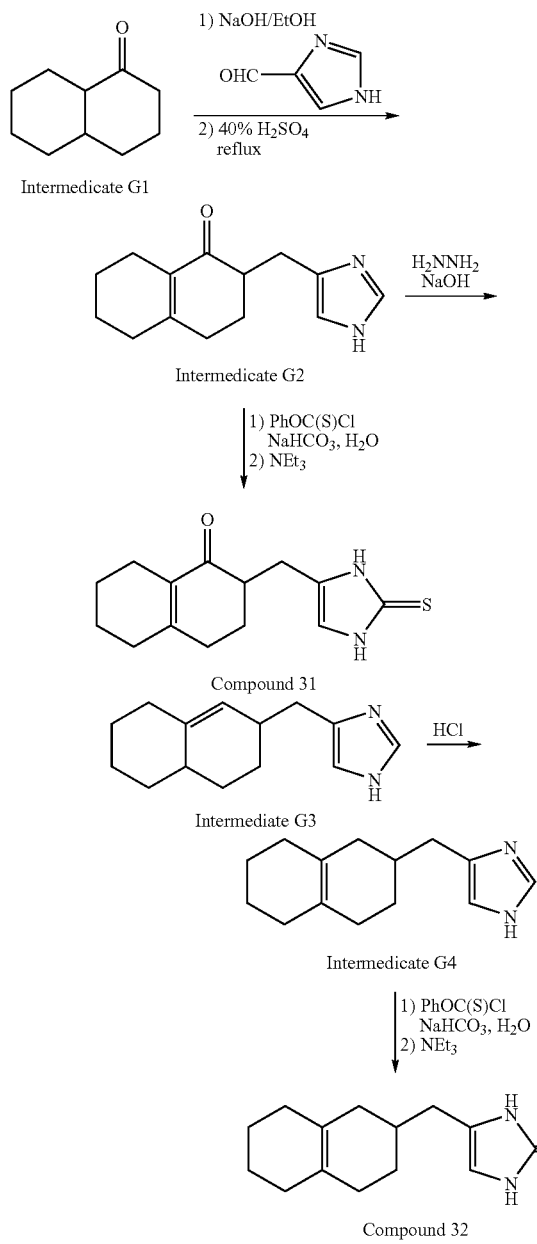

1-Decalone (Intermedate G1, commercially available from Aldrich) (10.0 g, 66 mmol) and 4(5)-imidazole carboxaldehyde (Formula 8, 6.3 g, 66 mmol) were added to EtOH (100 mL). NaOH (5.2 g, 130 mmol) in $H_2O$ (20 mL) was added and the mixture was heated at reflux for 5 days. The mixture was cooled to rt and acidified with aqueous HCl. The solution was extracted with THF/ethyl acetate and the organic layers were combined and washed with brine. The organic phase was dried over $MgSO_4$, filtered and freed of solvent. The crude product was heated at reflux in 40% $H_2SO_4$ for 24 h. The reaction was cooled to rt and made basic with saturated $K_2CO_3$. The solution was extracted with THF/ethyl acetate and the organic layers were combined and washed with brine. The organic phase was dried over $MgSO_4$ and the solvent removed under reduced pressure. Purification by flash chromatography (15:1 $CH_3Cl$/MeOH) afforded Intermediate G2 (4.9 g, 32% yield).

The synthesis of compound 2-(2-thioxo-2,3-dihydro-1H-imidazol-4-ylmethyl)-3,4,5,6,7,8-hexahydro-2H-naphthalen-1-one (Compound 31) was completed by subjecting the imidazole (Intermediate G2) to the applicable process steps described in Method A in connection with Example A. Compound 31:

$^1$H NMR (500 MHz, DMSO-$d^6$ w/TMS) δ 11.8 (s, 1H), 11.7 (s, 1H), 6.52 (s, 1H), 2.89 (dd, J=4, 4.5 Hz, 1H), 2.29-1.47 (series of m, 14H).

The free base of the hydrochloride salt of Intermediate G2 (3.0 g, 11 mmol) was generated with NaOH and then added to diethylene glycol (100 mL). To the solution was added hydrazine hydrate (3.2 mL, 100 mmol) and the mixture was stirred overnight at rt. NaOH (3.1 g, 77 mmol) was added and the solution heated at reflux for 5 days. The solution was cooled to rt and diluted with water. The aqueous layer was extracted with THF/ethyl acetate. The organic layers were combined, washed with brine, dried $MgSO_4$ and the solvent removed under reduced pressure. Purification by flash chromatography (8:1 $CH_3Cl$:MeOH) afforded Intermediate G3 (0.64 g, 27% yield).

4-(2,3,4,4a,5,6,7,8-Octahydro-naphthalen-2-ylmethyl)-1H-imidazole (Intermediate G3) (1.0 g, 4.6 mmol) was added to 10 mL of concentrated HCl. The solution was stirred at rt for 30 m and neutralized with $K_2CO_3$. The solution was extracted with THF/ethyl acetate. The organic layers were combined and washed with brine, and dried over $MgSO_4$. The solvent was removed under reduced pressure. Purification by flash chromatography (15:1 $CH_3CH_3$/MeOH) gave Intermediate G4.

The synthesis of compound 4-(1,2,3,4,5,6,7,8-octahydro-naphthalenylmethyl)-1,3-dihydro-imidazole-2-thione (Compound 32) was completed by subjecting the imidazole Intermediate G4 to the applicable process steps described in Method A in connection with Example A. Compound 32:

$^1$H NMR (500 MHz, DMSO-$d^6$ w/TMS) δ 11.8 (s, 1H), 11.6 (s, 1H), 6.54 (s, 1H), 2.28 (d, J=6.5 Hz, 2H), 1.88-1.45 (m, 14H), 1.11 (brs, 1H).

Example G-2

Compound 110

Intermediate G4 was separated by chiral HPLC: ChiralPakAD® column, with 10% EtOH:hexane. Use of (R)-4-(1,2,3,4,5,6,7,8-octahydro-naphthalen-2-ylmethyl)-1H-imidazole) in the applicable process steps described in Method A produced (1,2,3,4,5,6,7,8-octahydro-naphthalen-2-ylmethyl)-1,3-dihydro-imidazole-2-thione (Compound 110)

$^1$H NMR same as Compound 32.

Example H

Compound 33

Method H: Procedure for preparation of 8-Hydroxymethyl-2-(2-thioxo-2,3-dihydro-1H-imidazol-4-ylmethyl)-3,4-dihydro-2H-naphthalen-1-one (Compound 33)

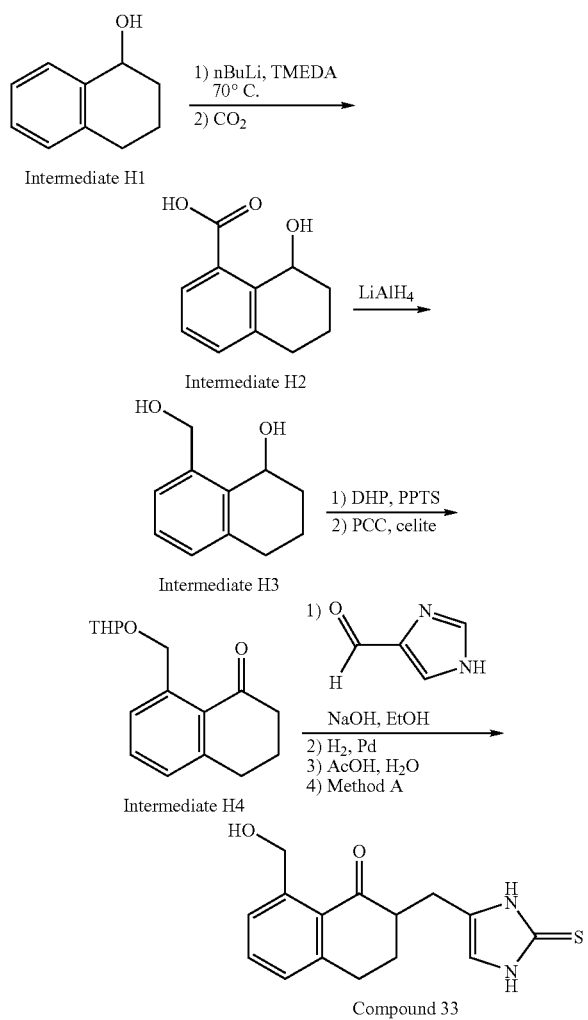

1,2,3,4-Tetrahydro-naphthalen-1-ol (Intermediate H1 commercially available from Aldrich, 13 mL, 93 mmol) was dissolved in dry hexane (300 mL) and heated to 70° C. A solution of nBuLi (75 mL, 2.5M in hexane) and N,N,N',N'-tetramethylethylenediamine (TMEDA) 28 mL) in dry hexane (30 mL) was added dropwise via an addition funnel to the solution. The addition was completed and heating was continued for 2 h. The mixture was cooled to 0° C. and CO$_2$ gas was bubbled through the mixture for 8-12 h. The solution was stored at rt for 24 h before dilution with H$_2$O and acidification with 3N HCl and conc. HCl until pH ~2. The aqueous layer was extracted with ethyl acetate. The organic layer was extracted with sat NaHCO$_3$ (3×) and the combined basic aqueous extracts were cooled to 0° C. and acidified with 3N HCl to HCl until a pale yellow solid precipitated. The resulting carboxylic acid (Intermediate H2) (28%) was collected by filtration and dried under vacuum.

Intermediate H2 was used in the next step without further purification. It was dissolved in THF (70 mL) and added dropwise to a solution of LiAlH$_4$ (28 mL, 1M in THF). The reaction was stirred at rt for 1 h and heated to reflux (90° C.) for 2 h. The mixture was cooled to rt, quenched with Rochelle's salt solution and stirred for 1 h. The aqueous layer was separated and extracted with ethyl acetate. The organic layers were combined, dried over MgSO$_4$, filtered and freed of solvent to give 8-hydroxymethyl-1,2,3,4-tetrahydro-naphthalen-1-ol (Intermediate H3) (57%) as a white solid that was sufficiently pure for the subsequent process steps.

The diol (Intermediate H3) (2.42 g, 13.5 mmol) was dissolved in CH$_2$Cl$_2$ (75 mL) and reacted with dihydropyran (1.3 mL, 13.8 mmol) and pyridinium para-toluene sulfonate (PPTS) (350 mg, 1.36 mmol) at rt for 18 h. The mixture was concentrated onto SiO$_2$ and purified by chromatography with 10% EtOAc:Hx. The tetrahydropyranyl (THP) protected alcohol (2.02 g, 7.70 mmol) was dissolved in CH$_2$Cl$_2$ (10 mL) and added to a mixture of pyridinium chlorochromate (PCC) (4.9 g, 22.2 mmol), sodium acetate (310 mg, 3.56 mmol) and celite (~10 g) in CH$_2$Cl$_2$ (100 mL). The mixture was reacted at rt for 18 h and filtered through celite. The residue was purified by chromatography on SiO$_2$ with 20 to 30% EtOAc:Hx to yield 8-(tetrahydro-pyran-2-yloxymethyl)-3,4-dihydro-2H-naphthalen-1-one (Intermediate H4) (~55%).

The THP-protected ketone (Intermediate H4) was dissolved in EtOH (15 mL) and reacted with imidazole carboxaldehyde (Formula 8, 0.50 g, 5.1 mmol) and 2N NaOH (2 mL) at reflux for 36 h. The mixture was cooled to rt and subjected to a standard aqueous work-up. The crude residue was hydrogenated in a mixture of EtOH (150 mL) and Pd (160 mg, 10% on C) under 40 psi of H$_2$. After 18 h at rt the THP protected compound was isolated (12%). The THP group was removed in a mixture of acetic acid (4 mL), THF (2 mL) and H$_2$O (1 mL) at 80° C. over 4 h. The mixture was made slightly basic and extracted with EtOAc. The organic layer was dried over MgSO$_4$, filtered and concentrated. The synthesis of the 8-hydroxymethyl-2-(2-thioxo-2,3-dihydro-1H-imidazol-4-ylmethyl)-3,4-dihydro-2H-naphthalen-1-one (Compound 33) was completed by subjecting the imidazole compound Intermediate H4 to the applicable process steps described in Method A in connection with Example A. Compound 33:

$^1$H NMR (300 MHz, CD$_3$OD-d$^4$) δ 7.59-7.47 (m, 2H), 7.23 (d, J=7.5 Hz, 1H), 6.61 (s, 1H), 4.98-4.88 (m, 2H), 3.13-3.04 (m, 2H), 2.87-2.79 (m, 1H), 2.64 (dd, J=4.5, 7.2 Hz, 1H), 2.20-2.11 (m, 1H), 1.85-1.71 (m, 1H).

Example I

Compound 34

Procedure for the preparation 8-methyl-2-(2-thioxo-2,3-dihydro-1H-imidazol-4-ylmethyl)-3,4-dihydro-2H-naphthalen-1-one (Compound 34)

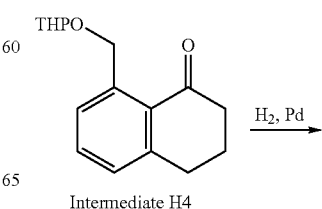

Intermediate H4

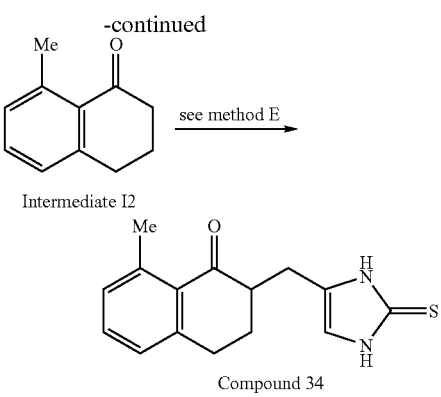

8-(Tetrahydro-pyran-2-yloxymethyl)-3,4-dihydro-2H-naphthalen-1-one (Intermediate H4) (obtained in Method H, 550 mg, 2.11 mmol) was hydrogenated with H$_2$ (balloon) and 10% Pd/C (190 mg) at rt for 18 h. The mixture was filtered through celite and the crude product was isolated by evaporation of the solvent under reduced pressure. 8-Methyl-3,4-dihydro-2H-naphthalen-1-one (Intermediate 12) was subjected to the applicable process steps of Method E to produce (Compound 34).

$^1$H NMR (300 MHz, CD$_3$OD-d$^4$) δ 7.32 (t, J=7.7 Hz, 1H), 7.13-7.08 (m, 2H), 6.60 (s, 1H), 3.05-3.00 (m, 3H), 3.82-2.58 (m, 2H), 2.57 (s, 3H), 2.16-2.09 (m, 1H), 1.82-1.73 (m, 1H).

Example J

Procedure for preparation of 8-Fluoro-2-(2-thioxo-2,3-dihydro-1H-imidazol-4-ylmethyl)-3,4-dihydro-2H-naphthalen-1-one (Compound 35)

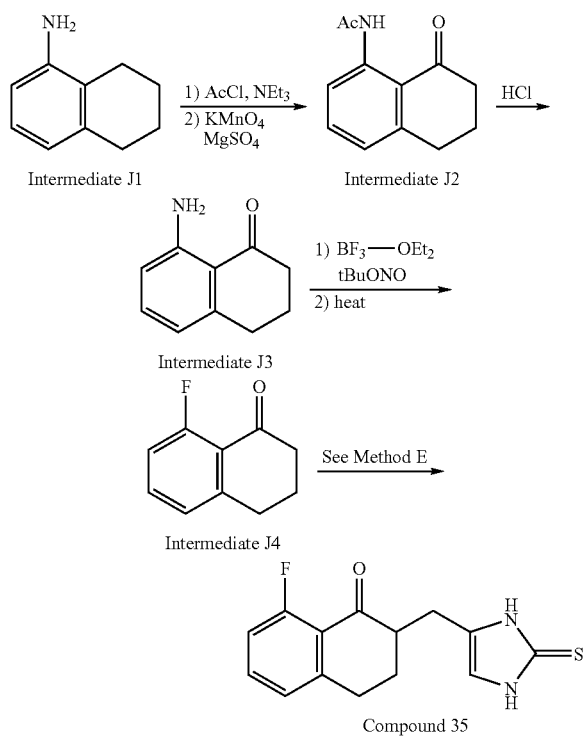

5,6,7,8-Tetrahydro-naphthalen-1-ylamine (Intermediate J1, commercially available from Aldrich) (5 mL, 35.3 mmol) was dissolved in CH$_2$Cl$_2$ (40 mL) and treated with NEt$_3$ (10 mL) and acetyl chloride (3.8 mL, 53 mmol) at rt for 1 h. The mixture was diluted in CHCl$_3$ and acidified with sat NH$_4$Cl. The aqueous layer was extracted with CHCl$_3$. The organic fractions were combined, dried and evaporated and the amide was used without further purification. The resulting amide (35.3 mmol) in acetone (450 mL) and aqueous MgSO$_4$ (5 g in 28 mL) at 0° C. was treated with KMnO$_4$ (16.8 g, 105 mmol). The mixture was allowed to stir at 0° C. for 2 h. The mixture was diluted with H$_2$O and extracted several times with CHCl$_3$. The pooled fractions were washed with brine and dried over MgSO$_4$, filtered and evaporated to dryness. The residue was purified by chromatography on SiO$_2$ to give N-(8-oxo-5,6,7,8-tetrahydro-naphthalen-1-yl)-acetamide (Intermediate J2) as a yellow oil. (57%, in two 2 steps)

The amide (Intermediate J2, 4.12 g, 20.3 mmol) was heated at 90° C. in 6N HCl (140 mL) for 3 h. The mixture was cooled to rt and Na$_2$CO$_3$ was added in small portions followed by addition of 2N NaOH until the mixture was at pH 8. The aqueous layer was extracted with EtOAc and the organic fractions were combined, washed with brine, dried, filtered and concentrated to give 8-amino-3,4-dihydro-2H-naphthalen-1-one (Intermediate J3) as a dark red solid 1.82 g (56%).

The amine (Intermediate J3, 1.83 g, 11.3 mmol) in CH$_2$Cl$_2$ (17 mL) was added to BF$_3$.OEt$_2$ (2.80 mL, 22.1 mmol) at −15° C. More CH$_2$Cl$_2$ (20 mL) was added to the precipitate. Next, t-butyl nitrite (1.8 mL, 12.9 mmol) in CH$_2$Cl$_2$ (20 mL) was added at −15° C. and stirred for 10 min. and at 0° C. for 20 m. The mixture was diluted with pentane (40 mL), filtered and the solids were collected, washed with ether, and dried under vacuum. The solids were placed in a flask and heated to 115° C. for 10-15 min. followed by addition of 2N NaOH and CHCl$_3$. The suspension was filtered and the aqueous phase was extracted with CHCl$_3$. The organic layers were combined, dried over MgSO$_4$, filtered and purified by chromatography on SiO$_2$ with 15% EtOAc:Hx. The product, 8-fluoro-3,4-dihydro-2H-naphthalen-1-one (Intermediate J4) was isolated; 750 mg (40%).

8-Fluoro-3,4-dihydro-2H-naphthalen-1-one (Intermediate J4) was subjected to the applicable process steps of method E to produce (Compound 35).

$^1$H NMR (300 MHz, CD$_3$OD-d$^4$) δ 7.53-7.46 (m, 1H), 7.12 (d, J=7.4 Hz, 1H), 7.02 (dd, J=8.2, 3.5 Hz, 1H), 6.61 (s, 1H), 3.12-3.04 (m, 3H), 2.88-2.78 (m, 1H), 2.62 (dd, J=8.2, 7.1 Hz, 1H), 2.20-2.11 (m, 1H), 1.86-1.75 (m, 1H).

Example J-1

Compound 111

Use of 6-amino-3,4-dihydro-2H-naphthalen-1-one (commercially available from Aldrich) in the applicable process steps in Method J produced 6-fluoro-2-(2-thioxo-2,3-dihydro-1H-imidazol-4-ylmethyl)-3,4-dihydro-2H-naphthalen-1-one (Compound 111).

$^1$H NMR (300 MHz, MeOH-d$^4$) δ 8.05-8.00 (m, 1H), 7.08-7.00 (m, 2H), 6.61 (s, 1H), 3.16-3.10 (m, 1H), 3.07-2.98 (m, 2H), 2.86-2.76 (m, 1H), 2.64 (dd, J=8.1, 7.8 Hz, 1H), 2.20-2.13 (m, 1H), 1.87-1.73 (m, 1H).

Example K

Compound 36

Procedure for the preparation of 4-(3-ethyl-4-methyl-cyclohex-3-enylmethyl)-1,3-dihydro-imidazole-2-thione (Compound 36)

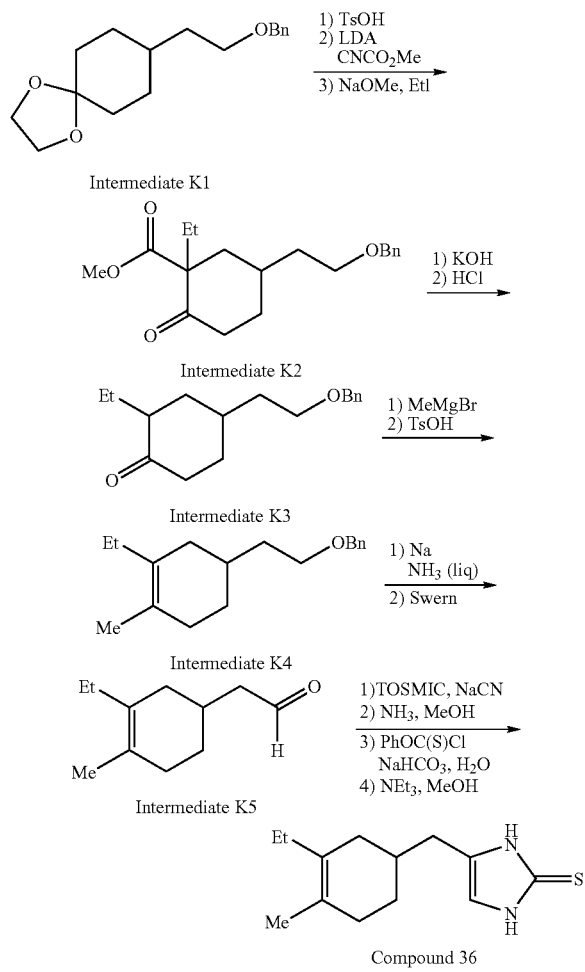

8-(2-Benzyloxy-ethyl)-1,4-dioxa-spiro[4.5]decane (Intermediate K1, 1.02 g, 3.70 mmol) (prepared in accordance with the publication Ciufolini et. al. *J. Amer. Chem. Soc.* 1991, 113, 8016, incorporated herein by reference) was dissolved in acetone (100 mL): $H_2O$ (5 mL) and reacted with TsOH (140 mg, 0.74 mmol) at 45° C. for 5 h. After a standard aqueous work-up the material was purified by chromatography on $SiO_2$ to give 4-(2-benzyloxy-ethyl)-cyclohexanone as a colorless oil (97%).

A solution of LDA (33 ml, 1.5 M in $Et_2O$) in THF (50 mL) at −78° C. was treated with 4-(2-benzyloxy-ethyl)-cyclohexanone (9.5 g, 40.2 mmol). The mixture was warmed to 0° C. over 30 min. before re-cooling to −78° C. and adding HMPA (7 mL). Methyl cyanoformate ($CNCO_2Me$, 4.1 mL, 85 mmol) was added and the mixture was stirred for 15 m before aqueous quench and work-up. The product was purified by chromatography on $SiO_2$ with 10% EtOAc:Hx. 5-(2-Benzyloxy-ethyl)-2-oxo-) cyclohexanecarboxylic acid methyl ester was isolated, 5.8 g (49%).

A mixture of 5-(2-benzyloxy-ethyl)-2-oxo-cyclohexanecarboxylic acid methyl ester in anhydrous MeOH (10 mL) was reacted with NaOMe solution (16.6 mL, 8.28 mmol) at rt for 15 min. Iodoethane (2.76 mL, 34.5 mmol) was added via syringe and the mixture was stored at rt for 48 h. Another portion of NaOMe (8.3 mmol) and EtI (35 mmol) was added and the mixture was allowed to react until the starting material was not present (by TLC). The solution was quenched with an aqueous work-up and the resultant residue was purified by chromatography to yield 5-(2-benzyloxy-ethyl)-1-ethyl-2-oxo-cyclohexanecarboxylic acid methyl ester (Intermediate K2, 1.87 g (86%). The keto-ester (Intermediate K2) was heated at 90° C. in 10% KOH (100 mL) for 10 h, then 6 h at rt. The mixture was cooled to 0° C. and acidified with HCl. The solution was warmed to 40° C. for 15 min. and then stored at rt for 2 h. The mixture was neutralized to pH 7 with NaOH and the organic material was recovered by extraction with chloroform. The resulting 4-(2-benzyloxy-ethyl)-2-ethyl-cyclohexanone (Intermediate K3) was isolated by standard work-up and used without further purification (88%). Intermediate K3 (1.36 g, 5.24 mmol) was dissolved in THF (75 mL) and treated with MeMgBr (2.62 mL, 7.9 mmol) at 0° C. and reacted at rt for 1 h. The organic material was isolated from an aqueous, acidic work-up and purified by chromatography to give 4-(2-benzyloxy-ethyl)-2-ethyl-1-methyl-cyclohexanol 1.36 g (94%). 4-(2-benzyloxy-ethyl)-2-ethyl-1-methyl-cyclohexanol (1.39 g, 5.04 mmol) and TsOH—$H_2O$ (0.48 g, 2.52 mmol) were heated to reflux in benzene (~100 mL) for 18 h in the presence of $MgSO_4$ (~250 mg). After an aqueous work-up and chromatographic purification, the product [2-(3-ethyl-4-methyl-cyclohex-3-enyl)-ethoxymethyl]-benzene (Intermediate K4) was isolated as a pale yellow oil 0.912 g (71%).

The benzyl protected alcohol (Intermediate K4, 5 mmol) in THF (20 mL) was cooled to −70° C. and $NH_3$ was condensed in the same flask (~20 mL). Na chunks were added and the mixture was allowed to stir at −70° C. for 15 min. The mixture was warmed to −30° C. for 20 min. The mixture was quenched with $NH_4Cl$ and isolated by extraction. The residue was purified by chromatography on $SiO_2$ with 25% EtOAc: Hx (99%).

The deprotected alcohol was oxidized by the standard "Swern" procedure (Mancuso, Synthesis 1981 p165, incorporated herein by reference) as follows: The alcohol (5 mmol) was added to a solution of oxalyl chloride (3.5 mL, 7.0 mmol) in $CH_2Cl_2$ (30 mL) with DMSO (0.64 mL, 9.0 mmol) at −78° C. After 40 min., $NEt_3$ (2.50 mL) was added and the mixture was warmed to rt. After standard aqueous work-up and purification, (3-ethyl-4-methyl-cyclohex-3-enyl)-acetaldehyde (Intermediate K5) was isolated (~90%).

The (Intermediate K5) was converted to 4-(3-ethyl-4-methyl-cyclohex-3-enylmethyl)-1,3-dihydro-imidazole-2-thione (Compound 36) by applying the applicable process steps of Method A.

$^1H$ NMR (300 MHz, $CD_3OD$) δ 6.54 (s, 1H), 2.40 (d, J=7.0 Hz, 2H), 2.02-1.95 (m, 4H), 1.83-1.67 (m, 4H), 1.59 (s, 3H), 1.25-1.15 (m, 1H).

Example L

Procedure for the synthesis of 1-dimethylsulfamoyl-2-t-butyldimethylsilyl imidazole

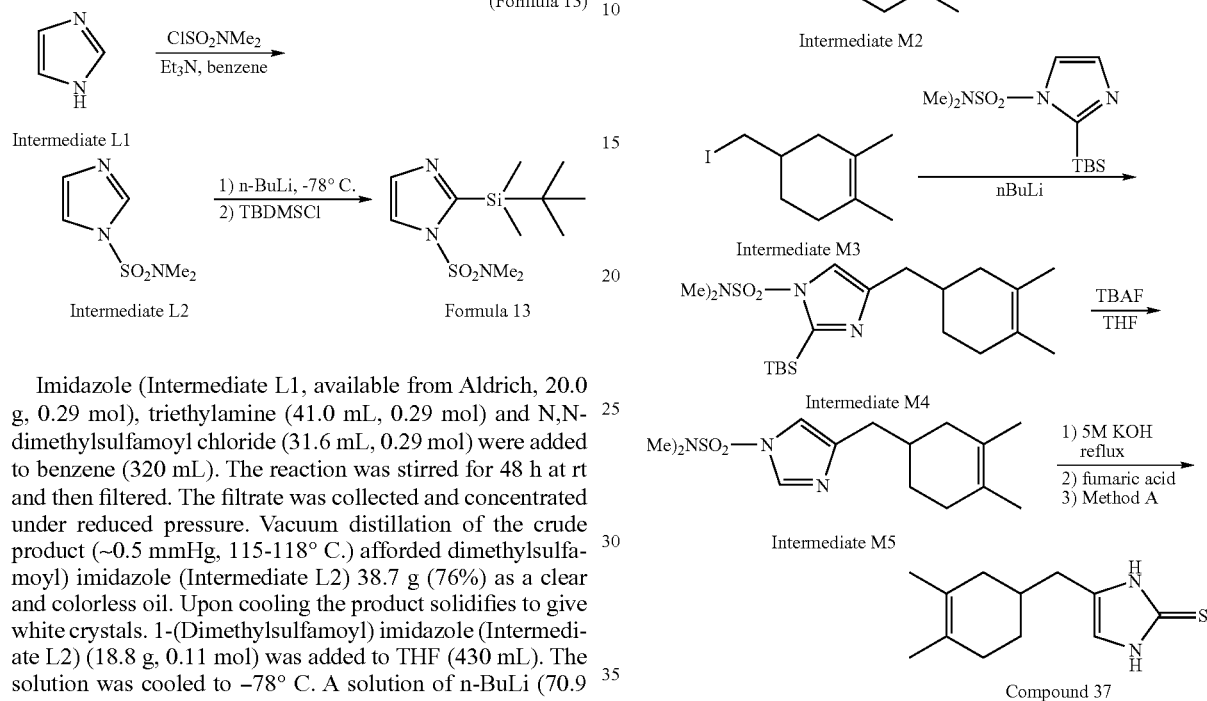

Imidazole (Intermediate L1, available from Aldrich, 20.0 g, 0.29 mol), triethylamine (41.0 mL, 0.29 mol) and N,N-dimethylsulfamoyl chloride (31.6 mL, 0.29 mol) were added to benzene (320 mL). The reaction was stirred for 48 h at rt and then filtered. The filtrate was collected and concentrated under reduced pressure. Vacuum distillation of the crude product (~0.5 mmHg, 115-118° C.) afforded dimethylsulfamoyl) imidazole (Intermediate L2) 38.7 g (76%) as a clear and colorless oil. Upon cooling the product solidifies to give white crystals. 1-(Dimethylsulfamoyl) imidazole (Intermediate L2) (18.8 g, 0.11 mol) was added to THF (430 mL). The solution was cooled to −78° C. A solution of n-BuLi (70.9 mL, 1.6 M in hexane) was added dropwise to the reaction mixture. Upon completion, the solution was stirred for 1 h at −78° C. t-Butyldimethylsilylchloride (TBSCl) (17.8 g, 0.12 mol) in THF (50 mL) was added via cannula to the mixture. After the addition was completed the reaction mixture was warmed slowly to rt and stirred for 24 h. The mixture was diluted with water and the organic layer separated. The organic phase was washed with brine and then dried over $Na_2SO_4$. The mixture was filtered and the filtrate concentrated under reduced pressure. Column chromatography on $SiO_2$ with 20% ethyl acetate/hexane afforded 1-dimethylsulfamoyl-2-t-butyldimethylsilyl imidazole (Formula 13) as a light yellow solid. Recrystallization from pentane gave 30 g (94%) of white crystals.

Example M

Compound 37

Procedure for the preparation of 4-(3,4-dimethyl-cyclohex-3-enylmethyl)-1,3-dihydro-imidazole-2-thione (Compound 37)

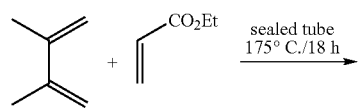

2,3-Dimethyl-1,3-butadiene (available from Aldrich, 10.2 g, 123.7 mmol), ethyl acrylate (11.1 g, 110.5 mmol) and hydroquinone (0.12 g, 1.11 mmol) were heated with stirring at 165° C. in a sealed tube for 16 h and then at 205° C. for an additional 4 h. Kugelrohr distillation of the resulting residue at 150° C. and 0.5 torr gave 14.1 g (70%) of cyclohexene ester (Intermediate M1) as an oil. To a solution of the ester (Intermediate M1, 13.6 g, 72.3 mmol) in THF (200 mL) at −78° C. was added a $LiAlH_4$ (54.3 mL, 1 M in diethyl ether). This mixture was stirred for 1 h at 20° C. and then quenched at 0° C. by careful, addition of $H_2O$ (2 mL), NaOH (2 mL of a 15% aqueous solution), and an additional portion of $H_2O$ (6 mL). The solids were filtered off and the filtrate was concentrated under reduced pressure. Kugelrohr distillation of the resulting residue at 150-180° C. and 0.5 torr gave 10.0 g (98%) of the alcohol (Intermediate M2) as a colorless volatile oil in the 0° C. bulb. To a solution of triphenyl phosphine (27.1 g, 103.5 mmol), and imidazole (7.04 g, 103.5 mmol) in anhydrous benzene (450 ml) under argon was added $I_2$ (22.8 g, 89.6 mmol) in benzene (170 ml) over a period of 10 minutes with rapid mechanical stirring. After an additional 10 min. the alcohol (Intermediate M2, 9.23 g, 65.9 mmol) in benzene (100 ml) was added to this rapidly stirring mixture over a period of 5 min. After 2 h the reaction was diluted with hexanes (800 ml) and the solids were filtered off. The organics were washed with 3 portions of $H_2O$ (800 ml), dried ($MgSO_4$), filtered and concentrated under reduced pressure. The residual solids were filtered off and the resulting oil was purified by kugelrohr distillation at 200° C. and 0.5 torr to give 12.0 g (73%) of the iodide (Intermediate M3) as a pale oil in the 0° C. bulb. To a solution of 1-N-(dimethylsulfamoyl)-2-tert-butyldimethylsilyl imidazole (Formula 13, 4.34 g, 15.0 mmol) in anhydrous THF (50 ml) at −78° C. under argon was added n-BuLi (5.76 ml, 2.5 M in hexanes). This mixture was stirred for 10 min. at −10° C. and then cooled to −20° C. before adding the iodide (Intermediate M3, 3.00 g, 12.00 mmol) in THF (25 ml) dropwise via cannula. The resulting solution was stirred for 16 h at 20° C., then quenched with saturated aqueous NaHCO$_3$ and concentrated under reduced pressure. The residues were taken up in diethyl ether and washed consecutively with H$_2$O and brine, dried (MgSO$_4$) and concentrated. Subsequent purification by chromatography on SiO$_2$ with 5-10% EtOAc:hexanes gave 0.89 g (15%) of the imidazole derivative (Intermediate M4) as a pale oil. To a solution of Intermediate M4 (0.89 g, 2.17 mmol) in anhydrous THF (25 ml) under argon was added tetrabutylammonium fluoride (2.38 ml, 1 M in THF) and the resultant solution was stirred for 1 h at 20° C. The mixture was concentrated under reduced pressure and the residues were diluted with diethyl ether and washed consecutively with saturated aqueous NaHCO$_3$ and brine, dried (MgSO$_4$) and concentrated. The residues were purified by chromatography on SiO$_2$ with 50% EtOAc:Hx to give 0.56 g (87%) of the imidazole derivative Intermediate M5 as a pale oil. To a solution of Intermediate M5 (0.53 g, 1.77 mmol) in MeOH (5 ml) was added aqueous KOH (15 ml of a 5M solution) and the mixture was heated at reflux for 32 h. The mixture was concentrated under reduced pressure, diluted with H$_2$O (5 ml) and extracted exhaustively with CHCl$_3$. The combined organic fractions were washed consecutively with H$_2$O and brine, dried (MgSO$_4$) and concentrated under reduced pressure. The product was recrystallized by stirring in MeOH with an equimolar amount of fumaric acid until all solids had disappeared followed by the addition of a small amount of diethyl ether. 4-(3,4-Dimethyl-cyclohex-3-enylmethyl)-1H-imidazole-fumarate 0.27 g (57%) was recovered as pale yellow crystals. 4-(3,4-Dimethyl-cyclohex-3-enylmethyl)-1H-imidazole-fumarate was converted to 4-(3,4-dimethyl-cyclohex-3-enylmethyl)-1,3-dihydro-imidazole-2-thione (Compound 37) by using the applicable process steps of Method A.

$^1$H NMR (300 MHz, CD$_3$OD-d$^4$): δ 6.54 (s, 1H), 2.40 (d, J=6 Hz, 2H), 1.95-1.66 (m, 5H), 1.59 (s, 6H), 1.29-1.18 (m, 2H).

Example N

Compound 38

Method N: Procedure for the preparation of 4-(4-methyl-cyclohex-3-enylmethyl)-1,3-dihydro-imidazole-2-thione (Compound 38)

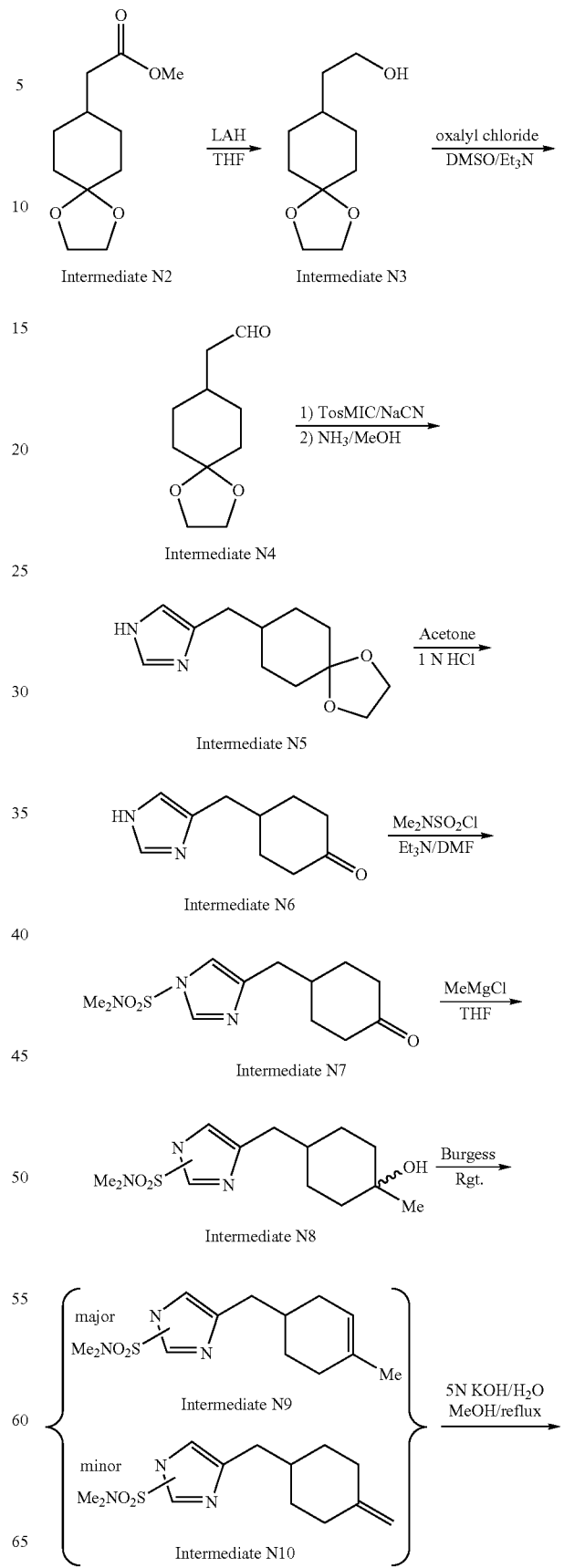

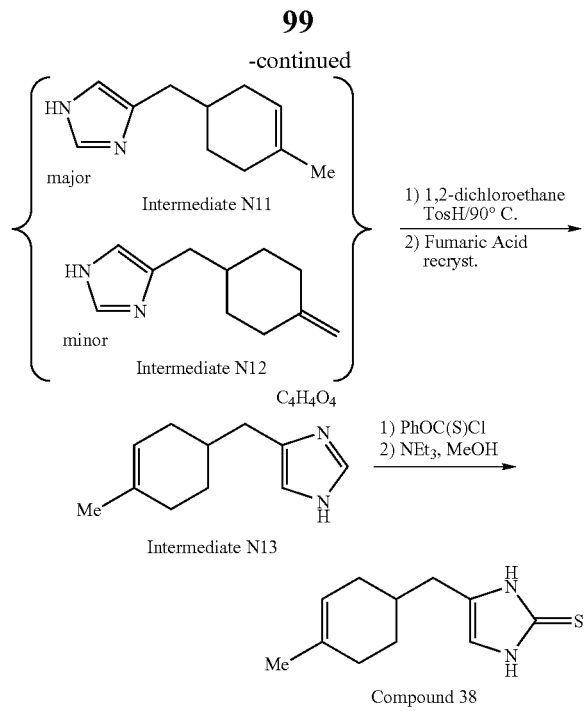

To a slurry of NaH (60% in oil) (6.92 g, 288 mmol) in anhydrous THF (1500 mL) at 0° C. under argon with vigorous mechanical stirring added the trimethyl phosphonoacetate (available from Aldrich, 52.5 g, 288 mmoL) dropwise. Stirred this mixture an additional 30 min. before adding the 1,4-cyclohexanedione mono-ethylene ketal (available from Aldrich, 41 g, 260 mmol) in THF (170 mL) dropwise. The mixture was stirred an additional 18 h at 20° C. and then concentrated under reduced pressure. This residue was taken up in diethyl ether (1 L) and washed with $H_2O$ and brine, dried ($MgSO_4$), filtered and concentrated to give 60 g (98%) of the unsaturated ester (Intermediate N1) which was used in the next reaction step without further purification. To a solution of the unsaturated ester (Intermediate N1) in EtOAc (500 mL) was added Pd (10 wt. % on activated carbon) (2.13 g). This slurry was saturated with $H_2$ by repeated evacuations and $H_2$ backfills and then stirred for 16 h under a balloon atmosphere of $H_2$. Celite (5 g) was added to the reaction, the Pd was filtered off and the filtrate was concentrated under reduced pressure to give 60 g (98%) of the saturated ester (Intermediate N2) which was used in the next step without further purification.

To a solution of $LiAlH_4$ (200 mL, 1 M in diethyl ether) at −78° C. under argon was added the unsaturated ester (Intermediate N2) in anhydrous THF (400 ml) in a slow stream with vigorous mechanical stirring. The mixture was warmed to rt and additional THF (600 mL) was added. The reaction mixture was stirred for an additional 1 h. The mixture was cooled to 0° C. and quenched by the careful, consecutive addition of $H_2O$ (7.60 ml), NaOH (7.60 ml of a 15% aqueous solution), and an additional portion of $H_2O$ (22.80 ml). The solids were filtered off and the filtrate was concentrated under reduced pressure. Subsequent purification by chromatography on $SiO_2$ with 20-50% EtOAc:hexanes gave 51 g (98%) of the alcohol (Intermediate N3) as a pale oil. To a solution of oxalyl chloride (20.65 ml, 41.29 mmol) in anhydrous $CH_2Cl_2$ (100 ml) at −78° C. under argon was added a solution of DMSO (6.72 g, 86.0 mmol) in $CH_2Cl_2$ (25 ml). After mechanical stirring for 15 min. a solution of the alcohol (Intermediate N3, 6.40 g, 34.4 mmol) in $CH_2Cl_2$ (80 ml) was added dropwise and the mixture was stirred an additional 15 min. at −78° C. before adding triethylamine (27.9 g, 275 mmol). The reaction was stirred 2 h at 20° C. and then quenched with saturated aqueous $NaHCO_3$. This mixture was extracted $CH_2Cl_2$ and the combined organic fractions were washed consecutively with $H_2O$ and brine, dried ($MgSO_4$) and concentrated under reduced pressure. The resulting solids were purified by chromatography on $SiO_2$ with 20-30% EtOAc:hexanes to give 5.08 g, (79%) of the aldehyde (Intermediate N4) as a white solid. A solution of the aldehyde (Intermediate N4, 5.08 g, 27.59 mmol) in EtOH (40 ml) was treated with tosylmethyl isocyanide (TosMIC) (5.15 g, 26.3 mmol) and NaCN (0.13 g, 2.68 mmol) at 20° C. for 3 h and then refrigerated. After 2 h of refrigeration the solids were filtered off, dissolved in anhydrous MeOH, saturated with $NH_3$ (30 ml) and heated in a sealed tube at 100° C. for 3.5 h. The reaction was then concentrated under reduced pressure and the residues were taken up in $CHCl_3$, washed consecutively with saturated aqueous $NaHCO_3$ and brine, dried ($MgSO_4$) and concentrated to a red oil. This residue was further purified by chromatography on $SiO_2$ with 5-10% MeOH (saturated with $NH_3$): $CH_2Cl_2$ to give 1.87 g (31%) of the imidazole derivative (Intermediate N5) as a pink oil. A solution of Intermediate N5 (0.55 g, 2.48 mmol) in acetone (20 ml) containing HCl (5 N, 0.5 ml) was stirred for 5 h. The reaction was concentrated under reduced pressure, the residues were taken up in $H_2O$, neutralized to pH 7 with saturated aqueous $NaHCO_3$ and extracted exhaustively with $CHCl_3$/isopropyl alcohol (3:1). The combined organic portions were washed consecutively with $H_2O$ and brine, dried ($MgSO_4$) and concentrated. Chromatography on $SiO_2$ with 5-10% MeOH (saturated with $NH_3$): $CH_2Cl_2$ gave 0.43 g (97%) of the desired ketone (Intermediate N6).

A solution of Intermediate N6 (0.20 g, 1.11 mmol) in anhydrous DMF (4 ml) under argon was treated with triethylamine (0.14 g, 1.33 mmol) and dimethylsulfamoyl chloride (0.19 g, 1.33 mmol) under argon and stirred 16 h. The solids were filtered off and the filtrate was concentrated at via kugelrohr at 100° C. and 0.5 torr. The residues were taken up in $CHCl_3$ and washed consecutively with $H_2O$ and brine, dried ($MgSO_4$) and concentrated. Chromatography on $SiO_2$ with 1-5% MeOH:$CH_2Cl_2$ gave 0.22 g (69%) of the desired imidazole derivative (Intermediate N7) as a mixture of regioisomers which were used in the next step without separation. A solution of Intermediate N7 (0.18 g, 0.62 mmol) in anhydrous THF (10 ml) under argon was treated with methylmagnesium chloride (0.32 ml, 3.0 M in THF) and the resulting mixture was stirred 16 h. The reaction was quenched with a small amount of MeOH, concentrated under reduced pressure and the residues were taken up in $H_2O$. The mixture was acidified by the dropwise addition of 1 N HCl until the solution was homogenous and then the pH was adjusted to 7 with saturated aqueous $NaHCO_3$. The organic materials were extracted into $CHCl_3$ and the combined organic portions were washed consecutively with $H_2O$ and brine, dried ($MgSO_4$) and concentrated. Chromatography on $SiO_2$ with 5% MeOH:$CH_2Cl_2$ gave 0.18 g (95%) of the cyclohexyl alcohol derivative (Intermediate N8) as a mixture of regioisomers which were carried on without separation. A solution of Intermediate N8 (0.14 g, 0.46 mmol) in anhydrous benzene (3 ml) at 0° C. under argon was treated with (methoxycarbonylsulfamoyl) triethylammonium hydroxide, inner salt (Burgess reagent) (0.12 g, 0.51 mmol) and stirred 1 h at 20° C. The reaction was concentrated under reduced pressure and subsequent purification by chromatography on $SiO_2$ with 5% MeOH:$CH_2Cl_2$ gave 0.12 g (92%) of the alkenes Intermediates N9 and N10 as a mixture of isomers which were used in the next step without separation. The mixture of isomers Intermediate N9 and N10 (0.12 g, 0.42 mmol) were refluxed in a solution composed of MeOH (2 ml) and KOH (2 ml of a 5 N solution) for 30 h. The reaction was concentrated under reduced pressure and the residues were taken up in H$_2$O and extracted exhaustively with CHCl$_3$. The combined organic portions were washed consecutively with H$_2$O and brine, dried (MgSO$_4$) and concentrated. Chromatography on SiO$_2$ with 5-10% MeOH (saturated with NH$_3$):CH$_2$Cl$_2$ gave 0.05 g (67%) of alkenes Intermediates N11 and N12 as a mixture of isomers which were used in the next step without separation.

The mixture of alkenes Intermediates N11 and N12 (45 mg, 0.26 mmol) and p-toluenesulfonic acid hydrate (63 g, 0.32 mmol) were heated at reflux in 1,2-dichloroethane (2 ml) under argon for 20 h. The reaction was concentrated under reduced pressure and the residues were purified by chromatography on SiO$_2$ with 10% MeOH (saturated with NH$_3$):CH$_2$Cl$_2$ to give the free base of imidazole derivative (Intermediate N13 as one isomer. The imidazole (Intermediate N13) was recrystallized by stirring in MeOH or THF with an equimolar amount of fumaric acid until all solids had disappeared followed by the addition of a small amount of diethyl ether and cold storage. The imidazole-fumaric acid salt was recovered as white crystals 40 mg (54%). This material was subjected to the applicable process steps of Method A to obtain 4-(4-methyl-cyclohex-3-enylmethyl)-1,3-dihydro-imidazole-2-thione (Compound 38):

$^1$H NMR (300 MHz, CD$_3$OD-d$^4$): δ 6.54 (s, 1H), 5.34 (s, 1H), 2.39 (d, J=6.4 Hz, 2H), 2.10-1.90 (m, 3H), 1.80-1.72 (m, 2H), 1.62 (s, 3H), 1.30-1.20 (m, 1H).

Example N-1

Compound 39

4-(4-Ethyl-cyclohex-3-enylmethyl)-1,3-dihydro-imidazole-2-thione (Compound 39) was prepared by using ethyl magnesium chloride instead of methyl magnesium chloride in the applicable step of Method N.

$^1$H NMR (300 MHz, CD$_3$OD-d$^4$): δ 6.54 (s, 1H), 5.34 (brs, 1H), 2.41 (d, J=6.4 Hz, 2H), 2.02-1.92 (m, 5H), 1.78-1.72 (m, 3H), 1.31-1.20 (m, 1H), 0.98 (t, J=7.5 Hz, 3H).

Example O

Compound 40

Procedure for the preparation of 4-(4-ethynyl-cyclohex-3-enylmethyl)-1,3-dihydro-imidazole-2-thione (Compound 40)

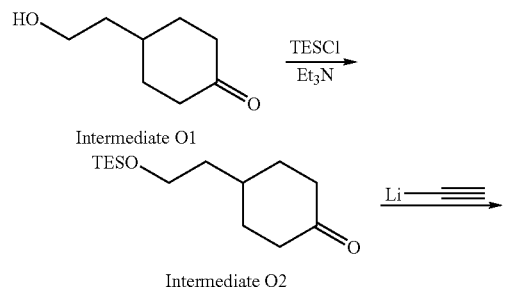
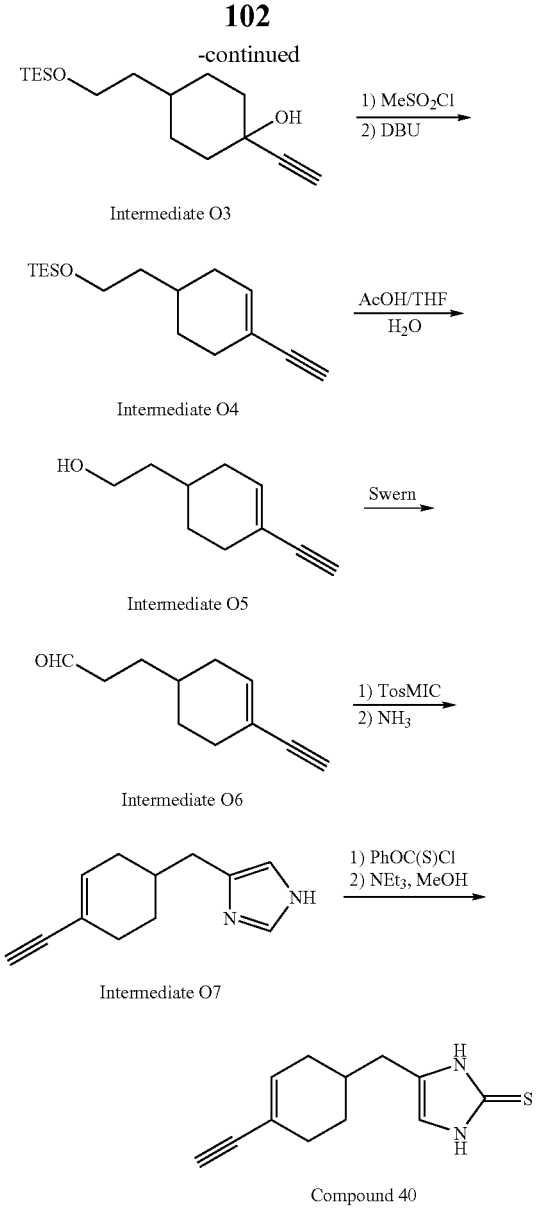

The alcohol (Intermediate O1, obtainable in accordance with the publication Ciufolini et. al. J. Amer. Chem. Soc. 1991, 113, 8016) (1.83 g, 12.88 mmol), chlorotriethylsilane (TESCl, 2.14 g, 14.17 mmol), and Et$_3$N (1.43 g, 14.17 mmol) were stirred in THF (anhydrous, 50 ml) for 16 h at 20° C. The resultant solution was taken up in Et$_2$O and washed consecutively with 5% aqueous NH$_4$Cl, saturated aqueous NaHCO$_3$, H$_2$O, brine, dried (MgSO$_4$), filtered and concentrated under reduced pressure. Subsequent purification by chromatography on SiO$_2$ with 5-10% EtOAc:hexanes gave 3.26 g (99%) of the triethylsilyl protected keto alcohol (Intermediate O2) as a pale oil.

To a solution of the keto alcohol (Intermediate O2, 3.38 g, 13.22 mmol) in THF (anhydrous, 50 ml) at 0° C. under argon was added ethynyl magnesium chloride (44.1 ml of a 0.5 M solution in THF). This mixture was allowed to stir at 20° C. for 6 h and was then recooled to 0° C. and quenched with H$_2$O. The resultant solution was taken up in EtOAc and washed consecutively with saturated aqueous NH$_4$Cl, saturated aqueous NaHCO$_3$, H$_2$O, brine, dried (MgSO$_4$), filtered and concentrated under reduced pressure. Subsequent purification by chromatography on SiO$_2$ with 10-15% EtOAc:hexanes gave 2.99 g (80%) of the alcohol (Intermediate O3) as a pale oil.

To a solution of Intermediate O3 (2.94 g, 10.44 mmol) in THF (anhydrous, 50 ml) at 0° C. under argon was added 1,8-diazabicyclo[5.4.0]undec-7-ene (DBU) (7.63 g, 50.12 mmol) and MeSO$_2$Cl (3.71 g, 32.36 mmol). This mixture was allowed to stir at 20° C. for 20 h and was then recooled to 0° C. and quenched with MeOH. The mixture was concentrated under reduced pressure and the residues were taken up in Et$_2$O and washed consecutively with saturated aqueous NH$_4$Cl, saturated aqueous NaHCO$_3$ and brine, dried (MgSO$_4$) and concentrated under reduced pressure. The residues were purified by chromatography on SiO$_2$ with 2% EtOAc:hexanes to give 0.88 g of the enyne (Intermediate O4) which was used in the next step without further purification.

The enyne (Intermediate O4, 0.88 g, 3.34 mmol) was stirred in a solution of THF/AcOH/H$_2$O (4 ml in a ratio of 8:8:1) at 20° C. for 3 h. The mixture was concentrated under reduced pressure and the residues were taken up in Et$_2$O and washed consecutively with saturated aqueous K$_2$CO$_3$, H$_2$O and brine, dried (MgSO$_4$) and concentrated under reduced pressure. The residues were purified by chromatography on SiO$_2$ with 30% EtOAc:hexanes to give 0.50 g of the alcohol (Intermediate O5) which was used in the next step without further purification.

To a solution of oxalyl chloride (2 ml of a 2.0 M solution in CH$_2$Cl$_2$) in CH$_2$Cl$_2$ (anhydrous, 10 ml) at −78° C. under argon added DMSO (0.65 g, 8.33 mmol) in CH$_2$Cl$_2$ (anhydrous, 5 ml) dropwise via cannula. The reaction was stirred for 15 min. after addition was complete and then the alcohol (Intermediate O5, 0.50 g, 3.33 mmol) was added in CH$_2$Cl$_2$ (anhydrous, 10 ml) dropwise via cannula and stirred for an additional 15 minutes before adding neat Et$_3$N (2.70 g, 26.66 mmol). The reaction was allowed to warm to 20° C. and stirred 2 h and then quenched with saturated aqueous NaHCO$_3$. This mixture was extracted with CH$_2$Cl$_2$. and the combined organic fractions were washed with H$_2$O and brine, dried (MgSO$_4$) and concentrated under reduced pressure. The residues were purified by chromatography on SiO$_2$ with 15% EtOAc:hexanes to give 0.32 g (65%) of the aldehyde (Intermediate O6).

A solution of the aldehyde Intermediate O6 (0.38 g, 2.54 mmol) in EtOH (anhydrous, 1.5 ml) was treated with tosylmethyl isocyanide (TosMIC) (0.52 g, 2.67 mmol) and NaCN (0.013 g, 0.25 mmol) at 20° C. for 2 h. This mixture was concentrated under reduced pressure and the resulting residue was taken up in MeOH saturated with NH$_3$ (anhydrous, 10 ml) and heated in a sealed tube at 100° C. for 3.5 h. The reaction was then concentrated under reduced pressure and purified by chromatography on SiO$_2$ with 10% MeOH:CH$_2$Cl$_2$ to give 0.16 g (35%) of the imidazole derivative (Intermediate O7) as an amber oil.

4-(4-Ethynyl-cyclohex-3-enylmethyl)-1,3-dihydro-imidazole-2-thione (Compound 40) was prepared by subjecting the imidazole derivative Intermediate 7 to the applicable process steps of Method A.

$^1$H NMR (300 MHz, CD$_3$OD-d$^4$): δ 6.57 (s, 1H), 6.08 (brs, 1H), 3.10 (s, 1H), 2.43 (d, J=6.4 Hz, 2H), 2.18-2.14 (m, 3H), 1.85-1.75 (m, 3H), 1.30-1.25 (m, 1H).

Example ONE

Method ONE: procedure for the preparation of 4-[(2-phenylcyclopent-2-en-1-yl)methyl]-1,3-dihydro-2H-imidazole-2-thione (Compound 112)

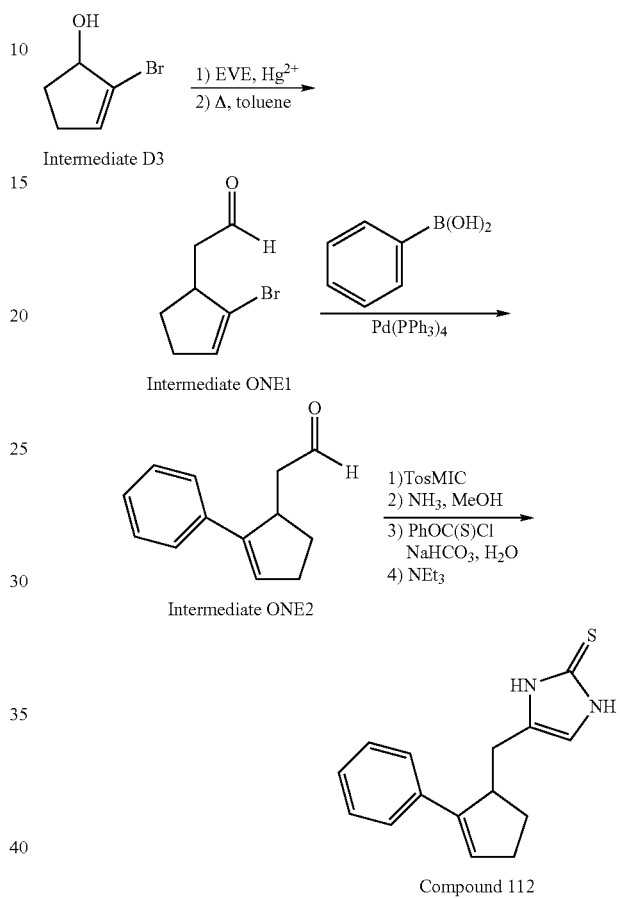

A solution of 2-bromo-cyclopent-2-enol (Intermediate D3) (21.7 g, 133.1 mmol) in ethyl vinyl ether (300 mL) was treated with Hg(OAc)$_2$ (31.8 g, 99 mmol) at rt for 60 h. The mixture was quenched with 5% NaOH (150 mL) and filtered through celite. The residue was concentrated to yield 1-bromo-5-vinyloxy-cyclopentene as a pale yellow oil, 14.2 g (46%). 1-Bromo-5-vinyloxy-cyclopentene (14.1 g, 74.4 mmol) in toluene was heated in a re-sealable tube at 130° C. for 24 h. (2-Bromo-cyclopent-2-enyl)-acetaldehyde (Intermediate ONE1) was isolated after flash chromatography on silica gel with hexanes to 5% ethyl acetate:hexanes, 10.4 g (74%).

(2-Bromo-cyclopent-2-enyl)-acetaldehyde (Intermediate ONE1) (1.85 g, 9.32 mmol) in benzene (70 mL) was treated with Na$_2$CO$_3$ (14.0 mL, 2M in H$_2$O.) and phenylboronic acid (2.27 g, 18.6 mmol) in EtOH (40 mL). Tetrakis(triphenylphosphine) palladium(0), Pd(PPh$_3$)$_4$ catalyst (1.61 g, 1.40 mmol) was added and the mixture was heated to 80° C. for 3.5 h. until no starting material remained. The benzene was replaced with diethyl ether and the mixture was filtered through celite. The filtrate was washed with sat. K$_2$CO$_3$, brine and dried over MgSO$_4$. Pure (2-phenyl-cyclopent-2-enyl)-acetaldehyde (Intermediate ONE2) 1.07 g (62%) was isolated by chromatography on silica gel. Use of (2-phenyl-cyclopent- 2-enyl)-acetaldehyde (Intermediate ONE2) in Method A (without formation of the fumarate) produced 4-[(2-phenyl-cyclopent-2-en-1-yl)methyl]-1,3-dihydro-2H-imidazole-2-thione (Compound 112).

¹H NMR (300 MHz, CDCl₃) δ 11.5 (s, 1H), 11.3 (s, 1H), 7.39-7.16 (m, 5H), 6.32 (s, 1H), 6.07 (s, 1H), 3.46 (brs, 1H), 2.78 (dd, J=15.1, 3.4 Hz, 1H), 2.43-2.28 (m, 3H), 2.10 (dd, J=13.2, 8.2 Hz, 1H) 1.82-1.67 (m, 1H).

Example ONE-1

Compound 113

Use of 4-methylphenylboronic acid (commercially available from Aldrich) in Method ONE produced 4-[2-(4-methylphenyl)cyclopent-2-en-1-yl]methyl-1,3-dihydro-2H-imidazole-2-thione (Compound 113).

¹H NMR (300 MHz, CDCl₃) δ 11.6 (s, 1H), 11.5 (s, 1H), 7.33-7.12 (m, 4H), 6.32 (s, 1H), 6.02 (s, 1H), 3.50-3.40 (m, 1H), 2.80-2.74 (m, 1H), 2.38 (brs, 3H), 2.29 (s, 3H), 2.11-2.00 (m, 1H), 1.74-1.70 (m, 1H).

Example ONE-2

Compound 114

Use of 4-methoxyphenylboronic acid (commercially available from Aldrich) in Method ONE produced 4-[2-(4-methoxyphenyl)cyclopent-2-en-1-yl]methyl-1,3-dihydro-2H-imidazole-2-thione (Compound 114).

¹H NMR (300 MHz, CDCl₃) δ 11.8 (s, H), 11.6 (s, 1H), 7.36 (d, J=9 Hz, 2H), 6.85 (d, J=9 Hz, 2H), 6.33 (s, 1H), 5.95 (s, 1H), 3.75 (s, 3H), 3.41 (brs, 1H), 2.82-2.78 (m, 1H), 2.36 (s, 1H), 2.35-2.30 (m, 2H), 2.11-2.00 (m, 1H), 1.78-1.70 (m, 1H).

Example ONE-3

Compound 115

Use of 4-cyanophenylboronic acid (commercially available from Aldrich) in Method ONE produced 4-[5-(2-thioxo-2,3-dihydro-1H-imidazol-4-ylmethyl)-cyclopent-1-enyl]-benzonitrile (Compound 115).

¹H NMR (300 MHz, DMSO-d⁶) δ 12.0 (s, 1H), 11.7 (s, 1H), 7.81-7.75 (m, 4H), 6.55 (s, 1H), 6.50 (s, 1H), 3.41 (brs, 2H), 2.51-2.42 (m, 2H), 2.16-1.95 (m, 2H), 1.76-1.74 (m, 1H).

Example ONE-4

Compound 116

Use of 3-nitrophenylboronic acid (commercially available from Aldrich) in Method ONE produced 4-[2-(3-nitrophenyl)cyclopent-2-en-1-yl]methyl-1,3-dihydro-2H-imidazole-2-thione (Compound 116).

¹H NMR (300 MHz, CDCl₃) δ 12.1 (s, 1H), 11.5 (s, 1H), 8.20 (s, 1H), 7.96 (d, J=12 Hz, 1H), 7.73 (d, J=9 Hz, 1H), 7.47 (t, J=6 Hz, 1H), 6.41 (s, 1H), 6.22 (s, 1H), 3.50 (brs, 1H), 2.76-2.70 (m, 1H), 2.45-2.30 (m, 3H), 2.13-2.00 (m, 1H), 1.82-1.76 (m, 1H).

Example TWO

Method TWO: procedure for the preparation of (+)-4-[(S*)-2-(3-fluorophenyl)-2-cyclopent-2-enylmethyl-1,3-dihydro-imidazole-2-thione (Compound 117)

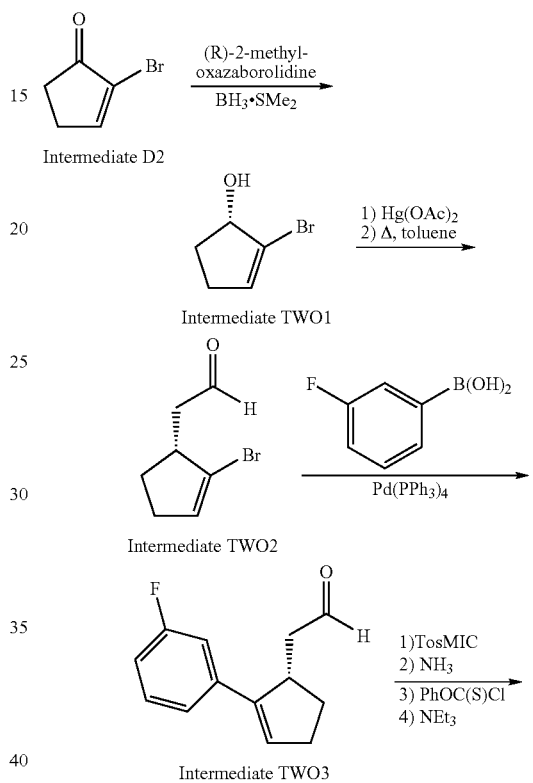

Use of (R)-2-methyl-oxazaborolidine catalyst (20 mol %) (commercially available from Aldrich) with BH₃.SMe₂ in the reduction of Intermediate D2 (see: Corey, E. J.; Chen C.-P.; Reichard, G. A. Tetrahedron Lett. 1989, 30, 6275 and Xavier, L. C. et al; Organic Syntheses 1996, 74, 50 incorporated herein by reference) produced (−)-(S)-2-bromo-cyclopent-2-enol (Intermediate TWO1). Use of optically enriched (−)-(S)-2-bromo-cyclopent-2-enol (Intermediate TWO1) and substituting 3-fluorophenylboronic acid (commercially available from Aldrich) in Method TWO produced (+)-4-[(S*)-2-(3-fluorophenyl)-cyclopent-2-enylmethyl]-1,3-dihydro-imidazole-2-thione (Compound 117).

opt. rotation [α]$_D^{20}$ +116.3° (c 2.45 in CHCl₃)

¹H NMR same as Compound 129 (see below)

Example TWO-1

Compound 118

Use of (R)-2-methyl-oxazaborolidine catalyst with BH$_3$.SMe$_2$ for the reduction step and substituting 4-fluorophenylboronic acid (commercially available from Aldrich) in Method TWO produced (+)-4-[(S*)-2-(4-fluorophenyl)-cyclopent-2-enylmethyl]-1,3-dihydro-imidazole-2-thione (Compound 118).

opt. rotation $[\alpha]_D^{20}$ +90.0° (c 4.07 in MeOH)

Chiral HPLC isolation of Compound 118: From racemic Compound 123 (see Example THREE) isolation of the 2$^{nd}$ eluting enantiomer from the following conditions: Chiral HPLC; 10% isopropyl alcohol/hexane at 1 mL/m on a Chiralcel OJ 4.6×250 mm column; detector uv at 220 nm; rt; isocratic; collect 14.7 m (peak two). 96% ee; opt. rotation $[\alpha]_D^{20}$ +75° (c 1.03 in MeOH)

$^1$H NMR same as Compound 123 (see below)

Example TWO-2

Compound 119

Use of (R)-2-methyl-oxazaborolidine catalyst with BH$_3$.SMe$_2$ for the reduction step and substituting 3,5-difluorophenylboronic acid (commercially available from Aldrich) in Method TWO produced (+)-4-[(S*)-2-(3,5-difluorophenyl)-cyclopent-2-enylmethyl]-1,3-dihydro-imidazole-2-thione (Compound 119).

opt. rotation $[\alpha]_D^{20}$ +87.8° (c 0.90 in MeOH)

$^1$H NMR same as compound 126.

Example TWO-3

Compound 120

Use of (S)-2-methyl-oxazaborolidine catalyst (20 mol %) with BH$_3$.SMe$_2$ in the reduction of Intermediate D2 produced (+)-(R)-2-bromo-cyclopent-2-enol. Use of optically enriched (+)-(R)-2-bromo-cyclopent-2-enol and substituting 3-fluorophenylboronic acid (commercially available from Aldrich) in Method TWO produced (−)-4-[(R*)-2-(3-fluorophenyl)-cyclopent-2-enylmethyl]-1,3-dihydro-imidazole-2-thione (Compound 120).

opt. rotation $[\alpha]_D^{20}$ −108.9 (c=1.24 in CHCl$_3$)

Chiral HPLC isolation of Compound 120: same as for Compound 18 (see above) collect 12.6 m (peak one). 99% ee; opt. rotation $[\alpha]_D^{20}$ −86° (c 1.10 in MeOH).

$^1$H NMR same as Compound 129 (see below).

Example TWO-4

Compound 121

Use of (s)-2-methyl-oxazaborolidine catalyst with BH$_3$.SMe$_2$ for the reduction step and substituting 4-fluorophenylboronic acid (commercially available from Aldrich) in Method TWO produced (−)-4-[(R*)-2-(4-fluorophenyl)-cyclopent-2-enylmethyl]-1,3-dihydro-imidazole-2-thione (Compound 121).

opt. rotation $[\alpha]_D^{20}$ −85.6° (c 1.24 in MeOH)

$^1$H NMR same as Compound 123.

Example TWO-5

Compound 122

Use of (S)-2-methyl-oxazaborolidine catalyst with BH$_3$.SMe$_2$ for the reduction step and substituting 3,5-difluorophenylboronic acid (commercially available from Aldrich) in Method TWO produced (−)-4-[(R*)-2-(3,5-difluorophenyl)-cyclopent-2-enylmethyl]-1,3-dihydro-imidazole-2-thione (Compound 122).

opt. rotation $[\alpha]_D^{20}$ −96.1° (c 1.32 in MeOH)

$^1$H NMR same as Compound 126.

Example THREE

Method THREE: Procedure for preparation of 4-[2-(4-fluoro-phenyl)-cyclopent-2-enylmethyl]-1,3-dihydro-imidazole-2-thione (Compound 123)

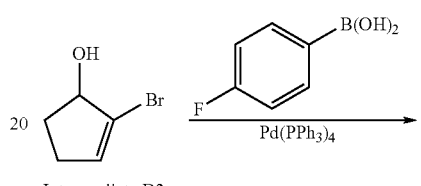

Intermediate D3

Intermediate THREE1

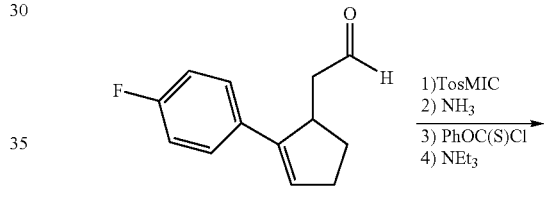

Intermediate THREE2

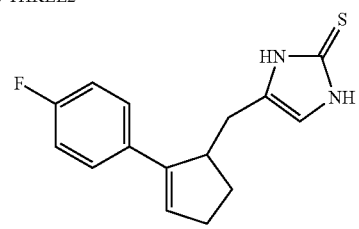

Compound 123

2-Bromo-cyclopent-2-enol (Intermediate D3) (1.1 g, 6.7 mmol) and the 4-fluoroboronic acid (commercially available from Aldrich) (1.09 g, 7.8 mmol) in dioxane (20 mL) was treated with 2M Na$_2$CO$_3$ (14 mL) and degassed. Pd(PPh$_3$)$_4$ (0.4 g, ~5 mol %) was added to the mixture and degassed with N$_2$ gas for 15 m. The reaction mixture was heated to reflux for one hour, cooled to rt and diluted with ether and water. The aqueous layer was extracted with ether. The combined layers were washed with brine and dried over Na$_2$SO$_4$. The suspension was filtered and freed of solvent. The residue was purified by chromatography on SiO$_2$ to give 2-(4-fluorophenyl)-cyclopent-2-enol (Intermediate THREE1).

Use of 2-(4-fluorophenyl)-cyclopent-2-enol (Intermediate THREE1) in Method A produced 4-[2-(4-fluoro-phenyl)-cyclopent-2-enylmethyl]-1,3-dihydro-imidazole-2-thione (Compound 123).

$^1$H NMR (500 MHz, CDCl$_3$) δ 11.3 (s, 1H), 11.1 (s, 1H), 7.42-7.38 (m, 2H), 7.06-7.00 (m, 2H), 6.37 (s, 1H), 6.025 (s,

1H), 3.43 (s, 1H), 2.79-2.72 (m, 1H), 2.42-2.29 (m, 3H), 2.16-2.08 (m, 1H), 1.78-1.76 (m, 1H).

Example THREE-1

Compound 124

Use of 3,4-difluorophenylboronic acid (commercially available from Aldrich) in Method THREE produced 4-[2-(3, 4-difluorophenyl)-cyclopent-2-enylmethyl]-1,3-dihydro-imidazole-2-thione (Compound 124).

$^1$H NMR (300 MHz, MeOD-d$^4$) δ 7.41-7.34 (m, 1H), 7.24-7.15 (m, 2H), 6.49 (s, 1H), 6.15 (s, 1H), 3.40 (brs, 1H), 2.73-2.68 (m, 1H), 2.48-2.42 (m, 2H), 2.35-2.27 (m, 1H), 2.20-2.05 (m, 1H), 1.90-1.78 (m, 1H).

Example THREE-2

Compound 125

Use of 5-chlorothiophene-2-boronic acid (commercially available from Aldrich) in Method THREE produced 4-[2-(5-chloro-thiophen-2-yl)-cyclopent-2-enylmethyl]-1,3-dihydro-imidazole-2-thione (Compound 125).

$^1$H NMR (300 MHz, MeOD-d$^4$) δ 6.84 (s, 2H), 6.52 (s, 1H), 5.96 (s, 1H), 3.29 (brs, 1H), 2.82-2.76 (m, 1H), 2.44-2.36 (m, 3H), 2.14-2.00 (m, 1H), 1.86-1.77 (m, 1H).

Example FOUR

Method FOUR: Procedure for the preparation of 4-[2-(3,5-difluorophenyl)-cyclopent-2-enylmethyl]-1,3-dihydro-imidazole-2-thione (Compound 126)

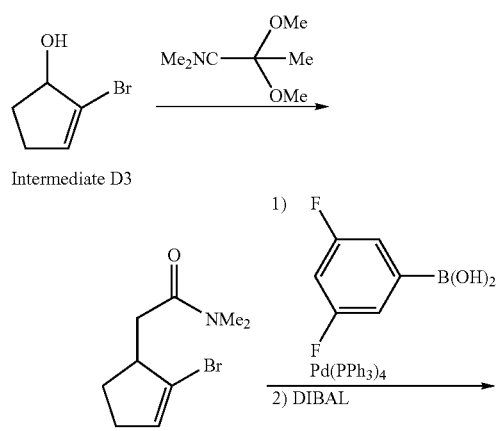

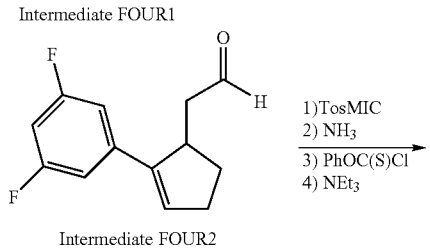

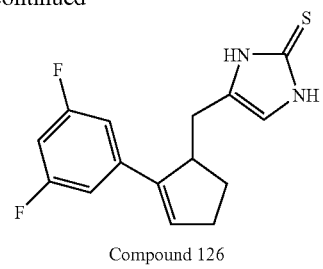

Compound 126

2-Bromo-cyclopent-2-enol (Intermediate D3) (2.18 g, 13.4 mmol) and N,N-dimethylacetamide dimethyl acetal (3.5 mL, 21.5 mmol) in m-xylene (~20 mL) were heated to 140° C. for 14 h. The mixture was freed of solvent and the residue was purified on a column of silica gel with 30% to 50% EtOAc:hexanes to give 2-(2-bromo-cyclopent-2-enyl)-N,N-dimethyl-acetamide (Intermediate FOUR1) 1.95 g (63%) as a brown oil.

2-(2-Bromo-cyclopent-2-enyl)-N,N-dimethyl-acetamide (Intermediate FOUR1) (1.16 g, 5 mmol) in benzene (36 mL), and Na$_2$CO$_3$ (5 mL, 2M) was treated with a solution of 3,5-difluoroboronic acid (1.1 g, 6.96 mmol) in EtOH (25 mL). Tetrakis(triphenylphosphine) palladium(0) [Pd(PPh$_3$)$_4$] (0.3 g, 5 mol %) was added and the degassed mixture was heated to 80° C. for 1.5 h. The mixture was diluted with water and extracted with diethyl ether (2×). The combined organic layers were dried over MgSO$_4$, filtered and evaporated to dryness. The oil was purified by column chromatography on silica gel with 40% EtOAc:hexane to give 2-[2-(3,5-difluoro-phenyl)-cyclopent-2-enyl]-N,N-dimethyl-acetamide 0.93 g (70%) as a light yellow solid. This amide was reduced with DIBAL (14.2 mL, IM in hexane) in Et$_2$O:THF (5:1) (60 mL) at −78° C. over 1.5 h. The mixture was subjected to an aqueous work-up with Rochelle's salt solution. The aldehyde, 2-(3,5-difluoro-phenyl)-cyclopent-2-enyl]-acetaldehyde (Intermediate FOUR2) was isolated in an approximate yield of 70%.

Use of Intermediate FOUR2 and 3,5-difluorophenylboronic acid (commercially available from Aldrich) in Method A produced 4-[2-(3,5-difluorophenyl)-cyclopent-2-enylmethyl]-1,3-dihydro-imidazole-2-thione (Compound 126).

$^1$H NMR (300 MHz, MeOD-d$^4$) δ 7.11-7.08 (m, 2H), 6.82-6.77 (m, 1H), 6.26 (s, 1H), 3.40 (brs, 1H), 2.72-2.69 (m, 1H), 2.49-2.41 (m, 2H), 2.34-2.29 (m, 1H), 2.16-2.08 (m, 1H), 1.84-1.79 (m, 1H).

Example FIVE

Method FIVE: Procedure for the preparation of 4-[2-(2-fluorophenyl)-cyclopent-2-enylmethyl]-1,3-dihydro-imidazole-2-thione (Compound 127)

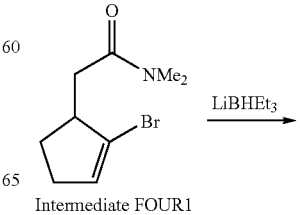

111
-continued

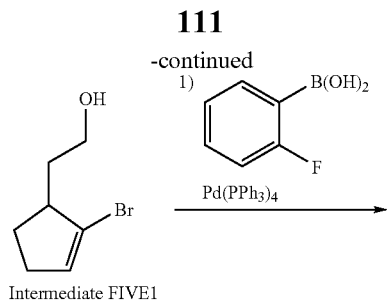
Intermediate FIVE1

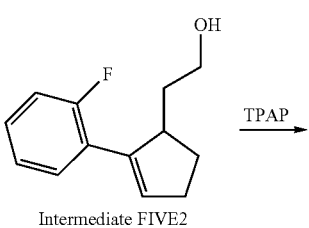
Intermediate FIVE2

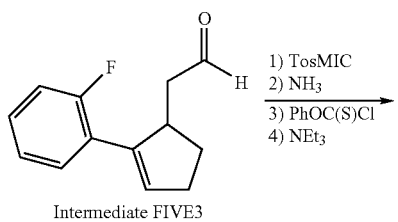
Intermediate FIVE3

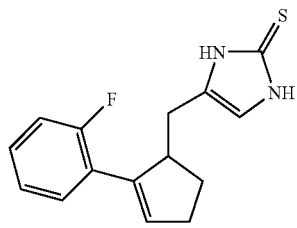
Compound 127

112

2-(2-Bromo-cyclopent-2-enyl)-N,N-dimethyl-acetamide (Intermediate FOUR1) (1.93 g, 8.3 mmol) in THF (50 mL) was reacted with lithium triethylborohydride (19 mL, 1 M in THF) at 0° C. for 1 h. The mixture was treated with an aqueous work-up and the resultant alcohol was purified by column chromatography to give 0.92 g of 2-(2-bromo-cyclopent-2-enyl)-ethanol Intermediate FIVE1.

2-(2-Bromo-cyclopent-2-enyl)-ethanol Intermediate FIVE1 (1.21 g, 6.33 mmol) in benzene (40 mL), and $Na_2CO_3$ (7 mL, 2M) was treated with a solution of 2-fluorophenylboronic acid (1.08 g, 7.72 mmol) in EtOH (28 mL). Tetrakis (triphenylphosphine) palladium(0), $Pd(PPh_3)_4$ (0.38 g, 5 mol %) was added and the mixture was heated to 80° C. for 1.5 h. The mixture was diluted with water and extracted with diethyl ether (2×). The combined organic layers were dried over $MgSO_4$, filtered and evaporated to dryness. The oil was purified by column chromatography on silica gel with 30% EtOAc:hexane to give 2-[2-(2-fluoro-phenyl)-cyclopent-2-enyl]-ethanol Intermediate FIVE2 (1.21 g).

The alcohol Intermediate FIVE2 (1.2 g, 5.87 mmol) in acetonitrile (20 mL) was mixed with 4 Å molecular sieves (1.21 g), 4-methyl morpholine-N-oxide (1.38 g, 11.8 mmol) and TPAP: tetrapropylammonium perruthenate (0.22 g, 10 mol % catalyst) at rt for 1 h. The aldehyde, [2-(2-fluoro-phenyl)-cyclopent-2-enyl]-acetaldehyde (Intermediate FIVE3) was purified on a column of silica gel eluted with 10% EtOAc:Hexane (~25%).

Use of [2-(2-fluoro-phenyl)-cyclopent-2-enyl]-acetaldehyde (Intermediate FIVE3) in Method A produced 4-[2-(2-fluorophenyl)-cyclopent-2-enylmethyl]-1,3-dihydro-imidazole-2-thione (Compound 127).

$^1$H NMR (300 MHz, MeOD-d$^4$) δ 7.41-7.36 (m, 1H), 7.27-7.20 (m, 1H), 7.16-7.63 (m, 2H), 6.42 (s, 1H), 6.15 (s, 1H), 3.52 (m, 1H), 2.67-2.60 (m, 1H), 2.52-2.37 (m, 2H), 2.34-2.26 (m, 1H), 2.21-2.08 (m, 1H), 1.80-1.69 (m, 1H).

Example Six

Method SIX: Procedure for the preparation of 4-[2-(2,4-difluorophenyl)-cyclopent-2-enylmethyl]-1,3-dihydro-imidazole-2-thione (Compound 128)

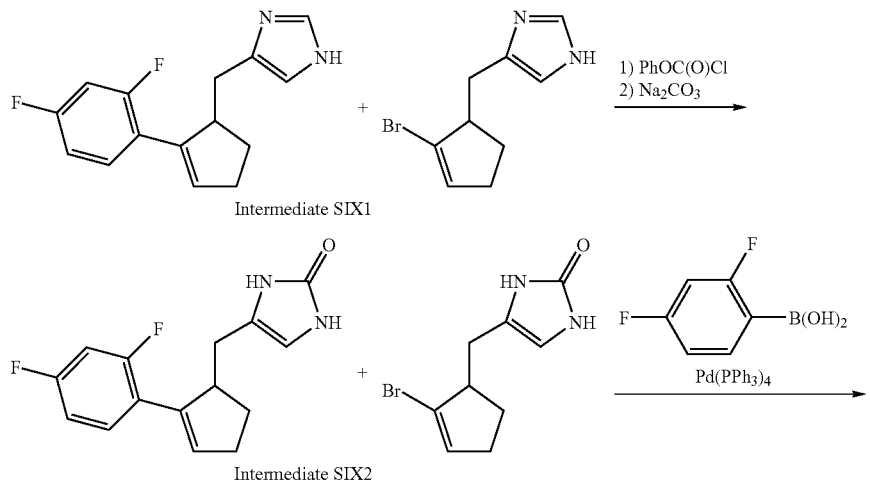

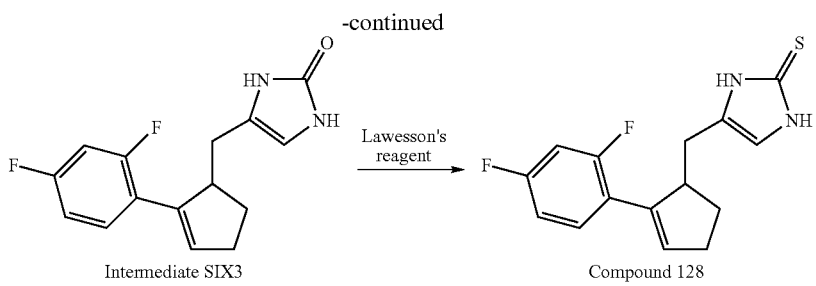

Intermediate SIX3 → Compound 128 (Lawesson's reagent)

A mixture of two compounds: 4-[2-(2,4-difluoro-phenyl)-cyclopent-2-enylmethyl]-1H-imidazole and 4-(2-bromo-cyclopent-2-enylmethyl)-1H-imidazole (Intermediate SIX1) (produced with procedures as in Method FIVE, but without complete coupling of the boronic acid) were subjected to the reaction found in Method P. The mixture, Intermediate SIX2 was subjected to the coupling reaction as follows. Intermediate SIX2 (0.25 g, ~1.1 mmol) in benzene (8 mL), and Na$_2$CO$_3$ (1 mL, 2M) was treated with a solution of 2,4-difluoroboronic acid (commercially available from Aldrich) (0.31 g) in EtOH (6 mL). Tetrakis(triphenylphosphine) palladium(0) Pd(PPh$_3$)$_4$ (~5 mol %) was added and the mixture was heated to 80° C. for 3 h. The mixture was diluted with water and extracted with diethyl ether (2×). The combined organic layers were dried over MgSO$_4$, filtered and evaporated to dryness. The oil was purified by column chromatography on silica gel with 30% EtOAc:hexane to give Intermediate SIX3 (0.14 g).

Finally, Intermediate SIX3 was converted to the thione compound by use of Lawesson's reagent in the standard fashion as follows. Intermediate SIX3 (0.14 g, 0.5 mmol) and Lawesson's reagent [2,4-bis(4-methoxyphenyl)-1,3-dithia-2,4-diphosphetane-2,4-disulfide] (commercially available from Aldrich) (0.45 g, ~1.1 mmol) in dioxane were heated at reflux for several hours. The mixture was poured onto silica gel and the solvent was removed under vacuum. The crude material was placed onto a column of silica and the product was eluted with 4% NH$_3$-MeOH: CH$_2$Cl$_2$. This method produced 4-[2-(2,4-difluorophenyl)-cyclopent-2-enylmethyl]-1,3-dihydro-imidazole-2-thione (Compound 128).

$^1$H NMR (300 MHz, MeOD-d$^4$) δ 7.44-7.36 (m, 1H), 6.95-6.88 (m, 2H), 6.42 (s, 1H), 6.12 (s, 1H), 3.47 (brs, 1H), 2.64-2.58 (m, 1H), 2.51-2.44 (m, 2H), 2.35-2.26 (m, 1H), 2.20-2.08 (m, 1H), 1.79-1.69 (m, 1H).

Example Seven

Method SEVEN: Procedure for the preparation of produced 4-[2-(3-fluorophenyl)-cyclopent-2-enylmethyl]-1,3-dihydro-imidazole-2-thione (Compound 129)

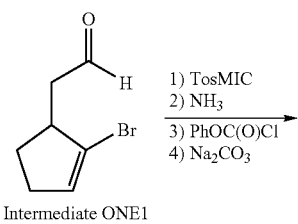

Intermediate ONE1
1) TosMIC
2) NH$_3$
3) PhOC(O)Cl
4) Na$_2$CO$_3$

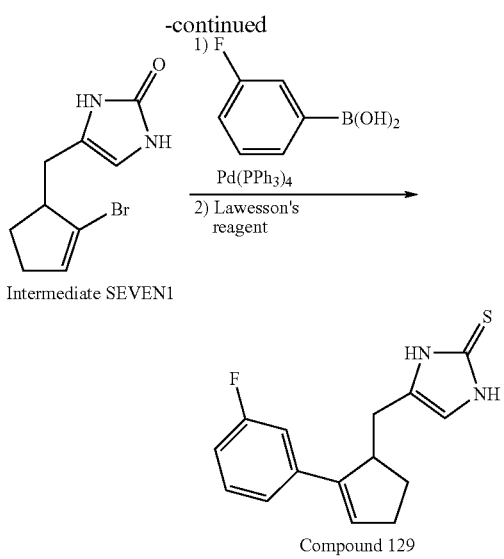

Intermediate SEVEN1
1) F-C$_6$H$_4$-B(OH)$_2$, Pd(PPh$_3$)$_4$
2) Lawesson's reagent Compound 129

(2-Bromo-cyclopent-2-enyl)-acetaldehyde (Intermediate ONE1) was transformed via reactions as described in Method P to 4-(2-bromo-cyclopent-2-enylmethyl)-1,3-dihydro-imidazol-2-one (IntermediateSEVEN1). Intermediate SEVEN1 was processed according to Method SIX into 4-[2-(3-fluorophenyl)-cyclopent-2-enylmethyl]-1,3-dihydro-imidazole-2-thione (Compound 129).

$^1$H NMR (500 MHz, MeOD-d$^4$) δ 7.35-7.30 (m, 1H), 7.27 (d, J=8.5 Hz, 1H), 7.21 (d, J=10.5 Hz, 1H), 6.97-6.93 (m, 1H), 6.49 (s, 1H), 6.19 (s, 1H), 3.43 (brs, 1H), 2.73-2.70 (m, 1H), 2.50-2.40 (m, 2H), 2.33-2.28 (m, 1H), 2.17-2.09 (m, 1H), 1.84-1.78 (m, 1H).

Example Eight

Method EIGHT: Procedure for the preparation of 4-[2-(2,5-difluorofluorophenyl)-cyclopent-2-enylmethyl]-1,3-dihydro-imidazole-2-thione (Compound 130)

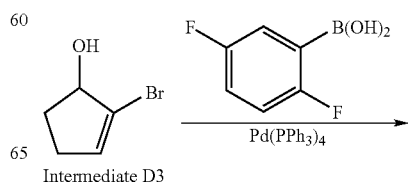

Intermediate D3 + Pd(PPh$_3$)$_4$

-continued

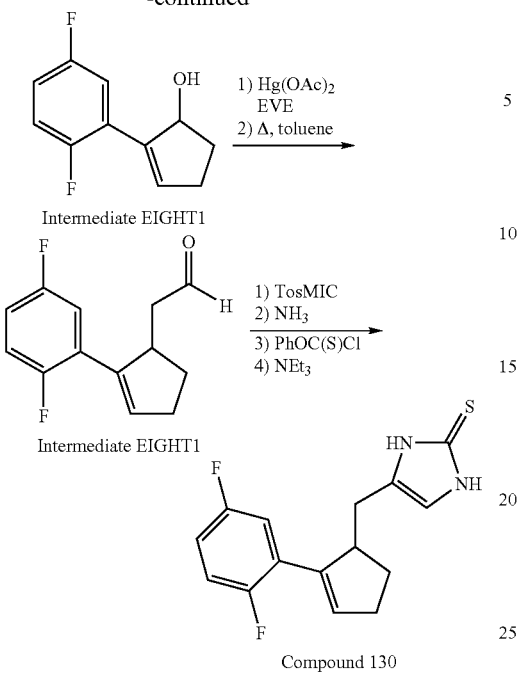

Use of 2,5-difluorophenylboronic acid (commercially available from Aldrich) in Method THREE produced 2-(2,5-difluoro-phenyl)-cyclopent-2-enol (Intermediate EIGHT1). Use of procedures in Method ONE and Method A produced 4-[2-(2,5-difluorofluorophenyl)-cyclopent-2-enylmethyl]-1,3-dihydro-imidazole-2-thione (Compound 130).

$^1$H NMR (300 MHz, MeOD-d$^4$) δ 7.17-7.10 (m, 1H), 7.09-7.02 (m, 1H), 6.98-6.91 (m, 1H), 6.44 (s, 1H), 6.26 (s, 1H), 3.47 (brs, 1H), 2.66-2.60 (m, 1H), 2.51-2.42 (m, 2H), 2.34-2.26 (m, 1H), 2.18-2.05 (m, 1H), 1.78-1.69 (m, 1H).

Example Eight-1

Compound 131

Use of thiophene-2-boronic acid (commercially available from Aldrich) in Method EIGHT produced 4-[2-thiophen-2-yl-cyclopent-2-enylmethyl]-1,3-dihydro-imidazole-2-thione (Compound 131).

$^1$H NMR (300 MHz, MeOD-d$^4$) δ 7.22 (d, J=5.1 Hz, 1H), 7.05 (d, J=3.6 Hz, 1H), 6.99-6.96 (m, 1H), 6.49 (s, 1H), 5.98 (s, 1H), 3.30 (brs, 1H), 2.85-2.80 (m, 1H), 2.44-2.37 (m, 3H), 2.14-2.01 (m, 1H), 1.85-1.77 (m, 1H).

Example Nine

Method NINE: Procedure for the preparation of produced 4-[3-ethyl-2-(4-fluoro-phenyl)-3-methyl-cyclopent-2-enylmethyl]-1,3-dihydro-imidazole-2-thione (Compound 132)

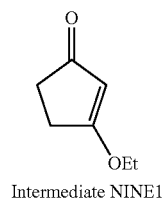

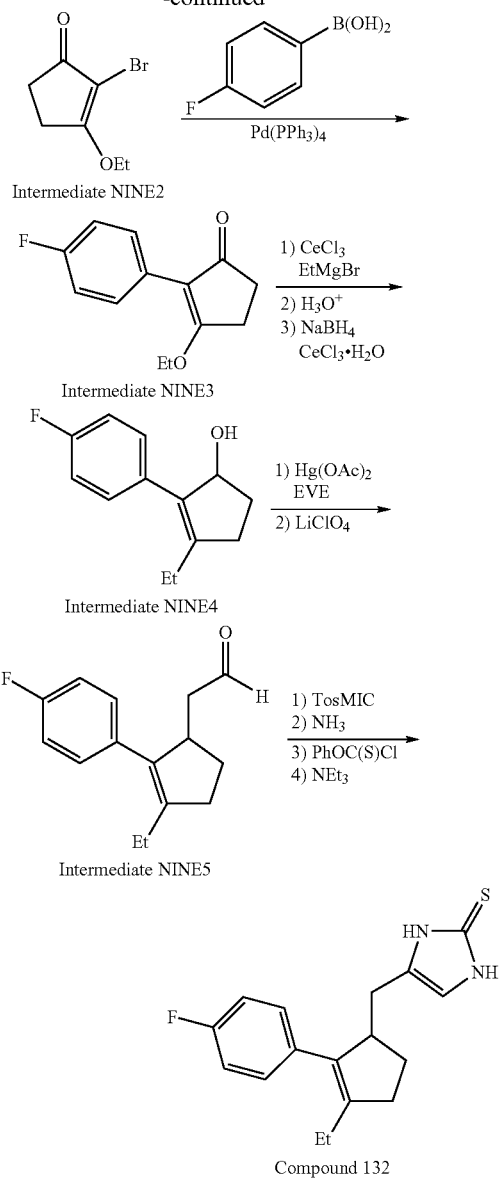

3-Ethoxy-cyclopent-2-enone (Intermediate NINE1) (commercially available from Aldrich) (10.0 g, 77.6 mmol) in carbon tetrachloride (15 mL) at 0° C. was treated with NBS (15.3 g, ~85 mmol) added portion-wise over 30 m. After 1 h at 0° C. the mixture was partitioned between CH$_2$Cl$_2$ and saturated NaHCO$_3$. The aqueous layer was extracted with CH$_2$Cl$_2$. The pooled organic layers were washed with H$_2$O (2×) and dried over MgSO$_4$. The mixture was filtered and evaporated to dryness. The solid was recrystallized from pentane:ether to give 13.3 g of 2-bromo-3-ethoxy-cyclopent-2-enone (Intermediate NINE2).

2-Bromo-3-ethoxy-cyclopent-2-enone (Intermediate NINE2) (10.5 g, 51.2 mmol) and K$_2$CO$_3$ (14.2 g, 102 mmol) in toluene (100 mL), benzene (100 mL) and H$_2$O (50 mL) was treated with a solution of 4-fluorophenylboronic acid (9.31 g, 66.5) in EtOH (100 mL). Tetrakis(triphenylphosphine) palladium(0) Pd(PPh$_3$)$_4$ (3 g, 2.6 mmol), bis(dibenzylideneacetone)palladium(0), Pd$_2$(dba)$_3$ (0.47 g, 0.5 mmol) and triphenylphosphine (0.27 g, 1.0 mmol) were added and the mixture was purged with N$_2$ for 15 m. The mixture was heated to 100° C. for 15 h. The mixture was diluted with water and EtOAc:hexane. After extracting with EtOAc:hexane, the combined organic layers were dried over MgSO$_4$, filtered and evaporated to dryness. The crude oil was purified by column chromatography on silica gel with 2.5% EtOAc:CH$_2$Cl$_2$ to give 3-ethoxy-2-(4-fluoro-phenyl)-cyclopent-2-enone (Intermediate NINE3) 7.85 g (70%).

Cerium chloride.7H$_2$O was dried under vacuum (~1 Torr) with gradual heating to 140° C. The cerium chloride.nH$_2$O (3.6 g, 13.6 mmol) was dried further under vacuum with heating to 170° C. over 3 h. The material was cooled to rt and suspended in THF (20 mL). Stirring was continued for 2 h. 3-Ethoxy-2-(4-fluoro-phenyl)-cyclopent-2-enone (Intermediate NINE3) (2.0 g, 9.1 mmol) in THF (~20 mL) was added to this mixture. The reaction mixture was cooled to 0° C. and ethyl magnesium bromide (commercially available from Aldrich) (13 mL, 39 mmol, 3M in ether) was added dropwise. The mixture was warmed to rt and allowed to stir for 15 h. The whole was cooled to 0° C. and quenched by the addition of 2% HCl (100 mL) and stirred for 15 m. The mixture was extracted with EtOAc and the combined organic layers were evaporated to give the crude oil that was used in the next step without further purification. The reduction with NaBH$_4$ was performed as in Method A to yield Intermediate NINE4.

Use of 3-ethyl-2-(4-fluoro-phenyl)-cyclopent-2-enol of (Intermediate NINE4) in Method A produced 4-[3-ethyl-2-(4-fluoro-phenyl)-3-methyl-cyclopent-2-enylmethyl]-1,3-dihydro-imidazole-2-thione (Compound 132).

$^1$H NMR (300 MHz, CDCl$_3$) δ 11.4 (s, 1H), 11.2 (s, 1H), 7.16-7.10 (m, 2H), 7.02-6.96 (m, 2H), 6.03 (s, 1H), 3.37 (brs, 1H), 2.61-2.01 (series of m, 7H), 1.58-1.49 (m, 1H), 0.97 (t, J=8.4 Hz, 3H).

Example Nine-1

Compound 133

Use of n-propyl magnesium chloride (commercially available from Aldrich) in Method NINE produced 4-[2-(4-fluoro-phenyl)-3-propyl-cyclopent-2-enylmethyl]-1,3-dihydro-imidazole-2-thione (Compound 133).

$^1$H NMR (300 MHz, CDCl$_3$) δ 11.5 (s, 1H), 11.3 (s, 1H), 7.12 (dd, J=5.7, 8.7 Hz, 2H), 6.99 (t, J=8.4 Hz, 2H), 6.30 (s, 1H), 3.37 (brs, 1H), 2.61-2.54 (m, 1H), 2.47-2.01 (m, 6H), 1.59-1.47 (m, 1H), 1.45-1.32 (m, 2H), 0.81 (t, J=7.5 Hz, 3H).

Example Nine-2

Compound 134

Use of isopropyl magnesium chloride (commercially available from Aldrich) in Method NINE produced 4-[2-(4-fluoro-phenyl)-3-isopropyl-cyclopent-2-enylmethyl]-1,3-dihydro-imidazole-2-thione (Compound 134).

$^1$H NMR (300 MHz, CDCl$_3$) δ 11.6 (s, 1H), 11.4 (s, 1H), 7.11 (dd, J=5.7, 8.7 Hz, 2H), 6.98 (t, J=8.7 Hz, 2H), 6.30 (s, 1H), 3.33 (brs, 1H), 2.71-2.50 (m, 2H), 2.38-2.30 (m, 2H), 2.20-1.99 (m, 2H), 1.55-1.44 (m, 1H), 1.05 (d, J=6.6 Hz, 3H), 0.85 (d, J=6.9 Hz, 3H).

Example Nine-3

Compound 135

Use of cyclopropyl magnesium bromide (made from cyclopropyl bromide (commercially available from Aldrich) and Mg(0)) in Method NINE produced 4-[3-cyclopropyl-2-(4-fluoro-phenyl)-cyclopent-2-enylmethyl]-1,3-dihydro-imidazole-2-thione (Compound 135).

$^1$H NMR (300 MHz, MeOD-d$^4$) δ 7.32 (dd, J=6.0, 9.0 Hz, 2H), 7.07 (t, J=8.7 Hz, 2H), 6.38 (s, 1H), 3.39 (brs, 1H), 2.58-2.52 (m, 1H), 2.23-2.01 (m, 4H), 1.68-1.49 (series of m, 2H), 0.73-0.66 (m, 1H), 0.60-0.51 (m, 3H).

Example Nine-4

Compound 136

Use of 3-ethoxy-cyclohex-2-enone as the starting material and methyl magnesium bromide (both commercially available from Aldrich) in Method NINE produced 4-[2-(4-fluoro-phenyl)-3-methyl-cyclohex-2-enylmethyl]-1,3-dihydro-imidazole-2-thione (Compound 136).

$^1$H NMR (300 MHz, CDCl$_3$) δ 7.10-6.90 (m, 4H), 6.30 (s, 1H), 2.66 (brs, 1H), 2.42-2.21 (m, 2H), 2.14-2.04 (m, 2H), 1.71-1.57 (m, 4H), 1.49 (s, 3H).

Example Ten

Method TEN: Procedure for the preparation of produced 4-[2-methyl-5-(2-thioxo-2,3-dihydro-1H-imidazol-4-yl-methyl)cyclopent-1-enyl]benzonitrile (Compound 137)

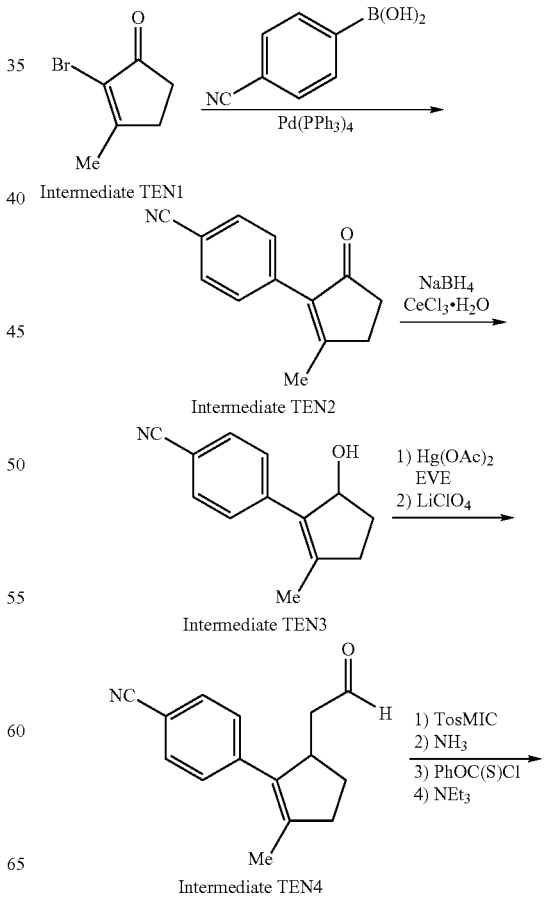

119

-continued

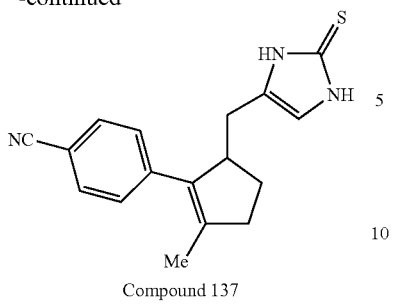

Compound 137

2-Bromo-3-methyl-cyclopent-2-enone (Intermediate TEN1) (commercially available from Aldrich) (2.04 g, 11.4 mmol) and $K_2CO_3$ (3.16 g in 11 mL $H_2O$) in toluene (45 mL) was treated with a solution 4-cyanophenylboronic acid (commercially available from Aldrich) (2.2 g, 15 mmol) in EtOH (27 mL). Tetrakis(triphenylphosphine) palladium(0) $Pd(PPh_3)_4$ (0.4 g), bis(dibenzylideneacetone) palladium(0), $Pd_2(dba)_3$ (0.055 g, ~5 mol %) and triphenylphosphine (0.4 g) were added and the mixture was purged with $N_2$ for 15 m. The mixture was heated to 80° C. for 15 h. The mixture was diluted with water and EtOAc:hexane. After extracting with EtOAc:hexane, the combined organic layers were dried over $MgSO_4$, filtered and evaporated to dryness. The crude oil was purified by column chromatography on silica gel with $CH_2Cl_2$ to give 4-(2-methyl-5-oxo-cyclopent-1-enyl)-benzonitrile (Intermediate TEN2) 1.74 g.

Use of 4-(2-methyl-5-oxo-cyclopent-1-enyl)-benzonitrile (Intermediate TEN2) in Method A produced 4-[2-methyl-5-(2-thioxo-2,3-dihydro-1H-imidazol-4-yl-methyl)cyclopent-1-enyl]benzonitrile (Compound 137).

$^1$H NMR (500 MHz, MeOD-$d^4$) δ 7.70 (d, J=8.5 Hz, 2H), 7.40 (d, J=8.5 Hz, 2H), 6.38 (s, 1H), 3.50 (brs, 1H), 2.61-2.52 (m, 2H), 2.45-2.13 (series of m, 3H), 1.78 (s, 3H), 1.68-1.61 (m, 1H).

Example TEN-1

Compound 138

Use of 4-nitrophenylboronic acid (commercially available from Aldrich) in Method TEN produced 4-[3-methyl-2-(nitro-phenyl)-cyclopent-2-enylmethyl]-1,3-dihydro-imidazole-2-thione (Compound 138).

$^1$H NMR (300 MHz, CDCl$_3$) δ 11.6 (s, 1H), 10.8 (s, 1H), 8.17 (d, J=8.7 Hz, 2H), 7.39 (d, J=9.0 Hz, 2H), 6.35 (s, 1H), 3.54 (brs, 1H), 2.64-2.09 (m, 5H), 1.78 (s, 3H), 1.64-1.53 (m, 1H).

Example Ten-2

139

Use of 3,5-difluorophenylboronic acid (commercially available from Aldrich) in Method TEN produced 4-[2-(3,5-difluorophenyl)-3-methyl-cyclopent-2-enylmethyl]-1,3-dihydro-imidazole-2-thione (Compound 139).

$^1$H NMR (300 MHz, CDCl$_3$) δ 11.0 (s, 1H), 10.6 (s, 1H), 6.77-6.63 (m, 3H), 6.32 (s, 1H), 3.40 (brs, 1H), 2.65-2.05 (series of m, 5H), 1.76 (s, 3H), 1.61-1.50 (s, 1H).

120

Example Twelve

Method TWELVE: Procedure for the preparation of 4-[2-(4-fluoro-phenyl)-3-methyl-cyclopent-2-enylmethyl]-1,3-dihydro-imidazole-2-thione (Compound 140)

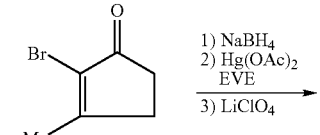

Intermediate TWELVE1

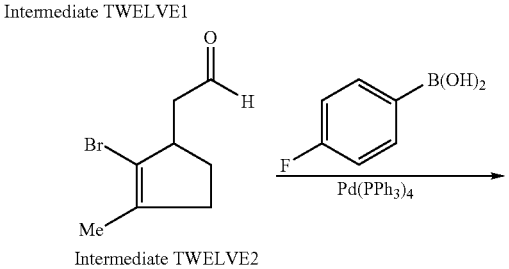

Intermediate TWELVE2

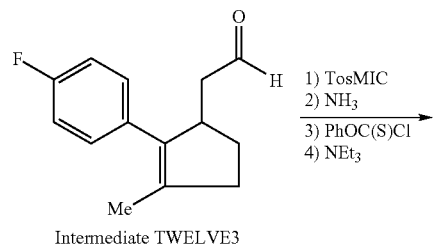

Intermediate TWELVE3

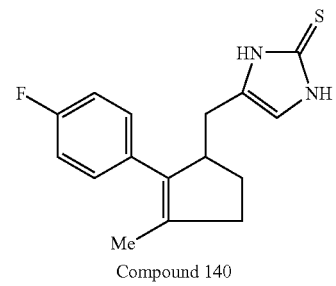

Compound 140

2-Bromo-3-methyl-cyclopent-2-enone (Intermediate TWELVE1) (commercially available from Aldrich) was homologated according to Method A to produce (2-bromo-3-methyl-cyclopent-2-enyl)-acetaldehyde (Intermediate TWELVE2).

(2-Bromo-3-methyl-cyclopent-2-enyl)-acetaldehyde (Intermediate TWELVE2) (7.28 mmol) in benzene (50 mL) was treated with $Na_2CO_3$ (7.3 mL, 2M soln.) and 4-fluorophenylboronic acid (1.4 g, 10.0 mmol) in EtOH (35 mL). Tetrakis (triphenylphosphine) palladium(0), $Pd(PPh_3)_4$ catalyst (0.54 g, ~5 mol %) was added and the mixture was heated to 80° C. for 15 h. until no starting material remained. The mixture was filtered through celite. The filtrate was partitioned between EtOAc and water. The aqueous layer was extracted with EtOAc and the organic layers were combined and dried over $MgSO_4$. Chromatography on silica gel with 20% EtOAc: hexane delivered [2-(4-fluoro-phenyl)-3-methyl-cyclopent-2-enyl]-acetaldehyde (Intermediate TWELVE3) 0.8 g.

[2-(4-fluoro-phenyl)-3-methyl-cyclopent-2-enyl]-acetaldehyde (Intermediate TWELVE3) in Method A produced 4-[2-(4-fluoro-phenyl)-3-methyl-cyclopent-2-enylmethyl]-1,3-dihydro-imidazole-2-thione (Compound 140).

$^1$H NMR (500 MHz, MeOD-d$^4$) δ 7.22 (dd, J=5.5, 9.0 Hz, 2H), 7.06 (t, J=9.0 Hz, 2H), 6.04 (s, 1H), 3.39 (brs, 1H), 2.56-2.46 (m, 2H), 2.38-2.32 (m, 1H), 2.22-2.17 (m, 1H), 2.13-2.06 (m, 1H), 1.75 (s, 3H), 1.62-1.56 (m, 1H).

Example Sixteen-Alpha

Compound 141

Procedure for the synthesis of 8-chloro-2-(2-thioxo-2,3-dihydro-1H-imidazol-4-ylmethyl)-3,4-dihydro-2H-naphthalen-1-one (Compound 141)

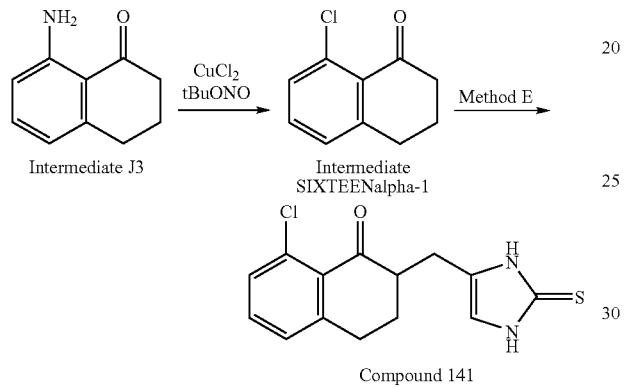

A mixture of CuCl$_2$ (2.0, 14.8 mmol) and t-butyl nitrite (2.3 mL, 17.4 mmol) in acetonitrile (30 mL) at 65° C. was treated with 8-amino-3,4-dihydro-2H-naphthalen-1-one (Intermediate J3) in acetonitrile (15 mL) over 10 m. The mixture was concentrated onto silica gel and purified by column chromatography with 10% EtOAc:hexane to give 8-chloro-3,4-dihydro-2H-naphthalen-1-one (Intermediate SIXTEENalpha-1). Use of 8-chloro-3,4-dihydro-2H-naphthalen-1-one (Intermediate SIXTEENalpha-1) in Method E (note: PtO$_2$ was used as a substitute for Pd/C as described in Method E) produced 8-chloro-2-(2-thioxo-2,3-dihydro-1H-imidazol-4-ylmethyl)-3,4-dihydro-2H-naphthalen-1-one (Compound 141).

$^1$H NMR (300 MHz, MeOH-d$^4$) δ 7.42-7.32 (m, 2H), 7.24 (d, J=6.3 Hx, 1H), 6.61 (s, 1H), 3.10-3.03 (m, 3H), 2.92-2.82 (m, 1H), 2.63 (dd, J=7.8, 7.2 Hz, 1H), 2.20-2.12 (m, 1H), 1.85-1.71 (m, 1H).

Example Sixteenbeta

Procedure for the synthesis of 7-iodo-indan-1-one (Intermediate SIXTEENbeta3)

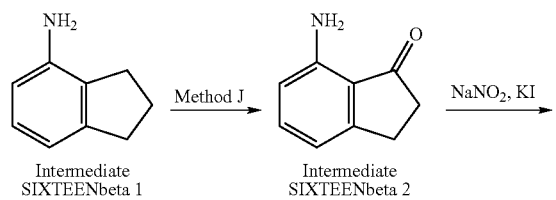

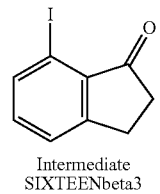

Use of indan-4-ylamine (Intermediate SIXTEEN-beta-1) (commercially available from Aldrich) in Method J produced 7-amino-indan-1-one (Intermediate SIXTEENbeta-2). A mixture of 7-amino-indan-1-one (Intermediate SIXTEEN-beta-2) (1.44 g, 9.8 mmol) in water (11 mL), acetic acid (11 mL), and HCl (2.7 mL) was treated with a solution of NaNO$_2$ (0.75 g in 2.8 mL) at 0° C. A solution of KI in water (1.76 g 10.4 mmol in 2.8 mL) was added and the mixture was heated to 60° C. for 1 h. The mixture was cooled and quenched with solid NaHSO$_3$ followed by water. The product was extracted with CH$_2$Cl$_2$ (3×) and washed with sat. NaHCO$_3$ and brine. The compound was purified by column chromatography on silica gel with 60 to 70% CH$_2$Cl$_2$:hexane. 7-Iodo-indan-1-one (Intermediate SIXTEENbeta3) was isolated as a light yellow solid (31%).

Example Seventeen

Compound 142

Procedure for the synthesis produced 4-indan-2-ylmethyl-1,3-dihydro-imidazole-2-thione (Compound 142)

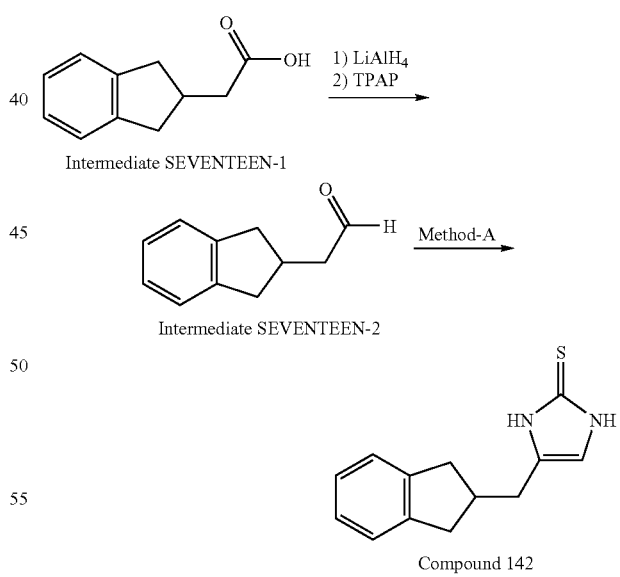

Use of indan-2-yl-acetic acid (commercially available from Lancaster) (Intermediate SEVENTEEN-1) (1.58 g, 8.88 mmol) in THF (15 mL) was added dropwise to a solution of LiAlH$_4$ (9 mL, IM in Et$_2$O) in THF (10 mL) at 0° C. The mixture was reacted for 2 h at rt and quenched with Rochelle's salt solution and extracted with Et$_2$O (3×). The organic layer was dried over MgSO$_4$, filtered and concentrated under vacuum. The alcohol (1.35 g, 94%) was used in the next step without further purification. A solution of 2-indan-2-yl-ethanol (1.35 g, 8.32 mmol) in 18 mL of $CH_2Cl_2$ and $CH_3CN$ (2 mL) was treated with 4 Å molecular sieves (4.2 g) N-methylmorpholine-N-oxide (1.5 g, 13.5 mmol) and TPAP: tetra-n-propylammonium perruthenate(VII) (commercially available from Aldrich) (0.3 g, 0.85 mmol). The mixture was stirred for 16 h at rt. The mixture was poured directly onto a column of silica gel and eluted with 10% EtOAc:hexane. To give indan-2-yl-acetaldehyde (Intermediate SEVENTEEN-2), 1.25 g (~90%). Indan-2-yl-acetaldehyde (Intermediate SEVENTEEN-2) in Method A produced 4-indan-2-ylmethyl-1,3-dihydro-imidazole-2-thione (Compound 142).

$^1$H NMR (300 MHz, MeOH-d$^4$) δ 7.16-7.12 (m, 2H), 7.10-7.06 (m, 2H), 6.59 (s, 1H), 3.02 (dd, J=7.8, 7.2 Hz, 1H), 2.76-2.57 (m, 5H).

Example Seventeen-1

Compound 143

Use of indan-2-carboxylic acid (commercially available from TCI America) in Method SEVENTEEN produced 4-indan-2-yl-1,3-dihydro-imidazole-2-thione (Compound 144).

$^1$H NMR (300 MHz, MeOH-d$^4$) δ 7.21 (m, 2H), 7.14-7.11 (m, 2H), 6.58 (s, 1H), 3.55-3.44 (m, 1H), 3.29-3.20 (m, 2H), 3.03-2.92 (m, 2H)

Example Seventeen-2

Compound 144

Use of 1,2,3,4-tetrahydro-naphthalene-2-carboxylic acid (commercially available from Aldrich) in Method SEVENTEEN produced 4-(1,2,3,4-tetrahydro-naphthalen-2-yl)-1,3-dihydro-imidazole-2-thione (Compound 144).

$^1$H NMR (300 MHz, MeOH-d$^4$) δ 7.06 (brs, 4H), 6.54 (s, 1H), 3.09-3.03 (m, 1H), 2.96-2.78 (m, 4H), 2.19-2.13 (m, 1H), 1.86-1.73 (m, 1H).

Example Eighteen

Compound 145

Procedure for the preparation of 4-(5-fluoro-indan-2-yl)-1,3-dihydro-imidazole-2-thione (Compound 145)

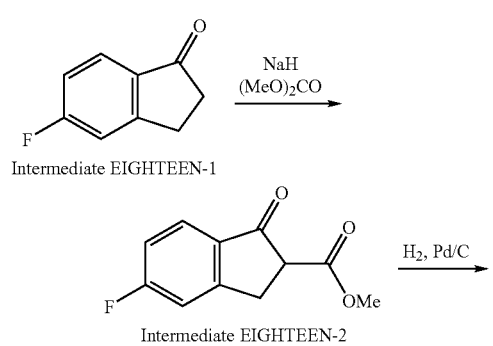

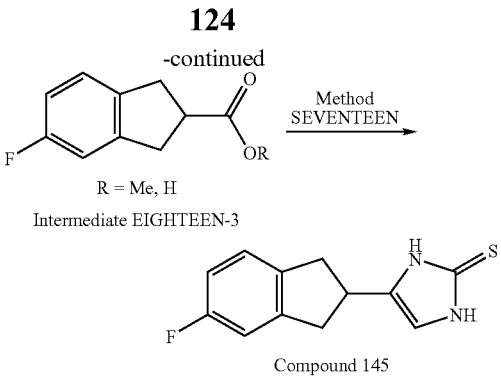

To a mixture of NaH (2.64 g, 66 mmol) in dimethylcarbonate (4.2 mL, 50 mmol) in THF (30 mL) was added a solution of 5-fluoroindanone (commercially available from Aldrich) (5 g, 33 mmol). After 30 m at 65° C. the mixture was cooled to rt, acidified with HCl (aq) and extracted with $Et_2O$ or EtOAc. The organic layers were washed with water, dried over $MgSO_4$ and evaporated to dryness. The residue was used in the next step without further purification. The keto-ester was dissolved in AcOH (100 mL) and 70% perchloric acid (2 mL). 10% Pd/C (2 g) was added and the mixture was hydrogenated at 50 psi for 18 h. The mixture was diluted with $Et_2O$ or $CHCl_3$ and water and filtered through a pad of celite. The organic layer was separated and the aqueous layer was extracted with $Et_2O$. The organic fractions were pooled, washed with water, dried over $MgSO_4$, filtered and evaporated to leave a residue. The residue was purified by chromatography on silica gel with 15% EtOAc:hexane to give 5-fluoro-indan-2-carboxylic acid methyl ester (Intermediate EIGHTEEN-3), 2.25 g. Use of 5-fluoro-indan-2-carboxylic acid methyl ester (Intermediate EIGHTEEN-3) in Method SEVENTEEN produced 4-(5-fluoro-indan-2-yl)-1,3-dihydro-imidazole-2-thione (Compound 145).

$^1$H NMR (300 MHz, DMSO-d$^6$) δ 12.0 (s, 1H), 11.7 (s, 1H), 7.20 (dd, J=5.7, 8.4 Hz, 1H), 7.04 (d, J=9.3 Hz, 1H), 6.92 (t, J=8.8 Hz, 1H), 6.59 (s, 1H), 3.42 (t, J=8.7 Hz, 1H), 3.18-3.07 (m, 2H), 2.94-2.81 (m, 2H).

Example Eighteen-1

Compound 146

Use of 7-methyl-indan-1-one (commercially available from Aldrich) in Method EIGHTEEN produced 4-(4-methyl-indan-2-yl)-1,3-dihydro-imidazole-2-thione (Compound 146).

$^1$H NMR (300 MHz, DMSO-d$^6$) δ 12.0 (s, 1H), 11.6 (s, 1H), 7.02-7.00 (m, 2H), 6.94-6.92 (m, 1H), 6.60 (s, 1H), 3.43-3.32 (m, 1H), 3.18-3.07 (m, 2H), 2.93-2.76 (m, 2H), 2.19 (s, 3H).

Example Eighteen-2

Compound 147

Use of 6-methyl-indan-1-one (commercially available from Aldrich) in Method EIGHTEEN produced 4-(5-methyl-indan-2-yl)-1,3-dihydro-imidazole-2-thione (Compound 147).

$^1$H NMR (300 MHz, DMSO-d$^6$) δ 12.0 (s, 1H), 11.6 (s, 1H), 7.07 (d, J=7.2 Hz, 1H), 7.01 (s, 1H), 6.92 (d, J=7.5 Hz,

1H), 6.58 (s, 1H), 3.38-3.29 (m, 1H), 3.12-3.04 (m, 2H), 2.89-2.80 (m, 2H), 2.24 (s, 3H).

Example Nineteen

Compound 148

Procedure for the preparation of 4-(5-bromo-indan-2-yl)-1,3-dihydro-imidazole-2-thione (Compound 148)

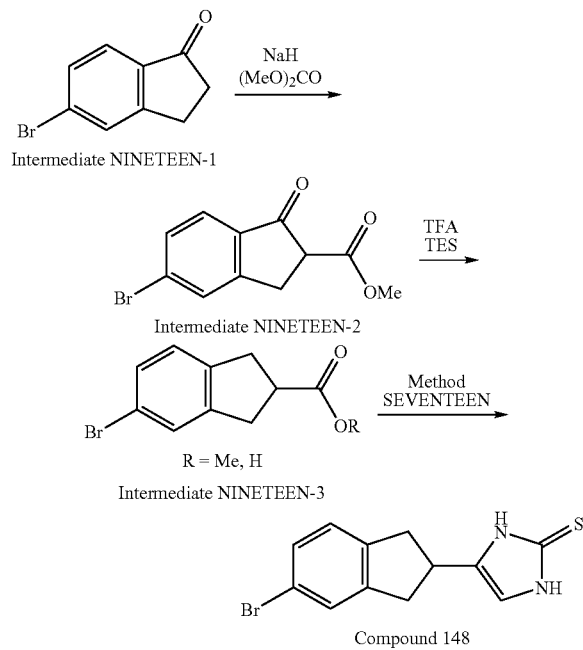

Use of 5-bromo-indan-1-one (Intermediate NINETEEN-1) in a reaction with NaH and dimethylcarbonate (refer to procedures in Method EIGHTEEN) produced 5-bromo-1-oxo-indan-2-carboxylic acid methyl ester (Intermediate NINETEEN-2). A solution of 5-bromo-1-oxo-indan-2-carboxylic acid methyl ester (4.75 g, 17.7 mmol) in TFA (80 mL) at 0° C. was treated with triethylsilane (TES) (17.0 mL, 6.0 eq) and stirred for 18 h. After evaporation of the solvent, the residue was diluted with Et$_2$O and washed with H$_2$O (5×100 mL), sat. NaHCO$_3$ (3×50 mL), brine (1×75 mL) and dried over MgSO$_4$ to give crude 5-bromo-indan-2-carboxylic acid methyl ester (Intermediate NINETEEN-3). A solution of 5-bromo-indan-2-carboxylic acid methyl ester (Intermediate NINETEEN-3) in AcOH containing 20% HCl was stirred overnight. After evaporation of the solvent, the residue was dissolved in 1N NaOH. The resulting mixture was washed with Et$_2$O (3×75 mL) after which it was acidified with HCl (aq). The solution was extracted with CH$_2$Cl$_2$ (3×150 mL) and the combined organic extracts was washed with H$_2$O (3×100 mL), brine (1×75 mL), dried over MgSO$_4$ and concentrated to give crude 5-bromo-indan-2-carboxylic acid. Use of 5-bromo-indan-2-carboxylic acid in Method EIGHTEEN produced 4-(5-bromo-indan-2-yl)-1,3-dihydro-imidazole-2-thione (Compound 148).

$^1$H NMR (300 MHz, DMSO-d$^6$) δ 12.0 (s, 1H), 11.7 (s, 1H), 7.41 (s, 1H), 7.30 (d, J=8.1 Hz, 1H), 7.16 (d, J=7.8 Hz, 1H), 6.60 (s, 1H), 3.46-3.35 (m, 1H), 3.19-3.06 (m, 2H), 2.95-2.81 (m, 2H).

Example Nineteen-1

Compound 149

4-Bromo-indan-1-one was obtained by the following procedure: A solution of 3-(2-bromo-phenyl)-propionic acid (commercially available from Oakwood Products) (15.0 g, 65.5 mmol) in CH$_2$Cl$_2$ at 0° C. was reacted with oxalyl chloride (7.2 mL, 1.5 eq) followed by 2-3 drops of DMF. The mixture was stirred until no more gas evolution was observed. As the mixture was concentrated and the residue was dissolved in CH$_2$Cl$_2$, cooled to 0° C., and treated with AlCl$_3$ (9.6 g, 1.1 eq). After 1 h the mixture was quenched with water and the layers were separated. The aqueous layer was extracted with Et$_2$O (3×150 mL) and the combined organic extracts were washed with H$_2$O (3×100 mL), saturated NaHCO$_3$ (3×100 mL), brine (1×100 mL), dried over MgSO$_4$ and concentrated. 4-Bromoindan-1-one, 10.5 g (76%) was obtained by chromatography using 10% EtOAc:hexane as eluant. Use of 4-bromo-indan-1-one in Method NINETEEN produced 4-(4-bromo-indan-2-yl)-1,3-dihydro-imidazole-2-thione (Compound 149).

$^1$H NMR (300 MHz, DMSO-d$^6$) δ 12.0 (s, 1H), 11.7 (s, 1H), 7.34 (d, J=7.8 Hz, 1H), 7.22 (d, J=7.5 Hz, 1H), 7.09 (t, J=7.5 Hz, 1H), 6.63 (s, 1H), 3.50-3.40 (m, 1H), 3.30-3.12 (m, 2H), 3.06-2.85 (m, 2H).

Example Nineteen-2

Compound 150

Use of 2,5-dimethylcinnamic acid in Method TWENTY (refer to Example TWENTY-4) produced 4,7-dimethyl-1-indanone. Use of 4,7-dimethyl-1-indanone in Method NINETEEN produced 4-(4,7-dimethyl-indan-2-yl)-1,3-dihydro-imidazole-2-thione (Compound 150)

$^1$H NMR (300 MHz, MeOH-d$^4$) δ 6.85 (s, 2H), 6.59 (s, 1H), 3.55-3.45 (m, 1H), 3.30-3.19 (m, 2H), 2.90-2.80 (m, 2H), 2.19 (s, 6H).

Example Nineteen-3

Compound 151

Use of 5-chloro-indan-1-one (commercially available from Aldrich) in Method NINETEEN produced 4-(5-chloro-indan-2-yl)-1,3-dihydro-imidazole-2-thione (Compound 151).

$^1$H NMR (300 MHz, MeOH-d$^4$) δ 7.22-7.12 (m, 3H), 6.59 (s, 1H), 3.60-3.49 (m, 1H), 3.27-3.19 (m, 2H), 3.02-2.91 (m, 2H).

Example Nineteen-4

Compound 152

Thionyl chloride (10.0 mL, 1.5 eq) and 3-chloro-2-methylbenzoic acid commercially available from Aldrich) (15.6 g, 91.4 mmol) in benzene was refluxed until no more gas evolution was observed. After cooling to rt the mixture was concentrated. The concentrate was diluted with dichloroethane and added to a solution of AlCl$_3$ (12.2 g, 1.0 eq) in dichloroethane at 10-20° C. Ethylene was bubbled through the mixture for 4 h. and the mixture was stirred overnight. The mixture was quenched with 4 N HCl. The resulting layers were separated and the aqueous layer was extracted with Et$_2$O (3×250 mL). The combined organic extract was washed with H₂O (3×150 mL), saturated NaHCO₃ (3×150 mL), brine (1×150 mL), dried over MgSO₄ and concentrated. Concentrated sulfuric acid was added and the mixture was stirred at 85° C. for 1 h. After cooling to rt, the reaction mixture was quenched with ice-water. The mixture was extracted with Et₂O (3×250 mL) and the combined organic extracts were washed with H₂O (3×200 mL), saturated NaHCO₃ (3×200 mL), brine (1×100 mL), dried over MgSO₄ and concentrated. Pure 6-chloro-7-methyl-1-indanone (11.9 g, 72%) was obtained after column chromatography using 20% EtOAc: hexane as eluant. Use of 6-chloro-7-methyl-1-indanone in Method NINETEEN produced 4-(5-chloro-4-methyl-indan-2-yl)-1,3-dihydro-imidazole-2-thione (Compound 152).

¹H NMR (300 MHz, MeOH-d⁴) δ 7.16 (d, J=8.5 Hz, 1H), 7.02 (d, J=8.5 Hz, 1H), 6.62 (s, 1H), 3.59-3.52 (m, 1H), 3.31-3.24 (m, 2H), 3.00-2.92 (m, 2H), 2.30 (s, 3H).

Example Nineteen-5

Compound 153

Thionyl chloride (5.73 mL, ~79 mmol) and 2,3-dichlorobenzoic acid (commercially available from Aldrich) (10.0 g, 52.4 mmol) in benzene was heated to reflux until no more gas evolution was observed. After cooling to rt the mixture was concentrated. The concentrate was diluted with dichloroethane and added to AlCl₃ (7.0 g, ~53 mmol) in dichloroethane at 10-20° C. Ethylene was bubbled through the mixture for 4 h. The mixture was stirred overnight and quenched with 4 N HCl. The resulting layers were separated and the aqueous layer was extracted with Et₂O (3×250 mL). The combined organic extracts were washed with H₂O (3×150 mL), saturated NaHCO₃ (3×150 mL), brine (1×150 mL), dried over MgSO₄ and concentrated. The concentrate was added to a slurry of AlCl₃ (9.0 g) and NaCl (2.4 g) at 130° C. The resulting mixture was stirred at 180° C. for 2 hours after which it was cooled to room temperature and quenched with ice followed by concentrated HCl. The mixture was extracted with CH₂Cl₂ (3×500 mL) and the combined organic extracts were concentrated and purified by column chromatography using 20% EtOAc:hexane eluant to give 6.8 g (80%) of 6,7-dichloro-1-indanone. Use of 6,7-dichloro-indan-1-one in Method NINETEEN produced 4-(4,5-dichloro-indan-2-yl)-1,3-dihydro-imidazole-2-thione (Compound 153).

¹H NMR (300 MHz, MeOH-d⁴) δ 7.31 (d, J=7.8 Hz, 1H), 7.14 (d, J=8.1 Hz, 1H), 6.62 (s, 1H), 3.67-3.56 (m, 1H), 3.42-3.31 (m, 2H), 3.09-2.99 (m, 2H).

Example Nineteen-6

Compound 154

Use of 3-methyl-indan-1-one (commercially available from Aldrich) in Method NINETEEN produced 4-(1-methyl-indan-2-yl)-1,3-dihydro-imidazole-2-thione (Compound 154).

¹H NMR (300 MHz, DMSO-d⁶) δ 12.0 (s, 1H), 11.7 (s, 1H), 7.20-7.10 (m, 4H), 6.69 (s, 1H), 3.17-3.04 (m, 2H), 2.96-2.78 (m, 2H), 1.22 (d, J=6.6 Hz, 3H).

Example Nineteen-7

Compound 155

Use of 7-iodo-indan-1-one (Intermediate SIXTEENbeta3) in Method NINETEEN produced 4-(4-iodo-indan-2-yl)-1,3-dihydro-imidazole-2-thione (Compound 155).

¹H NMR (300 MHz, DMSO-d⁶) δ 12.0 (s, 1H), 11.7 (s, 1H), 7.55 (d, J=8.1 Hz, 1H), 7.24 (d, J=7.5 Hz, 1H), 6.93 (t, J=7.8 Hz, 1H), 6.63 (s, 1H), 3.48-3.39 (m, 2H), 3.18-3.03 (m, 2H), 2.92-2.83 (m, 1H).

Example Twenty

Compound 156

Procedure for the preparation 4-(4,5-difluoro-indan-1-ylmethyl)-1,3-dihydro-imidazole-2-thione (Compound 156)

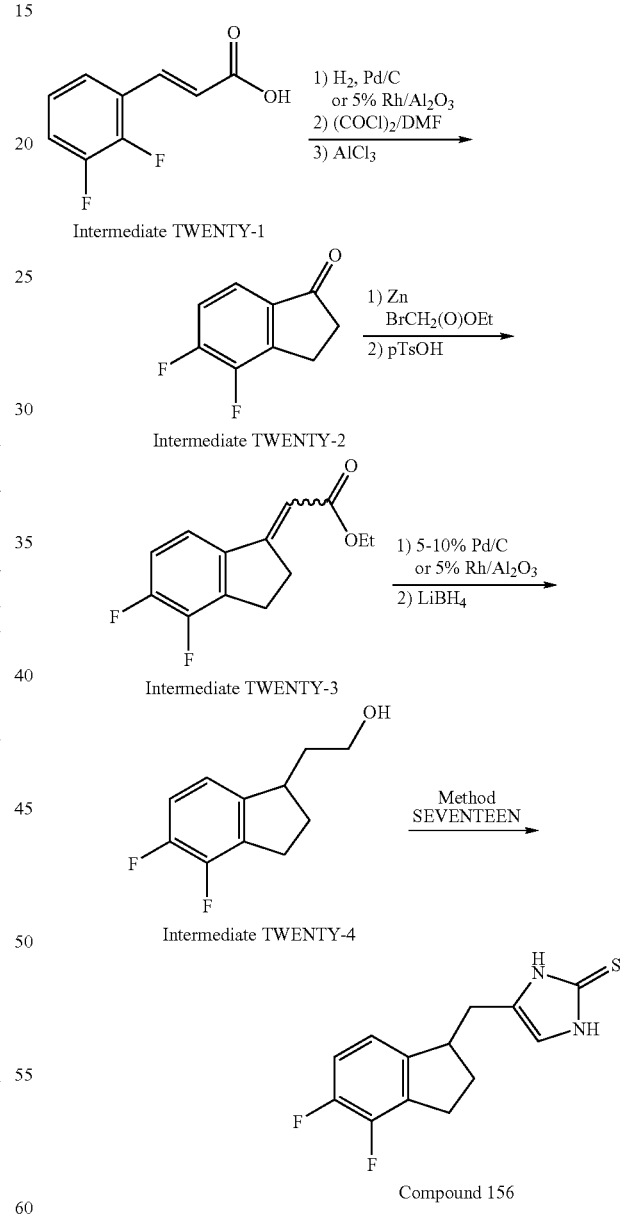

A solution of 2,3-difluorocinnamic acid (2.8 g, 15.2 mol) (commercially available from Lancaster) (Intermediate TWENTY-1) in ethanol (100 mL) was hydrogenated with H₂ (balloon) and 10% Pd/C (0.3 g) at rt for 16 h. The mixture was filtered through Celite® and the solvent was evaporated to give 3-(2,3-difluoro-phenyl)-propionic acid as a solid, 2.68 g (98%). A mixture of 3-(2,3-difluoro-phenyl)-propionic acid (2.7 g, 14.4 mmol) in CH$_2$Cl$_2$ at 0° C. was treated with oxalyl chloride (8.7 mL, 2 M in CH$_2$Cl$_2$) and a few drops of DMF. The reaction mixture was stirred for 2 h at rt. The solution was decanted from the dark colored residues and the solvent was removed under vacuum. The residue was dissolved in CH$_2$Cl$_2$ (20 mL) and added to a mixture of AlCl$_3$ (1.92 g, 14.4 mmol) in CH$_2$Cl$_2$ (25 mL). The mixture was heated at 50° C. for 16 h. The entire mixture was poured into ice water. The aqueous phase was removed and extracted with CH$_2$Cl$_2$. The organic layers were combined, washed with sat. NaHCO$_3$ solution, brine, and dried over Na$_2$SO$_4$, filtered, and evaporated to dryness. The residue was purified by chromatography on silica gel with 20% EtOAc:hexane to give 4,5-difluoro-indan-1-one (Intermediate TWENTY-2), 1.65 g (68%).

A solution of give 4,5-difluoro-indan-1-one (Intermediate TWENTY-2) (1.36 g, 8.10 mmol) in benzene (20 mL) and ether (20 mL) was treated with a few iodine crystals followed by ethyl bromoacetate (1.4 mL, 12.3 mmol) and zinc dust (1.60 g, 24.4 mmol). The mixture was heated to 70° C. for 16 h at rt. The mixture was cooled to rt and filtered through a pad of Celite. The filtrate was evaporated and the residue ((4,5-difluoro-1-hydroxy-indan-1-yl)-acetic acid ethyl ester) was dissolved in benzene and treated with a catalytic amount of pTsOH. The mixture was heated at reflux in a Dean-Stark trap for 16 h. The mixture was cooled to rt and diluted with aqueous acid and ethyl acetate. The aqueous layer was extracted with ethyl acetate. The organic layers were pooled and dried over MgSO$_4$. The solution was filtered, evaporated and purified by chromatography on silica gel with 10 to 15% ether:hexane to give a mixture of E- and Z-(4,5-difluoro-indan-1-ylidene)-acetic acid ethyl ester (Intermediate TWENTY-3) as a solid, 1.1 g.

A mixture of E- and Z-(4,5-difluoro-indan-1-ylidene)-acetic acid ethyl ester (Intermediate TWENTY-3) (1.1 g) in EtOAc (25 mL) was hydrogenated with 10% Pd/C (0.16 g) under H$_2$ (balloon) at rt for 16 h. The mixture was filtered through a bed of Celite® and the filtrate was evaporated under vacuum. The ester, (4,5-difluoro-indan-1-yl)-acetic acid ethyl ester (1.1 g, 4.58 mmol) in THF (60 mL) and MeOH (1 mL) was treated with LiBH$_4$ (0.21 g, 8.5 mmol) at 65° C. for 5 h. The mixture was cooled and THF was removed under vacuum. The solution was diluted with EtOAc and sat. NH$_4$Cl. The layers were separated and the organic layer was dried over MgSO$_4$ and filtered. After evaporation, the alcohol, 2-(4,5-difluoro-indan-1-yl)-ethanol (Intermediate TWENTY-4) was isolated as a clear, colorless oil, 1.7 g, (88%). Use, 2-(4,5-difluoro-indan-1-yl)-ethanol (Intermediate TWENTY-4) in Method SEVENTEEN produced 4-(4,5-difluoro-indan-1-ylmethyl)-1,3-dihydro-imidazole-2-thione (Compound 156).

$^1$H NMR (300 MHz, MeOH-d$^4$) δ 7.05-6.96 (m, 1H), 6.89-6.85 (m, 1H), 6.52 (s, 1H), 3.46-3.38 (m, 1H), 3.00-2.83 (m, 3H), 2.61-2.54 (dd, J=9.0, 6.0 Hz, 1H), 2.36-2.24 (m, 1H), 1.90-1.79 (m, 1H).

Example Twenty-1

Compound 157

Use of 6-fluoro-indan-1-one (commercially available from Lancaster) in Method TWENTY produced 4-(6-fluoro-indan-1-ylmethyl)-1,3-dihydro-imidazole-2-thione (Compound 157).

$^1$H NMR (300 MHz, MeOH-d$^4$) δ 7.18-7.13 (m, 1H), 6.87-6.82 (m, 2H), 6.52 (m, 1H), 3.45-3.34 (m, 1H), 2.92-2.74 (m, 3H), 2.60-2.52 (dd, J=9.0, 6.0 Hz, 1H), 2.31-2.19 (m, 1H), 1.84-1.73 (m, 1H).

Example Twenty-2

Compound 158

Use of 3-(3,4-difluoro-phenyl)-acrylic acid (commercially available from Aldrich) in Method TWENTY produced 4-(5,6-difluoro-indan-1-ylmethyl)-1,3-dihydro-imidazole-2-thione (Compound 158).

$^1$H NMR (300 MHz, MeOH-d$^4$) δ 7.10-7.00 (m, 2H), 6.53 (s, 1H), 3.41-3.36 9m, 1H), 2.90-2.79 (m, 3H), 2.60-2.52 (dd, J=9.6, 5.7 Hz, 1H), 2.32-2.20 (m, 1H), 1.86-1.74 (m, 1H).

Example Twenty-3

Compound 159

Use of 2-fluorocinnamic acid (commercially available from Aldrich) in Method TWENTY produced 4-(4-fluoro-indan-1-ylmethyl)-1,3-dihydro-imidazole-2-thione (Compound 159).

$^1$H NMR (300 MHz, MeOH-d$^4$) δ 7.18-7.11 (m, 1H), 6.94 (d, J=7.3 Hz, 1H), 6.85 (t, J=8.4 Hz, 1H), 6.50 (s, 1H), 3.50-3.42 (m, 1H), 2.93-2.80 (m, 3H), 2.62-2.54 (m, 1H), 2.30-2.24 (m, 1H), 1.86-1.80 (m, 1H).

Example Twenty-4

Compound 160

Use of 2,5-dimethylcinnamic acid (commercially available from Lancaster) in Method TWENTY produced 4,7-dimethylindan-1-one. Use of 4,7-dimethylindan-1-one in Method A produced 4-(4,7-dimethyl-indan-1-ylmethyl)-1,3-dihydro-imidazole-2-thione (Compound 160).

$^1$H NMR (300 MHz, DMSO-d$^6$) δ 12.0 (s, 1H), 11.6 (s, 1H), 6.86-6.80 (m, 2H), s, 1H), 3.43-3.36 (m, 1H), 2.83-2.47 (m, 3H), 2.23-2.18 (m, 3H), 2.12 (s, 3H), 1.95-1.76 (m, 2H).

Example Twenty-5

Compound 161

Use of 8-chloro-3,4-dihydro-2H-naphthalen-1-one (Intermediate SIXTEEN-1) in Method TWENTY (note.: for both of the hydrogenation procedures: substitute 5% Rh on Alumina at 50 psi H$_2$ for any Pd/C catalyst) produced 4-(8-chloro-1,2,3,4-tetrahydro-naphthalen-1-ylmethyl)-1,3-dihydro-imidazole-2-thione (Compound 161).

$^1$H NMR (300 MHz, DMSO-d$^6$) δ 12.0 (s, 1H), 11.7 (m, 1H), 7.22 (d, J=7.2 Hz, 1H), 7.12 (t, J=7.5 Hz, 1H), 6.63 (s, 1H), 2.81-2.60 (m, 3H), 2.49-2.35 (m, 2H), 1.80-1.50 (m, 4H).

Example Tentytwo

Compound 162

Procedure for the synthesis of 4-(5,6,7,8-tetrahydro-quinolin-6-ylmethyl)-1,3-dihydro-imidazole-2-thione (Compound 162)

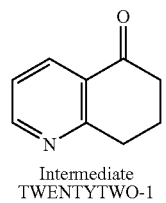

Intermediate
TWENTYTWO-1

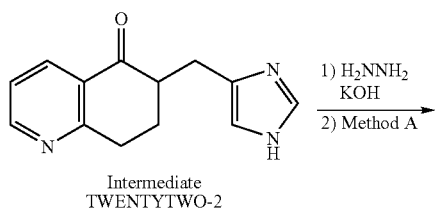

Intermediate
TWENTYTWO-2

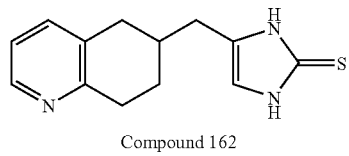

Compound 162

Use of 7,8-dihydro-6H-quinolin-5-one (Intermediate TWENTYTWO-1) (obtained as described in Molina, et. al. Tetrahedron 1995, 51, 1265, incorporated herein by reference) in Method E produced 6-(1H-imidazol-4-ylmethyl)-7,8-dihydro-6H-quinolin-5-one (Intermediate TWENTYTWO-2). To a solution of 6-(1H-imidazol-4-ylmethyl)-7,8-dihydro-6H-quinolin-5-one (Intermediate TWENTYTWO-2) (1.31 g, 227 mmol) in diethylene glycol (10 mL) was added hydrazine (6.3 mL, 200 mmol) followed by KOH (4.85 g, 56.2 mmol). The mixture was heated to 170° C. for 5 h. The mixture was diluted with water (200 mL) and sat. NaHCO$_3$. The aqueous solution was extracted with CHCl$_3$ (3×50 mL). The combined organic portions were washed with water and brine. The organic layer was dried over MgSO$_4$, filtered and evaporated to give 6-(1H-imidazol-4-ylmethyl)-5,6,7,8-tetrahydro-quinoline as a foamy solid, 1.15 g (92%). By the applicable process steps described in Method A, the imidazole compound was used to produce 4-(5,6,7,8-tetrahydro-quinolin-6-ylmethyl)-1,3-dihydro-imidazole-2-thione (Compound 162).

$^1$H NMR (300 MHz, DMSO-d$^6$) δ 11.9 (s, 1H), 11.7 (s, 1H), 8.29 (d, J=3.3 Hz, 1H), 7.45 (d, J=7.2 Hz, 1H), 7.10 (dd, J=7.5, 4.5 Hz, 1H), 6.62 (s, 1H), 2.93-2.71 (m, 3H), 2.51-2.37 (m, 3H), 2.04-1.90 (m, 2H), 1.50-1.37 (m, 1H).

Example Twentythree

Compound 163

Procedure for the synthesis of 4-(4-chloro-indan-2-yl)-1,3-dihydro-imidazole-2-thione (Compound 163)

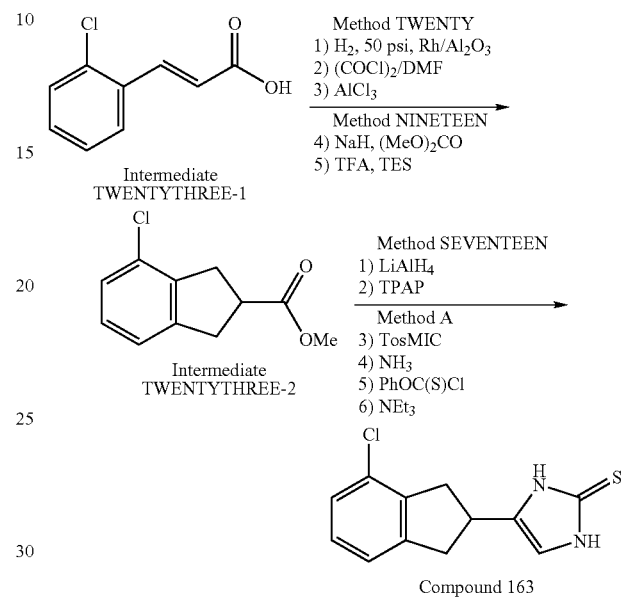

Use of 2-chlorocinnamic acid (Intermediate TWENTYTHREE-1) (commercially available from Aldrich) in the applicable process steps described in Method TWENTY and Method NINETEEN produced 4-chloro-indan-2-carboxylic acid methyl ester (Intermediate TWENTYTHREE-2). Use of 4-chloro-indan-2-carboxylic acid methyl ester (Intermediate TWENTYTHREE-2) in the applicable process steps described in Method SEVENTEEN and Method A produced 4-(4-chloro-indan-2-yl)-1,3-dihydro-imidazole-2-thione (Compound 163).

$^1$H NMR (300 MHz, MeOH-d$^4$) δ 7.13 (brs, 3H), 6.60 (s, 1H), 3.61-3.50 (m, 1H), 3.38-3.28 (m, 2H), 3.09-2.93 (m, 2H).

Example Twentythree-1

Compound 164

Use of 3,5-difluorocinnamic acid (commercially available from Aldrich) in Method TWENTY produced 5,7-difluoro indan-1-one. Use of 5,7-difluoro indan-1-one in Method TWENTYTHREE produced 4-(4,6-difluoro-indan-2-yl)-1,3-dihydro-imidazole-2-thione (Compound 164).

$^1$H NMR (300 MHz, DMSO-d$^6$) δ 12.1 (s, 1H), 11.7 (s, 1H), 7.01-6.96 (m, 2H), 6.66 (s, 1H), 3.57-3.46 (m, 1H), 3.26-3.16 (m, 2H), 3.01-2.83 (m, 2H).

Example Twentythree-2

Compound 165

Use of 3-fluoro-5-methoxycinnamic acid (commercially available from Aldrich) in the applicable process steps described in Method TWENTY and Method NINETEEN produced 4-fluoro-6-methoxy-indan-2-carboxylic acid methyl ester as an intermediate. This material was subjected to the applicable process steps described in Method SEVENTEEN and Method A in order to produce 4-(4-fluoro-6-methoxy-indan-2-yl)-1,3-dihydro-imidazole-2-thione (Compound 165).

$^1$H NMR (500 MHz, DMSO-d$^6$) δ 12.0 (s, 1H), 11.7 (s, 1H), 6.68-6.65 (m, 2H), 6.62 (s, 1H), 3.45-3.38 (m, 1H), 3.17-3.12 (m, 1H), 3.10-3.04 (m, 1H), 2.91-2.86 (m, 1H), 2.73-2.69 (m, 1H).

Example Twentyfour Compound 166

Procedure for the synthesis of 4-(4-chloro-indan-1-ylmethyl)-1,3-dihydro-imidazole-2-thione (Compound 166)

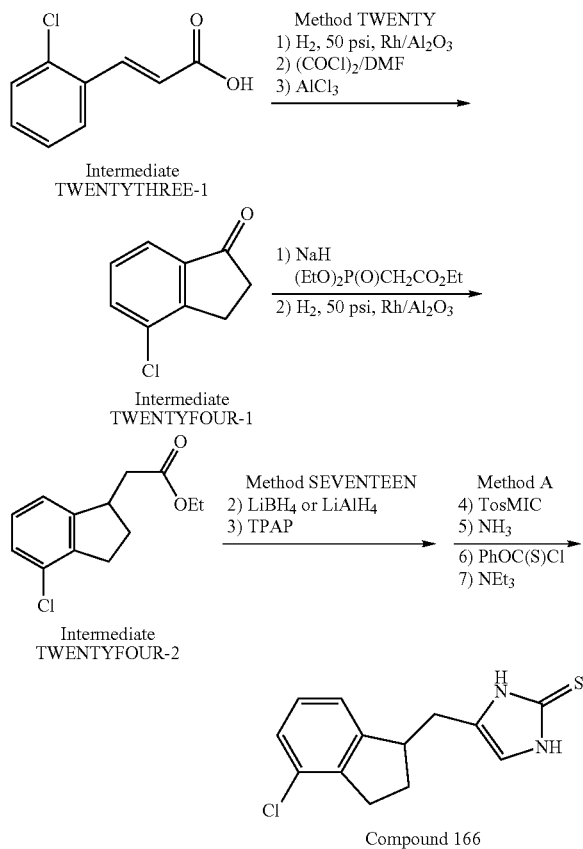

Use of 2-chlorocinnamic acid (Intermediate TWENTYTHREE-1) (commercially available from Aldrich) in the applicable process steps described in Method TWENTY produced 4-chloro-indan-1-one (Intermediate TWENTYFOUR-1). Triethylphosphonoacetate (3.5 mL, 17.2 mmol) was added to a mixture of NaH (0.69 g, 12.2 mmol) in THF (25 mL). After 30 m, a solution of 4-chloro-indan-1-one (Intermediate TWENTYFOUR-1) (1.46 g, 8.8 mmol) in THF (20 mL) was added to the mixture. The reaction mixture was allowed to stir for 16 h at rt. The solution was quenched with water and diluted with EtOAc. The layers were separated and the organic phase was dried over MgSO$_4$, filtered and evaporated under reduced pressure. The residue was subjected to chromatography on silica gel with 3% EtOAc:hexane. The fractions that contained the unsaturated esters were collected and evaporated to give the product, 1.67 g. The mixture of esters (1.67 g, 7.06 mmol) in EtOAc was hydrogenated in the presence of 5% Rh on Alumina (0.14 g) at 40-50 psi H$_2$ at rt for 2 d. The mixture was filtered through a plug of Celite® and concentrated in vacuo to produce (4-chloro-indan-1-yl)-acetic acid ethyl ester (Intermediate TWENTYFOUR-2). Use of (4-chloro-indan-1-yl)-acetic acid ethyl ester (Intermediate TWENTYFOUR-2) in the applicable process steps described in Method SEVENTEEN and Method A produced 4-(4-chloro-indan-1-ylmethyl)-1,3-dihydro-imidazole-2-thione (Compound 166).

$^1$H NMR (300 MHz, MeOH-d$^4$) δ 7.16-7.04 (m, 3H), 6.51 (s, 1H), 3.53-3.44 (m, 1H), 3.01-2.80 (m, 3H), 2.60 (dd, J=8.7, 6 Hz, 1H), 2.31-2.19 (m, 1H), 1.85-1.74 (m, 1H).

Example Twentyfour-1

Compound 167

Use of 4-bromoindanone (obtained by the procedures in Example NINETEEN-1 (Compound 149) in Method TWENTYFOUR produced 4-(4-bromo-indan-1-ylmethyl)-1,3-dihydro-imidazole-2-thione (Compound 167).

$^1$H NMR (300 MHz, MeOH-d$^4$) δ 7.31 (dd, J=7.5, 0.6 Hz, 1H), 7.11-7.02 (m, 2H), 6.51 (s, 1H), 3.56-3.47 (m, 1H), 2.99-2.78 (m, 3H), 2.63-2.55 (m, 1H), 2.30-2.19 (m, 1H), 1.84-1.73 (m, 1H).

Example Twentyfour-2

Compound 168

Use of 6,7-dihydro-5H-quinolin-8-one (obtained as described in Lemke, et. al. J. Med. Chem., 1977, 20, 1351, incorporated herein by reference) in the applicable process steps described in Method TWENTYFOUR produced E- and Z-(6,7-dihydro-5H-quinolin-8-ylidene)-acetic acid ethyl ester. Note: The reduction procedure for the mixture of esters was as follows. E- and Z-(6,7-dihydro-5H-quinolin-8-ylidene)-acetic acid ethyl ester (2.3 g, 10.6 mmol) was hydrogenated in a mixture of TFA (20 mL), and PtO$_2$ (150 mg) under 50 psi H$_2$ for 50 m at rt. The mixture was filtered through a bed of Celite® and using EtOAc. The filtrate was added to crushed ice and made basic (pH 8) with NaOH solution. The aqueous layer was extracted with EtOAc and the pooled organic layers were dried over MgSO$_4$, filtered, added to silica gel and evaporated to dryness. The material was eluted through a column of silica gel with 20% EtOAc: hexane to give (5,6,7,8-tetrahydro-quinolin-8-yl)-acetic acid ethyl ester 1.77 g (77%). Use of (5,6,7,8-tetrahydro-quinolin-8-yl)-acetic acid ethyl ester in the applicable process steps described in Method SEVENTEEN and Method A produced 4-(5,6,7,8-tetrahydro-quinolin-8-ylmethyl)-1,3-dihydro-imidazole-2-thione (Compound 168).

$^1$H NMR (300 MHz, MeOH-d$^4$) δ 8.36 (d, J=5.1 Hz, 1H), 7.53 (d, J=7.5 Hz, 1H), 7.18 (dd, J=4.5, 7.5 Hz, 1H), 6.54 (s, 1H), 3.10-3.00 (m, 2H), 2.78 (brs, 2H), 2.73-2.64 9m, 1H), 1.90-1.82 (m, 2H), 1.75-1.68 (m, 2H).

Example Twentyfive

Compound 169

Procedure for the synthesis of [2-(2-thioxo-2,3-dihydro-1H-imidazol-4-ylmethyl)-3,4-dihydro-2H-naphthalen-1-ylidene]-acetonitrile (Compound 169)

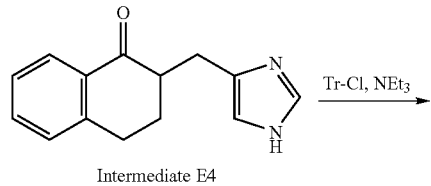

Intermediate E4

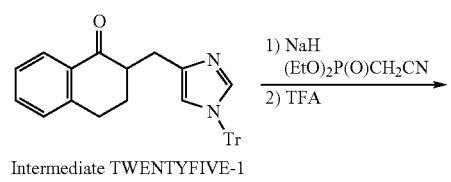

Intermediate TWENTYFIVE-1

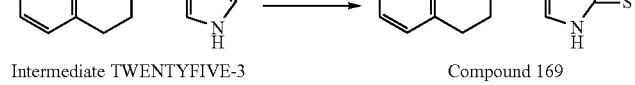

Intermediate TWENTYFIVE-2 → Compound 170

Intermediate TWENTYFIVE-3 → Compound 169

A solution of 2-(1H-imidazol-4-ylmethyl)-3,4-dihydro-2H-naphthalen-1-one (Intermediate E4) (2.11 g, 9.3 mmol) in DMF (25 mL) was treated with triethyl amine (1.9 mL, 13.6 mmol) and triphenylmethylchloride (tritylchloride) (2.74 g, 9.6 mmol, added dropwise in DMF (25 mL)). After 16 h at rt the mixture was partitioned between water and dichloromethane. The aqueous layer was extracted with dichloromethane and the organic layers were collected and dried over $MgSO_4$, filtered and concentrated onto silica gel. The material was placed on a column of silica gel and eluted with 50% EtOAc:hexane. The appropriate fractions were collected and 2-(1-trityl-1H-imidazol-4-ylmethyl)-3,4-dihydro-2H-naphthalen-1-one (Intermediate TWENTYFIVE-1) was isolated as a white solid, 3.58 g (82%). Sodium hydride (1.2 eqv) in DMF (25 mL) was reacted with diethyl(cyanomethyl) phosphonate (available from Aldrich) (1.3 eqv) (added dropwise). After 30 m at rt a solution of 2-(1-trityl-1H-imidazol-4-ylmethyl)-3,4-dihydro-2H-naphthalen-1-one (Intermediate TWENTYFIVE-1) in DMF (20 mL) was added in a dropwise fashion to the mixture. The mixture was stirred for 16 h at rt. Another aliquot (1.2 eqv) of prepared NaH and diethyl(cyanomethyl) phosphonate in DMF was added to the mixture and the solution was heated to 40° C. for 18 h. The mixture was quenched with sat. $NH_4Cl$, diluted with water, and extracted with EtOAc. The organic layers were dried over $MgSO_4$, filtered and concentrated onto silica gel. The material was eluted from a column of silica gel with 40% EtOAc:hexane. Two isomers E and Z (trans and cis) were collected from the column and carried onto the next step. A solution of the mixed trans and cis isomers of [2-(1-trityl-1H-imidazol-4-ylmethyl)-3,4-dihydro-2H-naphthalen-1-ylidene]-acetonitrile (0.33 g) was stirred in 95% TFA (trifluoroacetic acid, 9.5 mL) and water (0.5 mL) for 2 h at rt to remove the trityl protective group. The pH of the mixture was adjusted with 2M NaOH and extracted with EtOAc. The mixture was subjected to an aqueous work-up and concentrated onto silica gel. The material was eluted from a column of silica gel with 5% $NH_3$.MeOH in $CH_2Cl_2$ to give [2-(1H-imidazol-4-ylmethyl)-3,4-dihydro-2H-naphthalen-1-ylidene]-acetonitrile (trans isomer) (Intermediate TWENTYFIVE-2) as a clear colorless oil (~0.1 g). The cis isomer (Intermediate TWENTYFIVE-3) was isolated from the same process (0.27 g). Use of [2-(1H-imidazol-4-ylmethyl)-3,4-dihydro-2H-naphthalen-1-ylidene]-acetonitrile (Intermediate TWENTYFIVE-2) in the applicable process steps described in Method A produced [2-(2-thioxo-2,3-dihydro-1H-imidazol-4-ylmethyl)-3,4-dihydro-2H-naphthalen-1-ylidene]-acetonitrile (Compound 169 trans isomer)

$^1$H NMR (300 MHz, MeOH-d$^4$) δ 8.04 (d, J=8.0 Hz, 1H), 7.40 (t, J=7.5 Hz, 1H), 7.30-7.26 (m, 2H), 6.53 (s, 1H), 5.46 (s, 1H), 3.03-2.96 (m, 2H), 2.89-2.83 (m, 1H), 2.61 (d, J=7.0 Hz, 2H), 2.12-2.06 (m, 1H), 1.86-1.80 (m, 1H).

Example Twentyfive-1

Compound 170

Use of Intermediate TWENTYFIVE-3 (see above preparation) in the applicable process steps described in Method A produced [2-(2-thioxo-2,3-dihydro-1H-imidazol-4-ylmethyl)-3,4-dihydro-2H-naphthalen-1-ylidene]-acetonitrile (Compound 170 cis isomer).

$^1$H NMR (300 MHz, DMSO-d$^6$) δ 12.0 (s, 1H), 11.7 (s, 1H), 7.71 (d, J=8.1 Hz, 1H), 7.36 (t, J=7.5 Hz, 1H), 7.25-7.20 (m, 2H), 6.52 (s, 1H), 6.17 (s, 1H), 3.44-3.36 (m, 1H), 3.02-2.91 (m, 1H), 2.76-2.70 (m, 1H), 2.58-2.38 (m, 2H), 1.87-1.84 (m, 2H).

Example Twentysix

Compound 171

Procedure for the synthesis of 4-(5-methyl-3,6-dihydro-2H-pyran-2-ylmethyl)-1,3-dihydro-imidazole-2-thione (Compound 171)

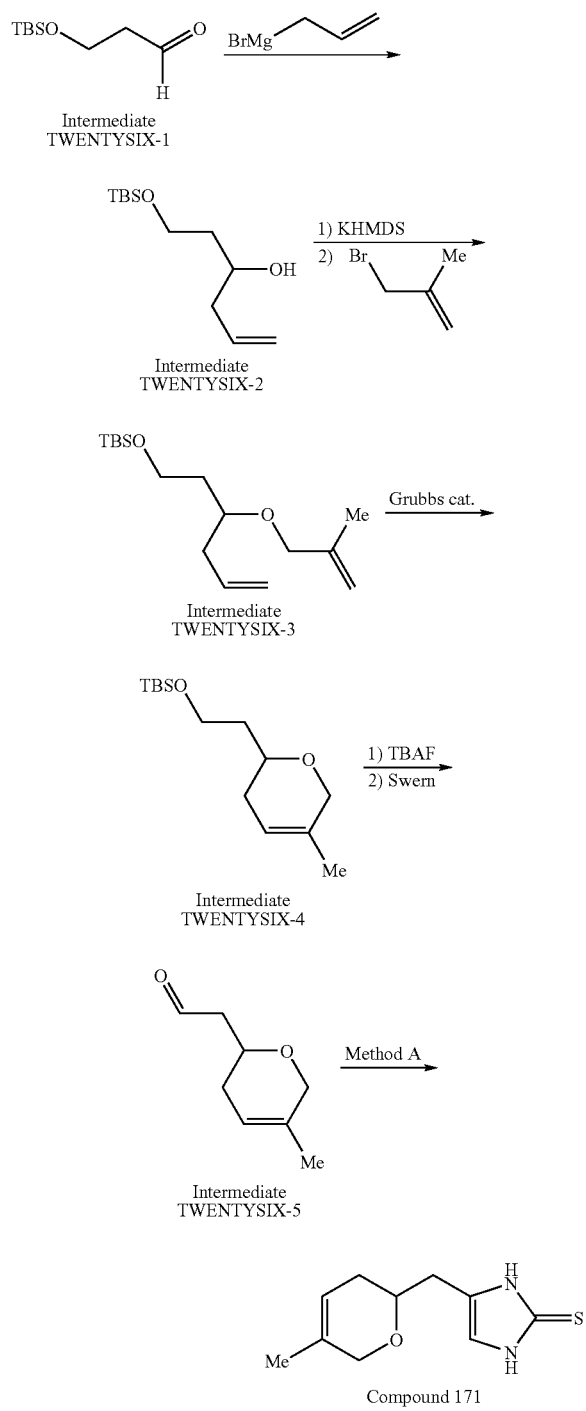

A solution of 3-(t-butyl-dimethyl-silanyloxy)-propionaldehyde (Intermediate TWENTYSIX-1) (1.5 g, 7.96 mmol) (obtained as described in Berque, et al J. Org. Chem. 1999, 373, incorporated herein by reference) in diethyl ether (60 ml), at −30° C., was treated with a solution of allylMgBr (9.6 mL, 1.0 M in ether). The mixture was allowed to warm to 0° C. and remained at this temperature for 1 h. The solution was diluted with water (30 mL) and the layers were separated. The aqueous layer was extracted with ether (2×15 mL). The organic phases were combined and dried over $MgSO_4$. The solution was filtered and evaporated under reduced pressure. The crude material was purified by chromatography on $SiO_2$ with 10% EtOAc:hexane to give 1-(t-butyl-dimethyl-silanyloxy)-hex-5-en-3-ol (Intermediate TWENTYSIX-2) 1.7 g (93%). 1-(t-Butyl-dimethyl-silanyloxy)-hex-5-en-3-ol (Intermediate TWENTYSIX-2) (0.94 g, 4.1 mmol) in THF (10 mL) was treated with KHMDS (14.8 mL, 0.5 M in toluene) at 0° C. to 20° C. for 1 h. 2-Bromo-2-methyl propene (1.1 g mL, 8.2 mmol) was added via syringe at 0° C. The mixture was allowed to warm to rt. Stirring was continued for 16 h. The mixture was quenched with water. The organic layer was dried over $MgSO_4$, filtered and evaporated in vacuo. The residue was purified by chromatography on $SiO_2$ with 5% ether:hexane to give t-butyl-dimethyl-[3-(2-methyl-allyloxy)-hex-5-enyloxy]-silane (Intermediate TWENTYSIX-3) 1.16 g, (86%). A solution of t-butyl-dimethyl-[3-(2-methyl-allyloxy)-hex-5-enyloxy]-silane (Intermediate TWENTYSIX-3) (1.0 g, 3.73 mmol) in $CH_2Cl_2$ was treated with Grubbs catalyst (260 mg, 0.32 mmol) (commercially available from Strem). The progress of the reaction was followed by TLC and was complete after 3 d at rt. The solvent was removed under vacuum and the material was purified by chromatography on silica gel with 2% ether hexane to give t-butyl-dimethyl-[2-(5-methyl-3,6-dihydro-2H-pyran-2-yl)-ethoxy]-silane (Intermediate TWENTYSIX-4), 450 mg. A solution of t-butyl-dimethyl-[2-(5-methyl-3,6-dihydro-2H-pyran-2-yl)-ethoxy]-silane (Intermediate TWENTYSIX-4) (~450 mg) in ether (7 mL) was treated with TBAF (5 mL, 1 M in THF) at rt for 3 h. The mixture was diluted with ether (20 mL) and washed with water (1×10 mL). The organic layer was isolated and dried over $MgSO_4$, filtered and evaporated under vacuum. Chromatography on $SiO_2$ with 30 to 60% EtOAc:hexane gave 2-(5-methyl-3,6-dihydro-2H-pyran-2-yl)-ethanol, 100 mg. A solution of oxalyl chloride (0.5 mL, 1 mmol) in $CH_2Cl_2$ (1 mL) was treated with DMSO (0.080 mL, 1.1 mmol) at −78° C. for 30 m. A solution of 2-(5-methyl-3,6-dihydro-2H-pyran-2-yl)-ethanol (100 mg) was added and the mixture was allowed to stir for 30 m. Triethylamine (0.5 mL, 3 mmol) was added and the mixture was allowed to stir for 45 m. The solution was quenched with water and $CH_2Cl_2$ (10 mL). The organic layer was isolated, dried and evaporated. The residue was purified on silica gel with 30% EtOAc:hexane to give (5-methyl-3,6-dihydro-2H-pyran-2-yl)-acetaldehyde (Intermediate TWENTYSIX-5), 90 mg. Use of (5-methyl-3,6-dihydro-2H-pyran-2-yl)-acetaldehyde (Intermediate TWENTYSIX-5) in the applicable process steps described in Method A produced 4-(5-methyl-3,6-dihydro-2H-pyran-2-ylmethyl)-1,3-dihydro-imidazole-2-thione (Compound 171).

$^1$H NMR (300 MHz, $CDCl_3$) δ 10.8 (s, 1H), 9.95 (s, 1H), 6.47 (s, 1H), 5.46 (s, 1H), 4.05 (s, 2H), 3.73-3.62 (m, 1H), 2.76-2.63 (m, 1H), 2.58 (dd, J=8.4, 7.5 Hz, 1H), 2.03-1.88 (m, 2H), 1.61 (s, 3H).

Example P

Compound 41

Method P: Procedure for the preparation 4-(1,2,3,4,5,6-hexahydro-pentalen-1-ylmethyl)-1,3-dihydro-imidazol-2-one (Compound 41)

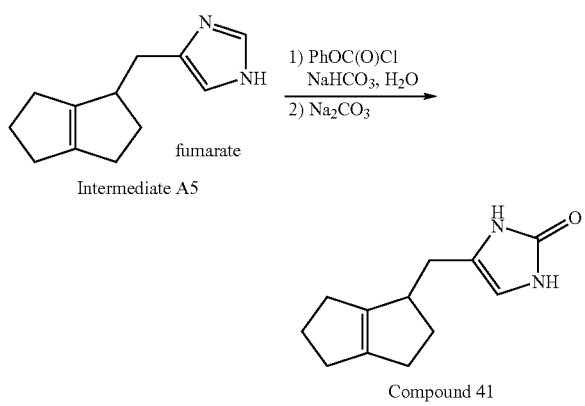

A solution of 4-(1,2,3,4,5,6-hexahydro-pentalen-1-ylmethyl)-1H-imidazole; fumarate salt (Intermediate A5 as described in Example A, 340 mg, 1.81 mmol) in THF (15 mL) and water (15 mL) was treated with NaHCO$_3$ (1.52 g, 18 mmol) at rt for 30 m. Phenyl chloroformate (600 mL, 4.7 mmol) was added and stirring was continued for 1 h at 65° C. The mixture was diluted with water (30 mL) and extracted with EtOAc (3×30 mL). The organic portions were combined and freed of solvent. The residue was dissolved in EtOH (15 mL): water (15 mL) and treated with Na$_2$CO$_3$ (500 mg) for 1.5 h at 95° C. The mixture was cooled to rt and the product was collected on a glass frit to give a white solid (~50%) 4-(1,2,3,4,5,6-Hexahydro-pentalen-1-ylmethyl)-1,3-dihydro-imidazol-2-one (Compound 41).

$^1$H NMR (300 MHz, DMSO-d$^6$): δ 9.69 (s, 1H), 9.38 (s, 1H), 5.92 (s, 1H), 2.70 (brs, 1H), 2.40-2.30 (m, 3H), 2.12-1.99 (m, 9H), 1.85-1.78 (m, 1H).

Example P2

Compound 42

Use of 3-methyl-cyclopent-2-enone (commercially available from Aldrich) in the applicable steps combined from Method A and Method P produced 4-(3-methyl-cyclopent-2-enylmethyl)-1,3-dihydro-imidazol-2-one (Compound 42).

$^1$H NMR (300 MHz, DMSO-d$^6$ w/TMS): δ 9.67 (s, 1H), 9.38 (s, 1H), 5.93 (s, 1H), 5.25 (s, 1H), 3.16 (d, J=5.4 Hz, 1H), 2.82-2.11 (m, 3H), 2.0-1.96 (m, 1H), 1.67 (s, 3H), 1.50-1.46 (m, 1H).

Example P3

Compound 43

Use of 2-ethyl-cyclopent-2-enone (commercially available from Aldrich) in the applicable steps combined from Method A and Method P produced 4-(2-ethyl-cyclopent-2-enylmethyl)-1,3-dihydro-imidazol-2-one (Compound 43).

$^1$H NMR (300 MHz, CD$_3$OD-d$^4$): δ 6.05 (s, 1H), 5.38 (brs, 1H), 3.31-3.29 (m, 1H), 2.75 (brs, 1H), 2.67-2.60 (m, 1H), 2.25-1.98 (series of m, 7H), 1.62-1.55 (m, 1H), 1.07 (t, J=10 Hz, 3H).

Example P4

Compound 44

Use of 2,3-dimethyl-cyclopent-2-enone (commercially available from Aldrich) in the applicable steps combined from Method A and Method P produced 4-(2,3-dimethyl-cyclopent-2-enylmethyl)-1,3-dihydro-imidazol-2-one (Compound 44).

$^1$H NMR (300 MHz, CD$_3$OD-d$^4$): δ 6.04 (s, 1H), 2.73 (brs, 1H), 2.68-2.61 (m, 1H), 2.27-2.19 (m, 2H), 2.13-2.05 (m, 1H), 1.99-1.87 (m, 1H), 1.63 (s, 6H), 1.55-1.46 (m, 1H).

Example P5

Compound 45

Use of 3,4-dihydro-2H-naphthalen-1-one (commercially available from Aldrich) in the applicable steps combined from Method A and Method P produced 4-(1,2,3,4-tetrahydro-naphthalen-1-ylmethyl)-1,3-dihydro-imidazol-2-one (Compound 45).

$^1$H NMR (300 MHz, DMSO-d$^6$ w/TMS): δ 9.86 (s, 1H), 9.40 (s, 1H), 7.16-7.04 (m, 4H), 5.96 (s, 1H), 2.97 (brs, 1H), 2.69-2.29 (series of m, 5H), 1.66-1.60 (m, 3H).

Example P6

Compound 46

Use of indan-1-one (commercially available from Aldrich) in the applicable steps combined from Method A and Method P produced 4-indan-1-ylmethyl-1,3-dihydro-imidazol-2-one (Compound 46).

$^1$H NMR (300 MHz, DMSO-d$^6$ w/TMS): δ 9.83 (s, 1H), 9.43 (s, 1H), 7.21-7.13 (m, 4H), 5.95 (s, 1H), 3.40-3.28 (m, 1H), 2.95-2.63 (m, 3H), 2.30-2.12 (m, 2H), 1.70-1.59 (m, 1H).

Example P7

Compound 47

Use of 3-methyl-indan-1-one (commercially available from Aldrich) in the applicable steps combined from Method A and Method P produced 4-(3-methyl-indan-1-ylmethyl)-1,3-dihydro-imidazol-2-one (Compound 47).

$^1$H NMR (500 MHz, DMSO-d$^6$ w/TMS): δ (diastereomers) 9.85 (s, 1H), 9.45 (s, 1H), 7.17-7.08 (m, 4H), 6.00 (5.92) (s, 1H), 3.34-2.86 (series of m, 2H), 2.37-2.22 (series of m, 2H), 1.99-1.95 (m, 1H), 1.71-1.67 (m, 1H), 1.18 (1.25) (d, J=6.5 Hz, 3H), 1.50-1.14 (m, 2H).

Example P8

Compound 48

Use of 4-methyl-indan-1-one (commercially available from Aldrich) in the applicable steps combined from Method A and Method P produced 4-(4-methyl-indan-1-ylmethyl)-1,3-dihydro-imidazol-2-one.

¹H NMR (500 MHz, DMSO-d⁶ w/TMS): δ 9.83 (s, 1H), 9.44 (s, 1H), 7.02-6.91 (m, 3H), 5.92 (s, 1H), 3.28 (brs, 1H), 2.79-2.74 (m, 1H), 2.66-2.63 (m, 2H), 2.25-2.10 (m, 2H), 2.17 (s, 3H), 1.65-1.61 (m, 1H).

Example P9

Compound 49

Use of 5-fluoro-indan-1-one (commercially available from Aldrich) in the applicable steps combined from Method A and Method P produced 4-(5-fluoro-indan-1-ylmethyl)-1,3-dihydro-imidazol-2-one (Compound 49).

¹H NMR (300 MHz, DMSO-d⁶ w/TMS): δ 9.83 (s, 1H), 9.44 (s, 1H), 7.14-6.91 (m, 3H), 5.95 (s, 1H), 3.31-3.28 (m, 1H), 2.88-2.60 (m, 3H), 2.31-2.14 (m, 2H), 1.75-1.70 (m, 1H).

Example P10

Compound 50

Use of 5-methoxy-indan-1-one (commercially available from Aldrich) in the applicable steps combined from Method A and Method P produced 4-(5-methoxy-indan-1-ylmethyl)-1,3-dihydro-imidazol-2-one (Compound 50).

¹H NMR (500 MHz, DMSO-d⁶ w/TMS): δ 9.81 (s, 1H), 9.43 (s, 1H), 7.02-6.67 (m, 3H), 5.94 (s, 1H), 3.26-3.23 (m, 1H), 3.70 (s, 3H), 2.83-2.59 (series of m, 3H), 2.26-2.10 (m, 2H), 1.67-1.63 (m, 1H).

Example P11

Compound 51

Use of 5-bromo-indan-1-one (commercially available from Aldrich) in the applicable steps combined from Method A and Method P produced 4-(5-bromo-indan-1-ylmethyl)-1,3-dihydro-imidazol-2-one (Compound 51).

¹H NMR (500 MHz, DMSO-d⁶ w/TMS): δ 9.83 (s, 1H), 9.45 (s, 1H), 7.39 (d, J=5 Hz, 1H), 7.30 (d, J=8.5 Hz, 1H), 7.07 (d, J=8.5 Hz, 1H), 5.95 (s, 1H), 3.29 (brs, 1H), 2.87-2.61 (series of m, 3H), 2.31-2.14 (m, 2H), 1.70-1.68 (m, 1H).

Example P12

Compound 52

Use of 6-methyl-indan-1-one (commercially available from Aldrich) in the applicable steps combined from Method A and Method P produced 4-(6-methyl-indan-1-ylmethyl)-1,3-dihydro-imidazol-2-one (Compound 52).

¹H NMR (500 MHz, DMSO-d⁶ w/TMS): δ 9.87 (s, 1H), 9.48 (s, 1H), 7.07 (d, J=7.5 Hz, 1H), 6.97-6.93 (m, 2H), 5.96 (s, 1H), 3.29-3.26 (m, 1H), 3.80-2.66 (m, 3H), 2.25 (s, 3H), 2.36-2.11 (m, 2H), 1.66-1.62 (m, 1H).

Example P13

Compound 53

Use of 6-methoxy-indan-1-one (commercially available from Aldrich) in the applicable steps combined from Method A and Method P produced 4-(6-methoxy-indan-1-ylmethyl)-1,3-dihydro-imidazol-2-one (Compound 53).

¹H NMR (500 MHz, DMSO-d⁶ w/TMS): δ 9.86 (s, 1H), 9.48 (s, 1H), 7.08 (d, J=7.5 Hz, 1H), 6.69 (brs, 2H), 3.69 (s, 3H), 3.30-3.27 (m, 1H), 2.78-2.65 (series of m, 3H), 2.29-2.10 (m, 2H), 1.68-1.64 (m, 1H).

Example Q

Compound 54

Procedure for preparation of 4-(1-oxo-1,2,3,4-tetrahydro-naphthalen-2-ylmethyl)-1,3-dihydro-imidazol-2-one (Compound 54) and 4-(4,5,6,7-tetrahydro-benzo[b]thiophen-5-ylmethyl)-1,3-dihydro-imidazol-2-one (Compound 55)

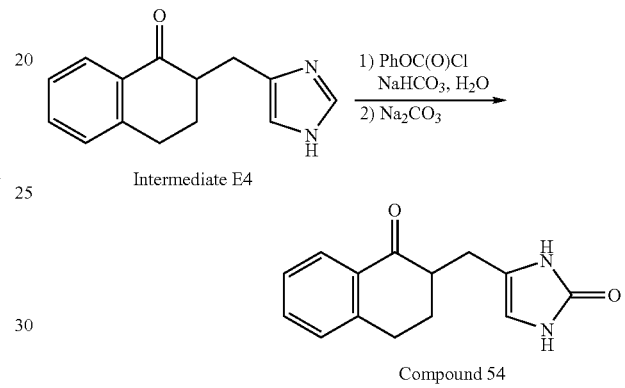

2-(1H-imidazol-4-ylmethylene)-3,4-dihydro-2H-naphthalen-1-one (Intermediate E4, as described in Example E, 1.4 g) was subjected to the applicable steps of Method P to provide 4-(1-oxo-1,2,3,4-tetrahydro-naphthalen-2-ylmethyl)-1,3-dihydro-imidazol-2-one (Compound 54) isolated as a white solid (~50%).

¹H NMR (300 MHz, DMSO-d₆ w/TMS) δ 9.70 (s, 1H), 9.45 (s, 1H), 7.88-7.86 (m, 1H), 7.57-7.51 (m, 1H), 7.37-7.32 (m, 2H), 2.95-2.90 (m, 3H), 2.82-2.70 (m, 1H), 2.30-2.20 (m, 1H), 2.15-2.05 (m, 1H), 1.75-1.68 (m, 1H).

Synthesis of 4-(4,5,6,7-tetrahydro-benzo[b]thiophen-5-ylmethyl)-1,3-dihydro-imidazol-2-one (Compound 55) from 6,7-dihydro-5H-benzo[b]thiophen-4-one was accomplished from 4-(4,5,6,7-tetrahydro-benzo[b]thiophen-5-ylmethyl)-1H-imidazole (Intermediate F3 as described in Example A) in the applicable reaction sequence of Method P, and shown below.

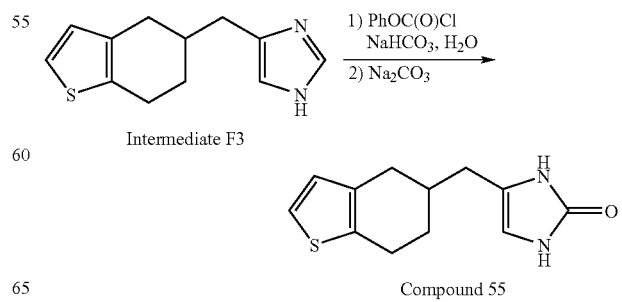

4-(4,5,6,7-tetrahydro-benzo[b]thiophen-5-ylmethyl)-1,3-dihydro-imidazol-2-one (Compound 55)

$^1$H NMR (300 MHz, DMSO-d$^6$) δ 9.72 (s, 1H), 9.42 (s, 1H), 7.21 (d, J=6.0 Hz, 1H), 6.75 (d, J=6.0 Hz, 1H), 5.99 (s, 1H), 2.83-2.60 (m, 3H), 2.28-2.15 (m, 3H), 2.02-1.85 (m, 2H), 1.43-1.35 (m, 1H).

Example R

Compound 56

Method R: Synthesis of 4-(3-hydroxymethyl-cyclohex-3-enylmethyl)-1,3-dihydro-imidazol-2-one (Compound 56)

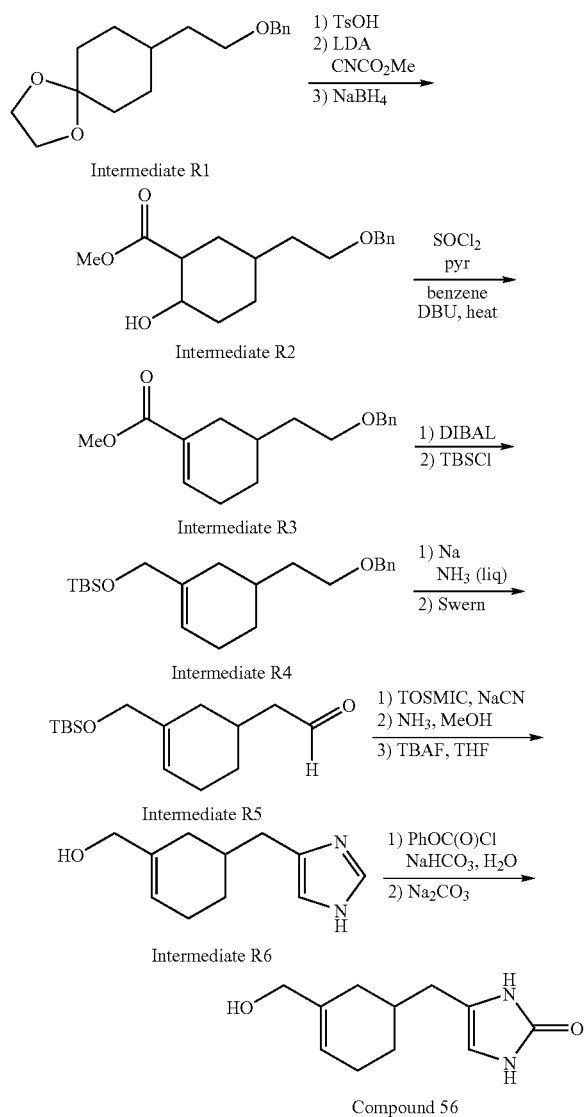

8-(2-Benzyloxy-ethyl)-1,4-dioxa-spiro[4.5]decane (Intermediate R1, 1.02 g, 3.70 mmol) (obtainable as described in the publication by Ciufolini et. al. J. Amer. Chem. Soc. 1991, 113, 8016, incorporated herein by reference) was dissolved in acetone (100 mL): H$_2$O (5 mL) and reacted with TsOH (140 mg, 0.74 mmol) at 45° C. for 5 h. After a standard aqueous work-up the material was purified by chromatography on SiO$_2$ to give 4-(2-benzyloxy-ethyl)-cyclohexanone as a colorless oil (97%).

A solution of LDA (33 ml, 1.5 M in Et$_2$O) in THF (50 mL) at −78° C. was treated with 4-(2-benzyloxy-ethyl)-cyclohexanone (9.5 g, 40.2 mmol). The mixture was warmed to 0° C. over 30 m before re-cooling to −78° C. and adding HMPA (7 mL). Methyl cyanoformate (4.1 mL, 85 mmol) was added and the mixture was stirred for 15 m before aqueous quench and work-up. The product was purified by chromatography on SiO$_2$ with 10% EtOAc:Hx. 5-(2-Benzyloxy-ethyl)-2-oxo-cyclohexanecarboxylic acid methyl ester was isolated, 5.8 g (49%) and reduced with an equivalent of NaBH$_4$ in MeOH at −10° C. to provide the alcohol (Intermediate R2). Intermediate R2 was purified by chromatography on SiO$_2$ with 30 to 50% EtOAC:Hx. (~90% yield).

A solution of 5-(2-benzyloxy-ethyl)-2-hydroxy-cyclohexanecarboxylic acid methyl ester (Intermediate R2, 0.72 g, 2.48 mmol) in pyridine (10 mL) was treated with SOCl$_2$ (0.73 mL, 12.4 mmol) at −20° C. The mixture was allowed to react for 15 m and was then warmed to 55° C. for 16 h. The solvents were removed under vacuum and the residue was diluted in ether at 0° C. The solution was quenched with water, washed with 1M HCl, 5% NaOH and brine. The organic material was dried over MgSO$_4$ filtered and freed of solvent. The mixture was diluted with benzene and water was removed by azeotropic distillation under vacuum. The residue was dissolved in benzene (15 mL) and DBU (0.76 mL, 5 mmol) was added. The mixture was reacted for 30 m at rt. After work-up and chromatography on SiO$_2$ with 20% EtOAc:Hx 5-(2-benzyloxy-ethyl)-cyclohex-1-enecarboxylic acid methyl ester (Intermediate R3) was isolated 0.56 g (82%).

Intermediate R3 was dissolved in THF (100 mL) and added to a solution of DIBAL (70 mL, 1M in hexanes) in THF (160 mL) at −35° C. for 35 m. The mixture was quenched with Rochelle's salt solution, and extracted with ether. The dried residue was purified by chromatography on SiO$_2$ with 30% EtOAc:Hx to yield [5-(2-benzyloxy-ethyl)-cyclohex-1-enyl]-methanol 4.6 g (80%). A solution of the alcohol (4.0 g, 18.7 mmol) in DMF (60 mL) was treated with triethylamine (3 mL) followed by TBSCl (3.0 g, 22.4 mol) for 20 m at rt. The residue was isolated from an aqueous work-up and purified by chromatography to give [5-(2-benzyloxy-ethyl)-cyclohex-1-enylmethoxy]-tert-butyl-dimethyl-silane (Intermediate R4, 3.6 g (63%). The benzyl and tert-butyl-dimethyl-silyl protected alcohol (Intermediate R4, 2.0 g, 5.55 mmol) in THF (20 mL) was cooled to −70° C. and NH$_3$ was condensed in this flask (~20 mL). Na chunks were added and the mixture was allowed to stir at −70° C. for 15 m. The mixture was warmed to −30° C. for 20 m. The mixture was quenched with NH$_4$Cl and the alcohol from which the benzyl protecting group has been removed was isolated by extraction. The residue was purified by chromatography on SiO$_2$ with 25% EtOAc:Hx (99%).

The alcohol was oxidized by the standard "Swern" protocol (see Mancuso Synthesis supra) as follows. The alcohol 2-[3-(tert-butyl-dimethyl-silanyloxymethyl)-cyclohex-3-enyl]-ethanol (1.3 g, 5.89 mmol) was added to a solution of oxalyl chloride (3.55 mL, 7.1 mmol) in CH$_2$Cl$_2$ (30 mL) with DMSO (0.63 mL, 8.9 mmol) at −78° C. After 40 m, NEt$_3$ (2.51 mL) was added and the mixture was warmed to rt. After standard aqueous work-up and purification, [3-(tert-butyl-dimethyl-silanyloxymethyl)-cyclohex-3-enyl]-acetaldehyde (Intermediate R5) was isolated (~95%). The aldehyde (Intermediate R5) was subjected to the applicable steps of Method P to form 4-(3-hydroxymethyl-cyclohex-3-enylmethyl)-1,3-dihydro-imidazol-2-one (Compound 56).

$^1$H NMR (300 MHz, CD$_3$OD-d$^4$) δ 6.04 (s, 1H), 5.66 (s, 1H), 3.90 (s, 2H), 2.34 (d, J=7.2 Hz, 2H), 2.15-2.06 (m, 3H), 1.85-1.65 (m, 3H), 1.29-1.15 (m, 1H).

Example R2

Compound 57

Procedure for the synthesis of 4-(3-Methyl-cyclohex-3-enylmethyl)-1,3-dihydro-imidazol-2-one (Compound 57)

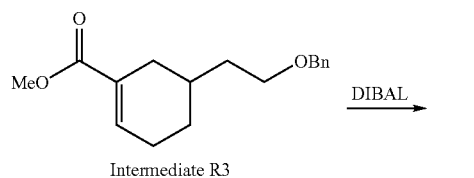

Intermediate R3

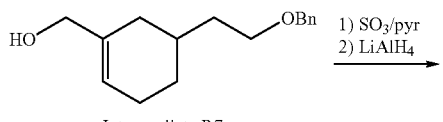

Intermediate R7

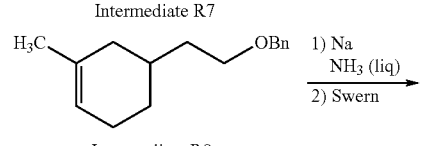

Intermediate R8

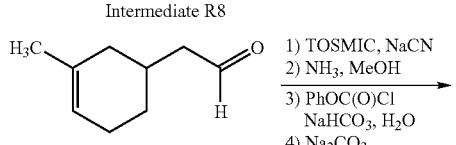

Intermediate R9

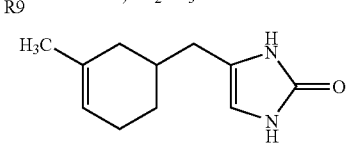

Compound 57

5-(2-Benzyloxy-ethyl)-cyclohex-1-enecarboxylic acid methyl ester (Intermediate R3 obtained above in Example R1 in accordance with Method R) was reduced with DIBAL. The resulting alcohol (Intermediate R7, 1.18 g, 4.81 mmol) in THF (20 mL) at 0° C. was treated with sulfur trioxide-pyridine. (1.15 g, 7.21 mmol) for 3 h. LiAlH$_4$ (15 mL, 15 mmol) was injected into the mixture at 0° C. The solution was allowed to warm to rt for 18 h. The mixture was subjected to an aqueous work-up and purified by chromatography to give [2-(3-methyl-cyclohex-3-enyl)-ethoxymethyl]-benzene (Intermediate R8, 0.90 g, 82%). Deprotection with Na/NH$_3$ and subsequent "Swern" oxidation produced (3-methyl-cyclohex-3-enyl)-acetaldehyde (Intermediate R9). (3-methyl-cyclohex-3-enyl)-acetaldehyde (Intermediate R9) was subjected to the applicable steps combined from Method A and Method P to yield 4-(3-methyl-cyclohex-3-enylmethyl)-1,3-dihydro-imidazol-2-one (Compound 57).

$^1$H NMR (300 MHz, DMSO-d$^6$) d 9.64 (s, 1H), 9.35 (s, 1H), 5.92 (s, 1H), 2.14 (d, J=6.9 Hz, 2H), 1.94-1.74 (m, 4H), 1.62-1.50 (m, 2H), 1.57 (s, 3H), 1.09-0.96 (m, 1H).

Example R3

Compound 58

Synthesis of 4-(3-ethyl-4-methyl-cyclohex-3-enylmethyl)-1,3-dihydro-imidazol-2-one (Compound 58)

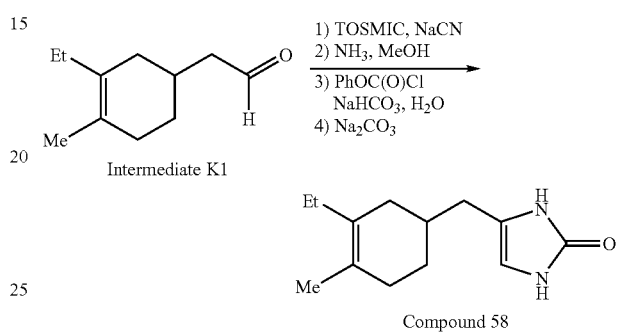

(3-Ethyl-4-methyl-cyclohex-3-enyl)-acetaldehyde (Intermediate K1 as prepared in Example K) was subjected to the applicable steps combined from Method A and Method P to yield 4-(3-ethyl-4-methyl-cyclohex-3-enylmethyl)-1,3-dihydro-imidazol-2-one (Compound 58).

$^1$H NMR (300 MHz, CD$_3$OD) δ 6.05 (s, 1H), 2.29 (d, J=6.9 Hz, 2H), 2.00-1.97 (m, 4H), 1.75-1.59 (m, 6H), 1.26-1.12 (m, 1H), 1.0-0.88 (m, 4H).

Example R4

Compound 59

Procedure for the preparation of 4-(3-ethyl-cyclohex-3-enylmethyl)-1,3-dihydro-imidazol-2-one (Compound 59)

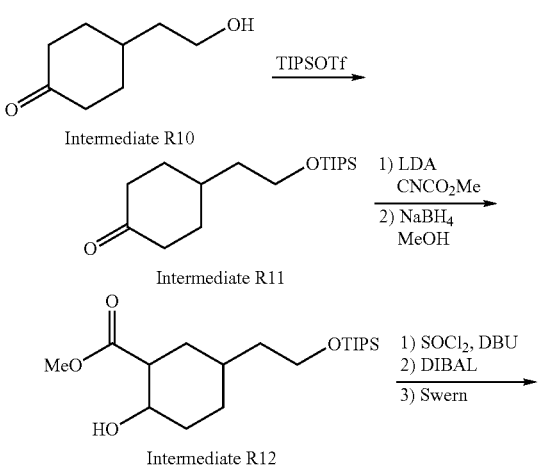

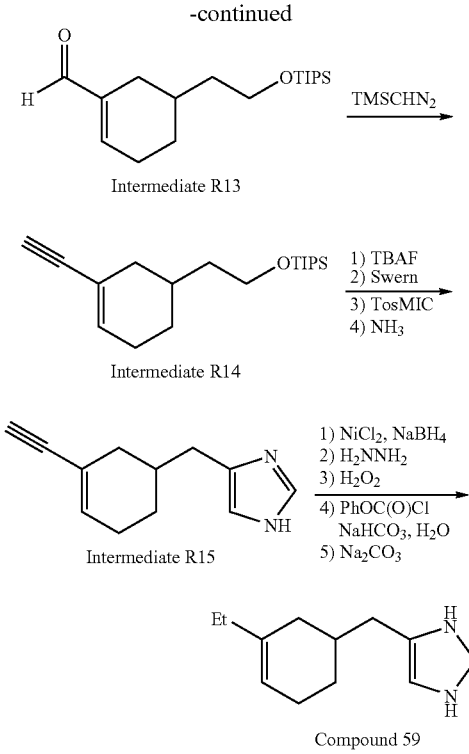

alkynyl imidazol (Intermediate R15, 0.26 g, 1.40 mmol) at rt for 45 m under an atmosphere of hydrogen gas. The mixture was filtered, diluted with chloroform and subjected to an aqueous work-up. The residue was purified by chromatography on $SiO_2$ to give 4-(3-vinyl-cyclohex-3-enylmethyl)-1H-imidazole (72%). To 4-(3-vinyl-cyclohex-3-enylmethyl)-1H-imidazole (0.09 g, 0.47 mmol) in ethanol (3 mL) at 0° C. was added $H_2NNH_2$—$H_2O$ (0.93 mL, 19.1 mmol) followed by $H_2O_2$ (30%) (0.488 g, 14.4 mmol) and the mixture was stirred for 45 m at 0° C. and an additional 6 h at rt. The reaction was quenched and the material was purified by an aqueous work-up. The imidazole compound was purified further by isolation of the fumaric acid salt. The fumarate was converted to the compound 4-(3-ethyl-cyclohex-3-enylmethyl)-1,3-dihydro-imidazol-2-one (Compound 59) by the applicable step of Method P.

$^1$H NMR (300 MHz, $CD_3OD$) δ 6.05 (s, 1H), 5.37 (s, 1H), 2.31 (d, J=6.6 Hz, 2H), 2.03-1.10 (m, 9H), 0.97 (t, J=7.5 Hz, 3H).

Example S

Compound 60

Procedure for the preparation of 4-(3,4-dimethyl-cyclohex-3-enylmethyl)-1,3-dihydro-imidazol-2-one (Compound 60)

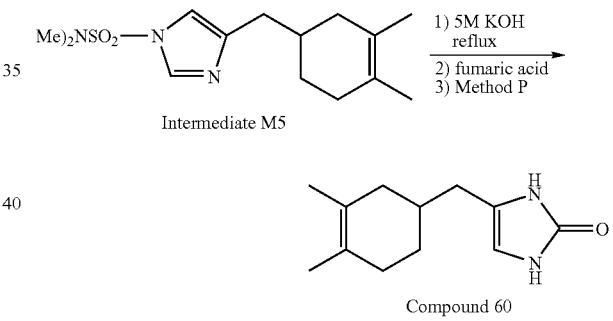

To Intermediate M5 (obtained in accordance with Example M (0.53 g, 1.77 mmol) in MeOH (5 ml) was added aqueous KOH (15 ml of a 5M solution) and the mixture was heated at reflux for 32 h. The mixture was concentrated under reduced pressure, diluted with $H_2O$ (5 ml) and extracted exhaustively with $CHCl_3$. The combined organic fractions were washed consecutively with $H_2O$ and brine, dried ($MgSO_4$) and concentrated under reduced pressure. The resulting imidazole was recrystallized by stirring in MeOH with an equimolar amount of fumaric acid until all solids had disappeared followed by the addition of a small amount of diethyl ether. 4-(3,4-Dimethyl-cyclohex-3-enylmethyl)-1H-imidazole-fumarate 0.27 g (57%) was recovered as pale yellow crystals. 4-(3,4-dimethyl-cyclohex-3-enylmethyl)-1H-imidazole-fumarate was subjected to the applicable steps of Method P to yield 4-(3,4-dimethyl-cyclohex-3-enylmethyl)-1,3-dihydro-imidazol-2-one (Compound 60).

$^1$H NMR (300 MHz, $CD_3OD$-d$^4$): d 6.04 (s, 1H), 2.29 (d, J=9 Hz, 2H), 2.00-1.96 (m, 3H), 1.79-1.69 (m, 3H), 1.59 (s, 6H), 1.21-1.17 (m, 1H).

A solution of 4-(2-hydroxy-ethyl)-cyclohexanone (Intermediate R10, 6.8 g, 52.6 mmol, (obtainable as described in the publication by Ciufolini et. al. J. Amer. Chem. Soc. 1991, 113, 8016) was dissolved in $CH_2Cl_2$ (75 mL) and treated with diisopropylethylamine (9.2 mL, 52.6 mmol) followed by triisopropylsilyl trifluoromethane sulfonate (TIPSTf) (15.3 g, 50.2 mmol) at −30° C. The reaction mixture was warmed to 0° C. for 1 h. The mixture was subjected to an aqueous work-up and purified by chromatography on $SiO_2$ to give 4-(2-triisopropylsilanyloxy-ethyl)-cyclohexanone (Intermediate R11, 11.8 g (82%). Intermediate R11 was converted via Intermediate R12 to the unsaturated aldehyde, 5-(2-triisopropylsilanyloxy-ethyl)-cyclohex-1-enecarbaldehyde (Intermediate R13)

A solution of TMS-diazomethane (4.61 mL, 9.22 mmol) in THF (60 mL) was reacted with n-BuLi (5.0 mL, 7.99 mmol) at −78° C. for 0.5 h. 5-(2-triisopropylsilanyloxy-ethyl)-cyclohex-1-enecarbaldehyde (Intermediate R13) was added via cannula. The mixture was reacted at −78° C. for 1 h and at 0° C. for 1 h. After work-up and chromatographic purification, [2-(3-ethynyl-cyclohex-3-enyl)-ethoxy]-triisopropyl-silane (Intermediate R14) was isolated, 1.44 g (77%). To Intermediate R14 in THF (70 mL) at 0° C. was injected tetrabutyl ammonium fluoride (TBAF). After 2 h at rt the mixture was subjected to an aqueous work-up. The material was purified by chromatography to give the alcohol, 2-(3-ethynyl-cyclohex-3-enyl)-ethanol 0.68 g, (98%). The alcohol was oxidized by a Swern reaction to the aldehyde stage and aldehyde was subjected to the applicable step of Method A to yield 4-(3-ethynyl-cyclohex-3-enylmethyl)-1H-imidazole (Intermediate R15).

A mixture of $NiCl_2$ (0.364 g, 2.81 mmol) in EtOH (20 mL) was reacted with $NaBH_4$ (0.053 mg, 1.40 mmol) at rt for 15 m after saturation of the solution with hydrogen gas. Ethylene diamine (0.17 g, 2.81 mmol) was added followed by the

Example T

Compound 61 and Compound 62

Procedure for the preparation of R-(+)-4-(5-fluoro-indan-1-ylmethyl)-1,3-dihydro-imidazol-2-one (Compound 61) and of S-(−)-4-(5-fluoro-indan-1-ylmethyl)-1,3-dihydro-imidazol-2-one (Compound 62)

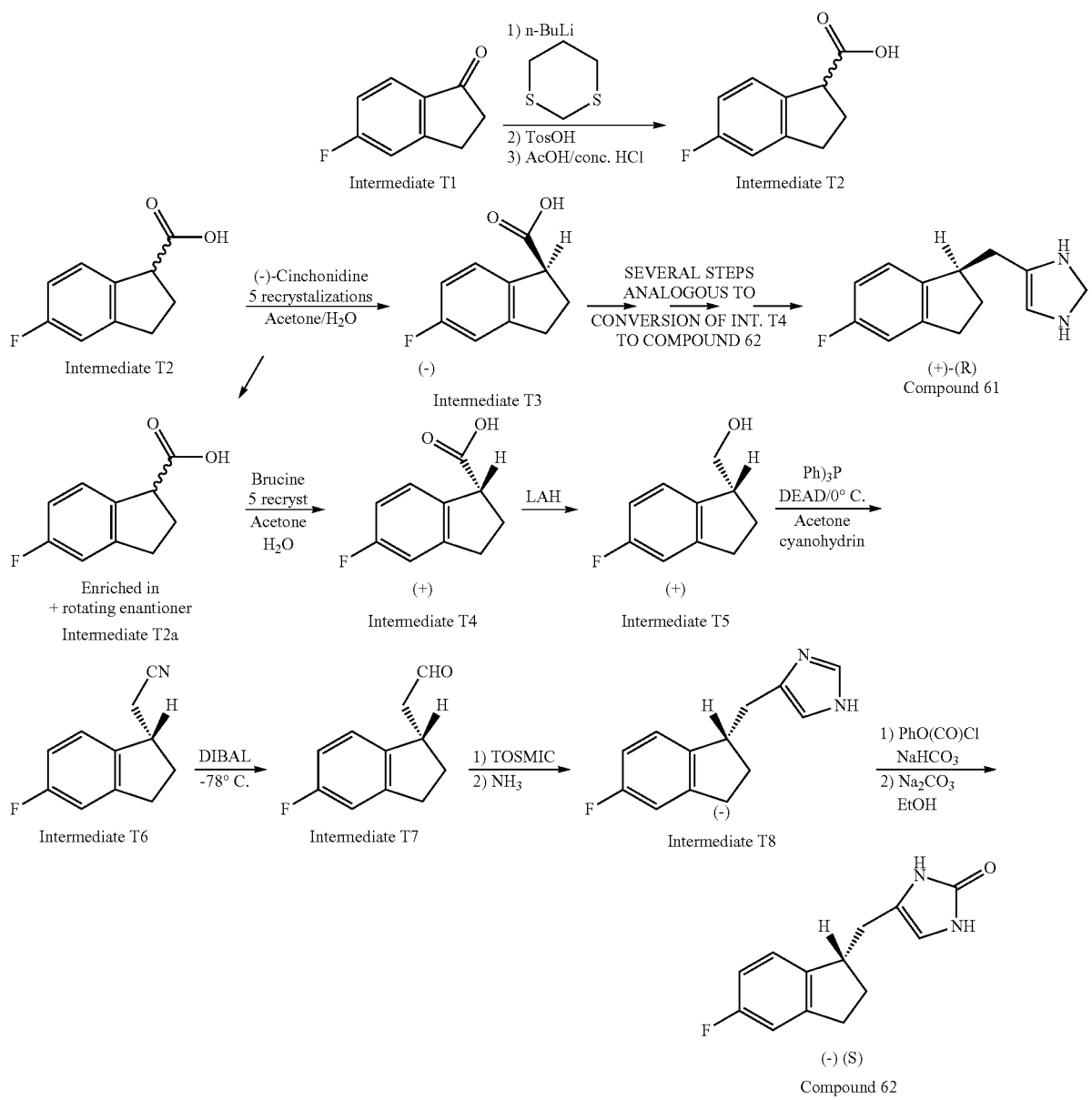

To 1,3-dithiane (available from Aldrich, 34.1 g, 283.4 mmol) in THF (anhydrous, 373 ml) at −30° C. under argon was added n-BuLi (136.0 ml of a 2 M solution in cyclohexane) at a rate by which the internal temperature of the reaction was maintained below −25° C. After addition was complete the reaction was allowed to warm to −15° C. and stirred for 2 hours. The reaction was then allowed to warm to 0° C. and 5-fluoro-indan-1-one (Intermediate T1, commercially available from Aldrich) (34.0 g, 226.7 mmol) in THF (anhydrous, 1 L) was added dropwise over 2 hours. After stirring for 20 hours at 0° C. the reaction was concentrated at reduced pressure and the residues were taken up in Et$_2$O (600 ml) and washed consecutively with 1N HCl, H$_2$O and brine and then concentrated at reduced pressure. This residue was taken up in benzene (1 L) and p-toluenesulfonic acid-H$_2$O (8.6 g, 45.3 mmol) was added. This solution was refluxed in a flask equipped with a Dean Stark trap until no more H$_2$O was collected. The reaction was cooled to 20° C. and washed consecutively with H$_2$O, saturated aqueous NaHCO$_3$, brine, dried (MgSO$_4$), filtered and concentrated at reduced pressure. This residue was taken up in a solution of glacial AcOH (1 L) and concentrated HCl (400 ml) and heated at reflux for 3 hours. The reaction was concentrated at reduced pressure and subjected to azeotropic removal of aqueous liquid by distillation on a rotary evaporator (3 times) with toluene (100 ml). The residues were taken up in Et$_2$O (200 ml) and washed with H₂O until the washings were neutral. This solution was extracted 3 times with NaOH (75 ml portions of a 5% aqueous solution) and the combined aqueous portions were washed 3 times with Et₂O (50 ml portions), then treated with decolorizing charcoal and filtered through celite. The resulting aqueous solution was cooled to 0° C., carefully acidified to pH 3 with conc. HCl and extracted 3 times with CH₂Cl₂. The combined organic portions were washed with H₂O and brine, dried (MgSO₄), filtered and concentrated at reduced pressure. The resulting solids were recrystallized from hexanes to give 26.2 g (64%) of racemic carboxylic acid (Intermediate T2).

To the racemic carboxylic acid (Intermediate T2, 107.1 g, 595.0 mmol) in refluxing acetone (500 ml) was added in portions (−)-cinchonidine (175.2 g, 595.0 mmol). Additional acetone was gradually added to the refluxing mixture until most solids had gone into solution (final volume was 3.5 L). The solution was filtered while hot and then reduced in volume to 800 ml and H₂O (900 ml) was added with stirring. The resulting solution was allowed to stand for 16 hours at room temperature. The resulting solid salt was removed by filtration and recrystallized four more times in similar manner from acetone and H₂O to give a white solid which was taken up in 0° C. 5N HCl (200 ml). This solution was extracted 3 times with Et₂O (200 ml portions) and the combined Et₂O portions were washed successively with 1N HCl, H₂O and brine, dried (MgSO₄), filtered and concentrated under reduced pressure to give 18.9 g (35% of theoretical) of (S)-5-fluoro-indan-1-carboxylic acid (Intermediate T3) as a pale solid with $[\alpha]^{20}_D$ −33.5 (c=3.66, benzene).

(S)-5-Fluoro-indan-1-carboxylic acid (Intermediate T3) was used in the synthesis of R-(+)-4-(5-fluoro-indan-1-ylmethyl)-1,3-dihydro-imidazol-2-one (Compound 61) in analogy to the procedure shown in the scheme above for the synthesis of Compound 62 which is described below. Compound 61: $[\alpha]^{20}_D$ +12.5 (c=0.6, DMSO).

¹H NMR (500 MHz, DMSO-d⁶) δ 9.80 (s, 1H), 9.42 (s, 1H), 7.11-7.08 (m, 1H), 7.01-6.99 (m, 1H), 6.91-6.87 (m, 1H), 5.93 (s, 1H), 3.30-3.25 (m, 1H), 2.88-2.70 (m, 2H), 2.65-2.58 (m, 1H), 2.32-2.10 (m, 2H), 1.71-1.66 (m, 1H).

The combined mother liquors from the resolution of Intermediate T3 were concentrated under reduced pressure until no acetone remained and acidified to pH 3 with 0° C. 5N HCl. This solution was extracted 3 times with Et₂O (200 ml portions) and the combined Et₂O portions were washed successively with 1N HCl, H₂O and brine, dried (MgSO₄), filtered and concentrated under reduced pressure to give a yellow solid (71 g). This residue was recrystallized from hexane to give pure 5-fluoro-indan-1-carboxylic acid (Intermediate 2a, 58.6 g, 325.5 mmol) which was enriched in the R enantiomer. To Intermediate 2a in refluxing acetone (1 L) was added pulverized brucine (128.4 g, 325.5 mmol). After most solids had dissolved the solution was hot filtered and reheated to reflux as H₂O (1 L) was added gradually. Excess acetone was boiled off until the solution became hazy. The solution was allowed to stand in a recrystallization dish for 1 month before solids appeared. The resultant solids were broken up, filtered off and recrystallized four more times in similar manner from acetone and H₂O to give a buff colored solid which was taken up in 0° C. 1N HCl (150 ml). This solution was extracted 3 times with Et₂O (75 ml portions) and the combined Et₂O portions were washed successively with 1N HCl, H₂O and brine, dried (MgSO₄), filtered and concentrated under reduced pressure to give 6.13 g of (R)-5-fluoro-indan-1-carboxylic acid (Intermediate T4) as a pale solid which rotates sodium light at 20° C. with $[\alpha]^{20}_D$ +31.8 (c=4.49, benzene).

To a solution of LAH (33.8 ml of a 1M solution in THF) in THF (anhydrous, 30 ml) at 0° C. under argon was added the carboxylic acid (Intermediate T4, 3.04 g, 16.90 mmol) in THF (anhydrous, 30 ml) dropwise via syringe. This mixture was stirred 30 minutes at 0° C. and then allowed to stir at 20° C. for 1 hour. The reaction was then recooled to 0° C. and quenched with the successive addition of H₂O (1.3 ml), 15% aqueous NaOH (1.3 ml) and H₂O (2.6 ml). This mixture was stirred 30 minutes at 20° C. and then filtered. The filtrate was concentrated under reduced pressure and the residues were purified by chromatography on SiO₂ with 20% EtOAc:hexanes to give 2.69 g of the alcohol (Intermediate T5, 96%) with $[\alpha]^{20}_D$ +17.1 (c=6.04, benzene).

Triphenylphosphine (10.62 g, 40.48 mmol) in a solution of THF (anhydrous, 125 ml) at 0° C. under argon was treated with DEAD (6.77 g, 38.86 mmol). After stirring 5 minutes the alcohol (Intermediate T5, 2.69 g, 16.93 mmol) and acetone cyanohydrin (3.31 g, 38.86 mmol) in THF (anhydrous, 50 ml) were added concurrently via cannula. This mixture was allowed to stir at 20° C. for 20 hours. The mixture was concentrated under reduced pressure, the residues were taken up in Et₂O, washed consecutively with saturated aqueous K₂CO₃, H₂O and brine, dried (MgSO₄) and concentrated under reduced pressure. The residues were purified by chromatography on SiO₂ with 20% EtOAc:hexanes to give 2.69 g of the nitrile (Intermediate T6). This mixture was carried on without further purification.

To the nitrile (Intermediate T6, 2.00 g, 11.43 mmol) in Et₂O (anhydrous, 50 ml) at −78° C. under argon was added DIBAL (22.9 ml of a 1 M solution in THF) and the reaction was allowed to warm gradually to −40° C. Additional DIBAL (21.0 ml of a 1 M solution in THF) was added to the reaction mixture at −40° C. over a period of 24 hours until no starting material was visible by thin layer chromatography. The reaction was quenched with a saturated aqueous solution of sodium potassium tartrate. After stirring a 20° C. for 1 hour the solids were filtered off and the filtrate was taken up in Et₂O and washed consecutively with H₂O and brine, dried (MgSO₄) and concentrated under reduced pressure. The residues were purified by chromatography on SiO₂ with 10% EtOAc:hexanes to give 0.94 g of pure aldehyde (Intermediate T7, 47%) with $[\alpha]^{20}_D$ −2.5 (c=5.58, benzene).

A solution of the aldehyde (Intermediate T7, 0.90 g, 5.06 mmol) in EtOH (anhydrous, 15 ml) was treated with tosylmethyl isocyanide (TosMIC) (0.94 g, 4.81 mmol) and NaCN (0.013 g, 0.25 mmol) at 20° C. for 20 minutes. This mixture was concentrated under reduced pressure and the resulting residue was taken up in MeOH saturated with NH₃ (anhydrous, 10 ml) and heated in a sealed tube at 100° C. for 16 hours. The reaction mixture was concentrated under reduced pressure and purified by chromatography on SiO₂ with 10% MeOH:CH₂Cl₂ to give 0.59 g (54%) of the imidazole (Intermediate T8) which rotates sodium light at 20° C. with $[\alpha]^{20}_D$ −14.7 (c=3.72, MeOH).

To the imidazole (Intermediate T8, 0.55 g, 2.56 mmol) in a solution of THF (15 ml) and H₂O (15 ml) was added NaHCO₃ (2.15 g, 25.60 mmol) followed by phenyl chloroformate (1.00 g, 6.40 mmol). After heating at 65° C. for 2 hours the mixture was cooled and washed consecutively with H₂O and brine, dried (MgSO₄) and concentrated under reduced pressure. The residues were taken up in EtOH (10 ml) and H₂O (15 ml), treated with Na₂CO₃ (0.77 ml, 7.29 mmol) and heated at reflux for 1 hour. After cooling the solids were filtered off, washed with H₂O, Et₂O and dried for 20 hours under high vacuum to give (Compound 62, 0.39 g (66%) with $[\alpha]^{20}_D$ −10.0 (c=1.08, in DMSO). ¹H NMR (300 MHz, DMSO-d⁶) δ 9.80 (s, 1H), 9.42 (s, 1H), 7.15-7.06 (m, 1H), 7.04-6.97 (m, 1H), 6.96-6.87 (m, 1H), 5.93 (s, 1H), 3.35-3.21 (m, 1H), 2.92-2.68 (m, 2H), 2.67-2.56 (m, 1H), 2.32-2.09 (m, 2H), 1.76-1.62 (m, 1H).

Example U

Compound 63

Procedure for the preparation of 4-(5-hydroxy-indan-1-ylmethyl)-1,3-dihydro-imidazol-2-one (Compound 63)

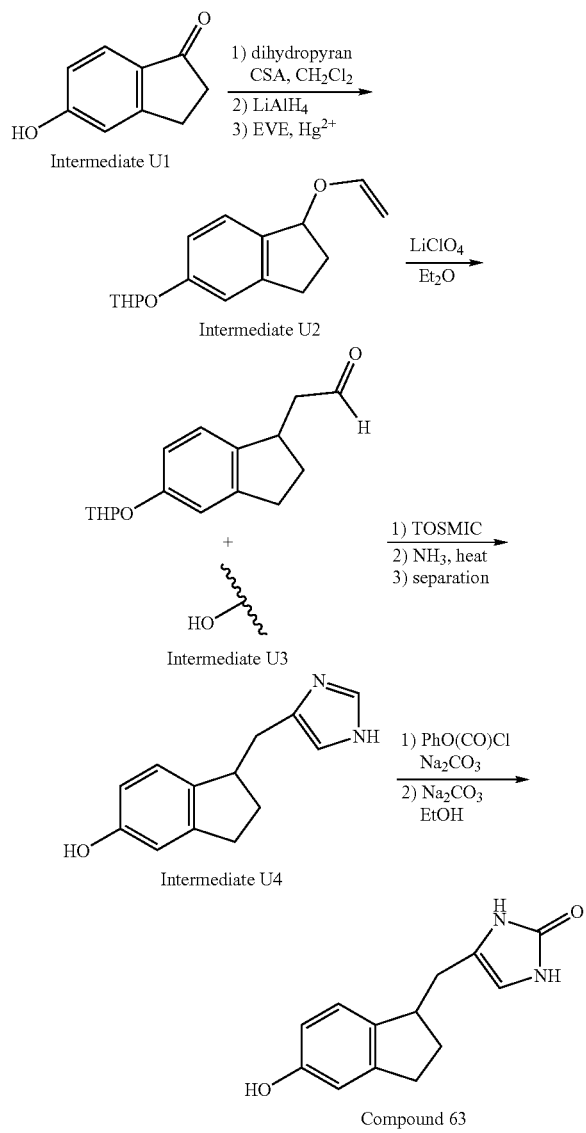

Use of 5-(tetrahydro-pyran-2-yloxy)-indan-1-one in the applicable steps of Method A and Method P produced Compound 63. Note: a separation of the THP protected compound, 4-[5-(tetrahydro-pyran-2-yloxy)-indan-1-ylmethyl]-1H-imidazole from the hydroxy compound 1-(1H-imidazol-4-ylmethyl)-indan-5-ol (Intermediate U4, shown in the scheme above) was accomplished by chromatography on $SiO_2$ with 3 to 5% $NH_3$-MeOH in $CH_2Cl_2$. 4-(5-hydroxy-indan-1-ylmethyl)-1,3-dihydro-imidazol-2-one (Compound 63):
$^1$H NMR (300 MHz, $CD_3OD$-$d^4$): δ 6.93 (d, J=13 Hz, 1H), 6.62-6.53 (m, 2H), 6.01 (s, 1H), 2.83-2.68 (m, 4H), 2.43-2.35 (m, 1H), 2.24-2.17 (m, 1H), 1.16-1.69 (m, 1H).

Example V

Compound 64

Procedure for preparation 4-(2-ethyl-3-methyl-cyclopent-2-enylmethyl)-1,3-dihydro-imidazol-2-one (Compound 64)

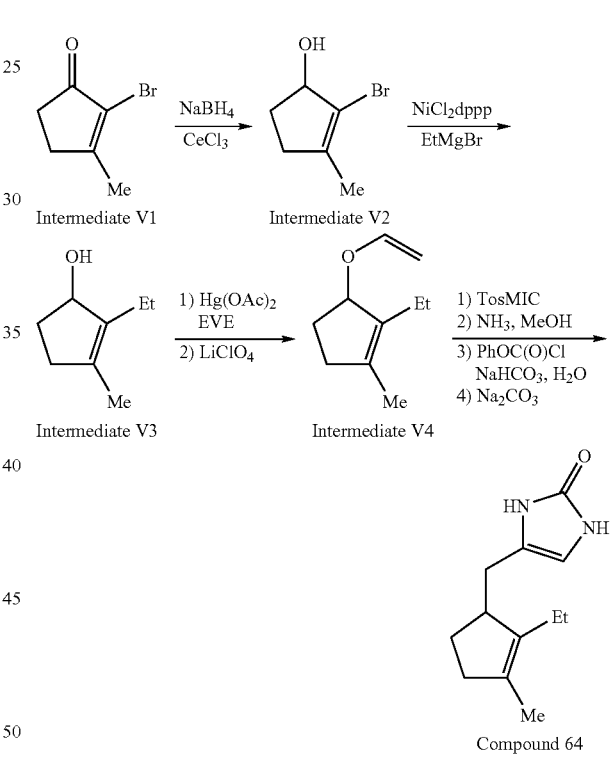

2-Bromo-3-methyl-cyclopent-2-enone (Intermediate V1, commercially available from Aldrich) (18 mmol) was dissolved in 0.4M $CeCl_3$ $7H_2O$ in MeOH (66 mL) at 0° C. Sodium borohydride (20 mmol) was added portion-wise and stirring was continued for 10 m after addition was complete. The mixture was quenched with saturated $NH_4Cl$ and extracted with ether. The combined organic layers were washed with sat. $NH_4Cl$, $H_2O$, brine, and dried over $Na_2SO_4$, filtered and evaporated to dryness. The material was purified by column chromatography 15% EtOAc:Hx to give 2-bromo-3-methyl-cyclopent-2-enol (Intermediate V2, ~80%).

The alcohol (Intermediate V2, 16 mmol) in THF (30 mL) at 0° C. was treated with ethyl magnesium bromide (40 mmol). The catalyst, 1,3-bis(diphenylphosphino)propane nickel (II) chloride (0.75 mmol) ($NiCl_2$dppp) was added in one portion A solution of 5-hydroxyindanone (available from Aldrich, 1.48 g, 10 mmol) in $CH_2Cl_2$ (10 mL) and dihydropyran (5 mL) was treated with camphor sulphonic acid (~50 mg catalytic amount) at 0° C. The mixture was allowed to warm to room temperature and stirring was continued for 2 h. The mixture was subjected to an aqueous work-up, extracted with ether, dried over $MgSO_4$, filtered and evaporated to dryness. The protected indanone, 5-(tetrahydro-pyran-2-yloxy)-indan-1-one was used in the next step without further purification.

and the mixture was heated to reflux for 3 hours following the procedure of Organ et al. J. Org. Chem. 1997, 62, 1523, incorporated herein by reference.) The reaction mixture was cooled to rt and quenched with sat. $NH_4Cl$ solution. The mixture was filtered and partitioned between brine and diethyl ether. The organic layer was removed and dried over $Na_2SO_4$, filtered and concentrated under vacuum. The oil was purified by chromatography on $SiO_2$ with 20% EtOAc:Hx to yield 2-ethyl-3-methyl-cyclopent-2-enol (Intermediate V3). Use of the alcohol (Intermediate V3) in the applicable steps of Method A and Method P produced 4-(2-ethyl-3-methyl-cyclopent-2-enylmethyl)-1,3-dihydro-imidazol-2-one (Compound 64). $^1H$ NMR (300 MHz, $CD_3OD$-$d^4$): δ 6.03 (s, 1H), 2.88 (brs, 1H), 2.65-2.59 (m, 1H), 2.27-1.83 (series of m, 6H), 1.62 (s, 3H), 1.54-1.45 (m, 1H), 0.97 (t, J=6 Hz, 3H).

What is claimed is:

1. A method of activating $alpha_{2B}$ or $alpha_{2C}$ adrenergic receptors in a mammal in need of such activation by administering to the mammal a pharmaceutical composition containing a therapeutically effective dose of an $alpha_{2B}$ or $alpha_{2C}$ receptor agonist compound having the formula:

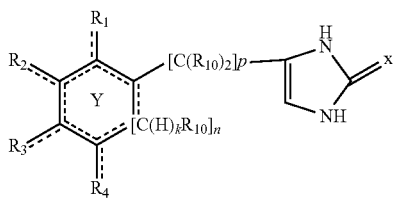

wherein the variable Y in the ring is optional and represents a heteroatom selected from N, O and S with the proviso that the N atom is trivalent, and the O or S atoms are divalent;
k is an integer having the values of 0 or 1;
n is an integer having the values 1 or 2;
p is an integer having the values 0, 1 or 2;
X is O or S;
the dashed lines represent a bond, or absence of bond with the proviso that only one double bond is present in the ring and that two adjoining dashed lines do not both represent a bond;
$R_1$, $R_2$, $R_3$, and $R_4$ are independently H, phenyl, said phenyl group being optionally substituted independently with one, two or three $C_{1-6}$alkyl, $SO_3H$, $N_3$, halogen, CN, $NO_2$, $NH_2$, $C_{1-6}$alkoxy, $C_{1-6}$thioalkoxy, $C_{1-6}$alkylamino, $C_{1-6}$dialkylamino, $C_{2-6}$alkynyl or $C_{2-6}$alkenyl groups, 5 or 6 membered heteroaryl having 1 to 3 heteroatoms selected from O, S, and N, said heteroaryl groups being optionally substituted independently with one, two or three $C_{1-6}$alkyl, $SO_3H$, $N_3$, halogen, CN, $NO_2$, $NH_2$, $C_{1-6}$alkoxy, $C_{1-6}$thioalkoxy, $C_{1-6}$alkylamino, $C_{1-6}$dialkylamino, $C_{2-6}$alkynyl or $C_{2-6}$alkenyl groups,
or said $R_1$, $R_2$, $R_3$, and $R_4$ groups are independently alkyl of 1 to 4 carbons, cycloalkyl of 3 to 5 carbons, $CH_2CN$, $CH_2SR_5$, $CH_2NR_6R_6$, $COR_5$, $CH_2OR_5$, $OR_6$, $SR_6$. $NR_6R_6$, alkenyl having 1 to 4 carbons, alkynyl having 1 to 4 carbons, cycloalkyl having 3 to 6 carbons, F, Cl, Br, I, $CF_3$, or CN, an oxygen double bonded to the ring carbon with the proviso that the adjacent dashed line within the ring represents absence of a bond;
$R_5$ is H, $OR_7$, alkyl of 1 to 4 carbons, $CF_3$, cycloalkyl of 3 to 6 carbons, phenyl, phenyl substituted with one or two alkyl groups of 1 to 4 carbons, with F, Cl, Br, I, or with $CF_3$, or $R_5$ is a 5 or 6 membered heteroaryl having 1 to 3 heteroatoms selected from O, S, and N, and 5 or 6 membered heteroaryl having 1 to 3 heteroatoms selected from O, S, and N substituted with one or two alkyl groups of 1 to 4 carbons, with F, Cl, Br, I, or with $CF_3$;
$R_6$ is H, alkyl of 1 to 4 carbons, allyl, cycloalkyl of 3 to 6 carbons, phenyl, phenyl substituted with one or two alkyl groups of 1 to 4 carbons, with F, Cl, Br, I, or with $CF_3$, or $R_6$ is 5 or 6 membered heteroaryl having 1 to 3 heteroatoms selected from O, S, and N, or 5 or 6 membered heteroaryl having 1 to 3 heteroatoms selected from O, S, and N substituted with one or two alkyl groups of 1 to 4 carbons, with F, Cl, Br, I, or with $CF_3$;
$R_7$ is H, alkyl of 1 to 4 carbons, allyl, cycloalkyl of 3 to 6 carbons, phenyl, phenyl substituted with one or two alkyl groups of 1 to 4 carbons, with F, Cl, Br, I, or with $CF_3$;
$R_1$ and $R_2$ or $R_2$ and $R_3$ or $R_3$ and $R_4$ together can form a ring together with the respective carbons to which each of these is attached, the portion contributed by $R_1$ and $R_2$ or by $R_2$ and $R_3$ or by $R_3$ and $R_4$ having the formulas (i), (ii), (iii), (iv) or (v)

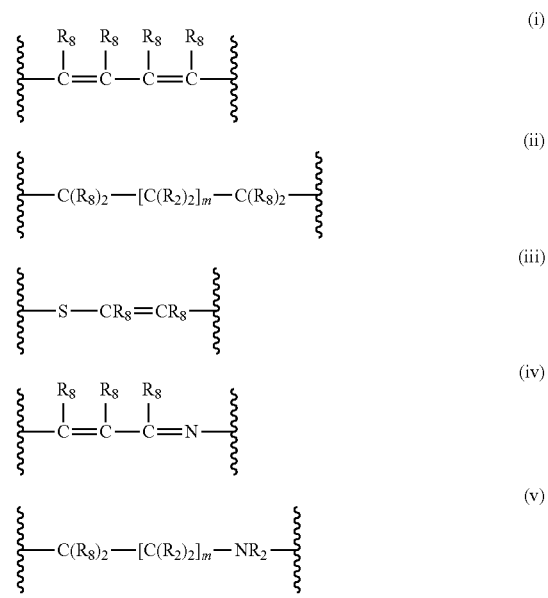

m is an integer having the values 0 to 3;
$R_8$ is independently H, alkyl of 1 to 6 carbons, alkenyl of 2 to 6 carbons, alkynyl of 2 to 6 carbons, $SO_3H$, $N_3$, CN, $NO_2$, F, Cl, Br, I, $CF_3$, $COR_9$, $CH_2OR_9$, $OR_{10}$; $SR_{10}$, $C_{1-6}$alkylamino, or $C_{1-6}$dialkylamino;
$R_9$ is H, alkyl of 1 to 6 carbons, or $OR_{10}$, and
$R_{10}$ independently is H or alkyl of 1 to 6 carbons,
or a pharmaceutically acceptable salt thereof
with the proviso that the formula does not include the compounds shown below by structural formula or their pharmaceutically acceptable salts

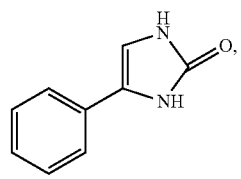

-continued

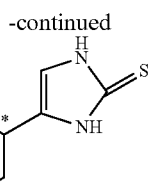

where an asterisk indicates an asymmetrical carbon, wherein said administering activates the $alpha_{2B}$ or $alpha_{2C}$ adrenergic receptors in said mammal.

2. A method in accordance with claim 1 where the pharmaceutical composition is administered to the mammal to alleviate pain.

3. A method in accordance with claim 1 where the pharmaceutical composition is administered to the mammal to alleviate chronic pain.

4. A method in accordance with claim 1 where the pharmaceutical composition is administered to the mammal to alleviate allodynia.

5. A method in accordance with claim 1 where the pharmaceutical composition is administered orally.

6. A method in accordance with claim 1 where the pharmaceutical composition is administered intraperitonially.

7. A method in accordance with claim 1 where the mammal is administered the composition for treating a condition selected from the group consisting of chronic pain, visceral pain, neuropathic pain, corneal pain, glaucoma, elevated intraocular pressure, ischemic neuropathies, diarrhea, nasal congestion, fibromyalgia, muscle spasticity, diuresis, withdrawal syndromes, optic neuropathy, spinal ischemia, stroke, memory and cognition deficits, attention deficit disorder, manic disorders, anxiety, depression, hypertension, congestive heart failure, cardiac ischemia, arthritis, spondylitis, gouty arthritis, osteoarthritis, juvenile arthritis, lupus erythematosus, chronic gastrointestinal inflammations, Crohn's disease, gastritis, irritable bowel disease (IBD), functional dyspepsia and ulcerative colitis.

8. A method in accordance with claim 7 where the mammal is administered the composition for treating glaucoma.

9. A method in accordance with claim 7 where the mammal is administered the composition for treating muscle spasticity.

* * * * *